(12) United States Patent
Denolf et al.

(10) Patent No.: US 9,968,041 B2
(45) Date of Patent: May 15, 2018

(54) SOYBEAN ROD1 GENE SEQUENCES AND USES THEREOF

(71) Applicant: Bayer CropScience NV, Diegem (BE)

(72) Inventors: Peter Denolf, Velzeke (BE); Michel Van Thournout, Sint-Michiels (BE)

(73) Assignee: BAYER CROPSCIENCE NV, Diegem (BE)

( * ) Notice: Subject to any disclaimer, the term of this patent is extended or adjusted under 35 U.S.C. 154(b) by 43 days.

(21) Appl. No.: 14/409,712

(22) PCT Filed: Jul. 4, 2013

(86) PCT No.: PCT/EP2013/064187
§ 371 (c)(1),
(2) Date: Dec. 19, 2014

(87) PCT Pub. No.: WO2014/006159
PCT Pub. Date: Jan. 9, 2014

(65) Prior Publication Data
US 2015/0322447 A1    Nov. 12, 2015

Related U.S. Application Data

(60) Provisional application No. 61/669,703, filed on Jul. 10, 2012.

(30) Foreign Application Priority Data

Jul. 6, 2012   (EP) ..................... 12175304

(51) Int. Cl.
| | | |
|---|---|---|
| A01H 5/10 | (2006.01) |
| A01H 1/04 | (2006.01) |
| A01H 1/06 | (2006.01) |
| A01H 1/02 | (2006.01) |
| C11B 1/10 | (2006.01) |
| C07K 14/705 | (2006.01) |
| C12Q 1/68 | (2018.01) |
| C12N 9/12 | (2006.01) |
| C12N 15/82 | (2006.01) |
| A23D 9/00 | (2006.01) |
| A23K 10/30 | (2016.01) |

(52) U.S. Cl.
CPC .............. *A01H 1/04* (2013.01); *A01H 1/02* (2013.01); *A01H 1/06* (2013.01); *A01H 5/10* (2013.01); *A23D 9/00* (2013.01); *A23K 10/30* (2016.05); *C07K 14/705* (2013.01); *C11B 1/10* (2013.01); *C12N 9/1288* (2013.01); *C12N 15/8218* (2013.01); *C12N 15/8247* (2013.01); *C12Q 1/6895* (2013.01); *C12Y 207/08002* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 5,985,557 | A | 11/1999 | Prudent et al. | |
|---|---|---|---|---|
| 6,001,567 | A | 12/1999 | Brow et al. | |
| 8,609,953 | B2 * | 12/2013 | Fillatti | A01H 5/10 435/415 |
| 2004/0031072 | A1 | 2/2004 | La Rosa et al. | |
| 2009/0019601 | A1 | 1/2009 | Kovalic | |
| 2017/0022502 | A1 | 1/2017 | Dickson et al. | |

FOREIGN PATENT DOCUMENTS

| DE | 10211617 A1 | 3/2002 | |
|---|---|---|---|
| EP | 0534858 A1 | 9/1992 | |
| WO | 8903887 A1 | 5/1989 | |
| WO | 8910396 A1 | 11/1989 | |
| WO | 9213956 A1 | 8/1992 | |
| WO | 9606932 A1 | 3/1996 | |
| WO | 9713865 A1 | 4/1997 | |
| WO | 9845461 A1 | 10/1998 | |
| WO | 9953050 A1 | 10/1999 | |
| WO | 0001133 A1 | 1/2000 | |
| WO | 02059294 A1 | 8/2002 | |
| WO | 03014347 A2 | 2/2003 | |
| WO | 03076619 A1 | 9/2003 | |
| WO | 06005807 A1 | 1/2006 | |
| WO | 06074400 A2 | 7/2006 | |
| WO | 06105946 A2 | 10/2006 | |
| WO | 07106728 A2 | 9/2007 | |
| WO | 09002150 A1 | 12/2008 | |
| WO | 09007091 A2 | 1/2009 | |
| WO | 09073738 A1 | 6/2009 | |
| WO | 09077478 A2 | 6/2009 | |
| WO | 09111587 A2 | 9/2009 | |
| WO | WO 2009111587 A2 * | 9/2009 | .............. A01H 5/00 |

(Continued)

OTHER PUBLICATIONS

An, Yong-Qiang, et al., Conserved Expression of the Arabidopsis ACT7 and ACT1 and ACT3 Actin Subclass in Organ Primordia and Mature Pollen, The Plant Cell, Jan. 1996, vol. 8, pp. 15-30.
Azpiroz-Leehan, Ricardo, et al., T-DNA Insertion Mutagenesis in Arabidopsis: Going back and forth, TIG, Apr. 1997, vol. 13, No. 14.
Broun, Pierre, et al., Genetic Engineering of Plant Lipids, Annu. REv. Nutri., 1999, pp. 197-216, vol. 19.
Browse, John, et al., Glycerolipid Synthesis: Biochemistry and Regulation1, Ann. Rev. Plant Physiol. Plant Mo. Biol., 1991, pp. 467-506, vol. 42.
Chaubet, Nicole, et al., Nucleotide sequences of two corn histone H3 genes. Genomic organization of the corn histone H3 and H4 genes, Plant Molecular Biology, 1986, pp. 253-263, vol. 6.
Christensen, Alan H., et al., Maize polyubiquitin genes: structure, thermal perturbation of expression and transcript splicing, and promoter activity following transfer to protoplasts by electroporation, Plant Molecular Biology, 1992, pp. 675-689, vol. 18.
De Pater, Sylvia B., et al.; The promoter of the rice gene Gos2 is active in various different monocot tissues and binds rice nuclear factor ASF-I, The Plant Journal, 1992, pp. 837-844, vol. 2 No. 6.
Depicker, A., et al., Nopaline Synthase: Transcript Mapping and DNA Sequence, Journal of Molecular and Applied Genetics, 1982, pp. 561-573.

(Continued)

Primary Examiner — Elizabeth F McElwain

(57) ABSTRACT

The present invention relates to soybean ROD1 nucleic acid sequences and proteins and the use thereof to create plants with increased levels of C18:1 and reduced levels of saturated fatty acids in the seeds.

9 Claims, No Drawings

(56) References Cited

FOREIGN PATENT DOCUMENTS

| WO | 09125826 A1 | 10/2009 |
|---|---|---|
| WO | 11132127 A1 | 10/2011 |

OTHER PUBLICATIONS

Gunstone, F.D., Movements Towards Tailor-Made Fats, Prog. Lipid Res., 1998, pp. 277-305, vol. 37, No. 5.
Harpster, Mark H., et al., Relative strengths of the 35S califlower mosaic virus, 1', 2', and nopaline synthase 110 !promoters in transformed tobacco sugarbeet and oilseed rape callus tissue, Mol. Gen. Genet, 1988, pp. 182-190, vol. 212.
Henikoff, Steven, et al., Tilling. Traditional Mutagenesis Meets Functional Genomics, Plant Physiology, Jun. 2004, pp. 630-636, vol. 135.
Hudspeth, Richard L., et al., Structure and expression of the maize gene encoding the phosphoenolpyruvate carboxylase isozyme involved in C4 photosynthesis, Plant Molecular Biology, 1989, pp. 579-589, vol. 12.
Jaworski, Jan, et al., Industrial Oils from Transgenic Plants, Current Opinion in Plant Biology, 2003, pp. 178-187, vol. 6.
Keil, Michael, et al., Both wound-inducible and tuber-specific expression are mediated by the promoter of a single member of the potato proteinase inhibitor 11 gene family, The EMBO Journal, 1989, pp. 1323-1330, vol. 8, No. 5.
Keller; Beat, et al., Glycine-rich cell wall proteins in bean: gene structure and association of the protein with the vascular system, The EMBO Journal, 1988, pp. 3625-3633, vol. 7, No. 12.
Keller, Beat, et al., specific expression of a novel cell wall hydroxyproline-rich glycoprotein gene in lateral root initiation, Genes & Development, 1989, pp. 1639-1646, vol. 3.
Li. Xin, et al., Reverse genetics by fast neutron mutagenesis in higher plants, Funct Integr Genomics, 2002, pp. 254-258, vol. 2.
Li, Xin, et al., A fast neutron deletion mutagenesis-based reverse genetics system for plants, The Plant Journal, 2001, pp. 235-242, vol. 27, No. 3.
Lu, Chaofu, et al., An enzyme regulating triacyiglycerol composition is encoded by the ROD1 gene of Arabidopsis, PNAS, 2009, pp. 1-6.
McCallum, Claire M., et al., Targeted Screening for induced Mutations, Nature Biotechnology, Apr. 2000, pp. 455-457, vol. 18.
McCallum, Claire M., et al., Targeting Indduced Local Lesions in Genomes (TILLING) for Plant Functional Genomics, Plant Physiology, Jun. 200, pp. 439-442, vol. 123.
McElroy, David, et al., Isolation of an Efficient Actin Promoter for Use in Rice Transformation, The Plant Cell, Feb. 1990, pp. 163-171, vol. 2.
McKenzie, N., et al., Tissue-culture enhanced transposition of the maize transposable element Dissociation in *Brassica oleracea* var. 'Italica', Theor App Genet, 2002, pp. 23-33, vol. 105.
Miquel, Martine, et al., Arabidopsis Mutants Deficient in Polyunsaturated Fatty Acid Synthesis, The Journal of Biological Chemistry, Jan. 25, 1992, pp. 1502-1509, vol. 267, No. 3.
Needleman, Saul B., et al., A General Method Applicable to the Search for Similarities in the Amino Acid Sequence of Two Proteins, J. Mol. Biol., 1970, pp. 443-453, vol. 48.
Okuley, John, et al., Arabidopsis FAD2 Gene Encodes the Enzyme That is Essential for Polyunsaturated Lipid Synthesis, The Plant Cell, Jan. 1994, pp. 147-158, vol. 6.
Peleman, Johan, Structure and Expression analyses of the S-Adenosylmethionine Synthetase Gene Family in Arabidopsis Thaliana, Gene. 84, 1989, pp. 359-369.
Rice, Peter, et al., Emboss: The European Molecular Biology Open Software Suite, TIG, Jun. 200, pp. 276-277, vol. 16, No. 6.
Verdaguer, Bertrand, et al., Isolation and expression in transgenic tobacco and rice plants, of the cassava vein mosaic virus (CVMV) promoter, Plant Molecular Biology, 1996, pp. 1129-1139, vol. 31.
Vos, Pieter, et al., AFLP: a new technique for DNA fingerprinting, Nucleic Acids Research, 1995, pp. 4407-4414, vol. 23, No. 21.
GenBank Accession No. AW733693.1, Apr. 24, 2000.
GenBank Accession No. BW670367.1, Oct. 17, 2008.
GenBank Accession No. BW670368.1, Oct. 17, 2008.
GenBank Accession No. HO041720.1, Jun. 11, 2010.
ID I1KH05__SOYBN, Jun. 13, 2012.
ID I1KVF7_SOYBN, Jun. 13, 2012.
NCBI Reference Sequence: XM_003528267.2, Jan. 7, 2014.
NCBI Reference Sequence: XM_003531670.1, Nov. 8, 2011.
NCBI Reference Sequence: XP_003528315.1, Jan. 7, 2014.
NCBI Reference Sequence: XP_003531718.1, Nov. 8, 2011.

* cited by examiner

```
                         SEQUENCE LISTING

<160> NUMBER OF SEQ ID NOS: 6

<210> SEQ ID NO 1
<211> LENGTH: 6267
<212> TYPE: DNA
<213> ORGANISM: Soybean
<220> FEATURE:
<221> NAME/KEY: Intron
<222> LOCATION: (3265)..(3479)
<223> OTHER INFORMATION: First intron
<220> FEATURE:
<221> NAME/KEY: Intron
<222> LOCATION: (3618)..(4298)
<223> OTHER INFORMATION: Second intron

<400> SEQUENCE: 1
tgttaaaatc actcacaaaa ctgatcagcc ttgtgttgaa ggaataagca tccatatcct      60
ccgaacaata taactatcat ctccaaatga ttgtaaacga atttcactat aggaaatttg     120
tgtgaacatg cttaaaatat atataacctg aggaaacagt cttcggagat agatgagtca     180
aaccacaaat tacatgaaat tagtcggaga catgtcccta gcatataatc atataaaaga     240
agttgttgct gccatggtgg aaagactctc cgaagtaaat tactccaaca cccattttat     300 tatttttaa tagaattagc acaacatgcg tgaaatgatt agagtctttc cacccatgtt     360
agagtaattt atcatatgtt aatttgtacc cttttatata aattgtcatg acaaaaacaa     420
tgggaaaatg agatagtcaa aagctaagag cattagacta tataaaccca atacaaaatg     480
cggtacacag aacatgcata agttaattta caaaataaat ggcaagaaca ttgataattt     540
gggtcaaaat ttgtagcctg aattgttatc cacatagcta ggcacataat ataagttata     600
actatgagct attgggcaag acgctatctt aattcttatg caaacaaaga gaaactgcat     660
gtcacccacg tgcttgacgc cactcctttt cgtcttcttt ttatgacgca tgtgaggttc     720 agaattttc tgtcttcata tatatttaga gcttgttgcc ttcatcctgt tcaaagaatg     780
gaaatggtag ttagtggttg acatcatttg cgatttactc atgaaactta attgccttt     840 tatgtatcat atattgaatt ttttataatc tatgccattg tatgtttggg agagtagatt     900
agaaagaaaa agtcttcaca gtgagatgtt taataaaagg gattttaaga tatttgttag     960
taattaatcc aaacagacac tgaaagtgga gtgcaactaa ttttcactcc agtctccacc    1020
tcataaattt cgtccactcc tagtgtgagt agaatgtatt taaagtttaa agccaaaaac    1080
ggtaatatat aacattttc atcaccaacc aaaaagtaa tgtatgttgc tatattcttt     1140
ttttgaaaaa aaaactttt tctattttta tcttttgagg ttattttgc aatactacaa     1200 gaaagggac caattctga aatttgaatc ctaatcttgg tccaaccata taatatagat     1260 gatacttaa ttatttcctc actaactagc attgcttttc tacttagtga aatttactct     1320
gaggtgctgc tatataattc taggtgaaag gcaccattgc attttgttca ttgtaacact    1380
```

```
tactcatgtt tgcttgcatg ttgccttttg actcatgaat tgtcttccaa ttccaaacta    1440
cactgctaca tatgtattat tatttacaaa ttatcaaaag gataaccaac ttatcctttg    1500
attttttttc cttgtgtgat ggtcatgttt accgttttc cttgagggtc atagacttgg    1560
cattctttgc tgaagagcta ggttcatatc tttcggctag gtagttttg ttgcgtgaat    1620 tttttcaatg catggctcac tttgtttgtc tggattataa gaacatgcat gctttctaat    1680
tgagatgtct tgttgacaag ctcattgtgg ttggggttta actaacttgt aggcacacac    1740
atggtagaaa ggtgactgat tgtcattgt cccaatagat gacgttgatt tgctatgagc    1800
atctaatgtt tttcacagtt aaataatatt tggtaattat ccaaaaaaaa ttcatcttta    1860
ctcattttca attttatttt tttagtttta ttaattcagc atcctgcaat agagattttg    1920
atttcgagat ctgacaatta ttaaccattt ttgttttttc ttatatagca aattgcgcta    1980
tcctcgcaag ctccattttt tattacaaaa tatgcagttt tatcaaattt tgtaaaataa    2040
ttttaacaat tttttaaaat caagatatta ttacttgtga atcaaaatga tcggtgagat    2100
tactttagat aatcagctaa aaaatcaaac tcaactaatt atctatcaac tttgatgaat    2160
ttaattggtt catacacaaa tgaatatata ctcttatgta agaataatat aatatttatt    2220
gaaaataaat aatgtaatca tatatcccaa ataattgtaa tttttagttg tctaatattg    2280
aattgagaat aattttaaaat cataatgaac atatttatg agaaaatat cttttataaa    2340 aataaaaaat taaatttaaa cgatacagtc atacatgaat gattaaaaaa tataatgtta    2400
aaaaatcaca taatttttta aataatcaaa ttataataaa ttttaaatat ttatattaa    2460 ttatacaatc taaattttcat catctcattt ttatataata tacattccta tcatgatatg    2520
tctcctctat cataggtcag aatgttacga caactttaac cttttcccca taacttgctc    2580
agtgccaaaa tgcacagctc ataacacacc tcatccaagc aagtctcagc atcttccctg    2640
tgcggctgtg cgtgtaaata accatagaga atcacaatca cacccacatc acatgcatgc    2700
aagcaagacc aattaccact ttccattatt tttattctta aaaaaatgac caaaaaagaa    2760
aattgcgtaa tcctagaaac gtaaaaccaa cctcaaccta acctaggaaa ctccgtcacc    2820
actttccctc tcccatttt atatcattcg ccacacacat catatgtctt ccgcactgac    2880
aaaaaacgat atccaacggt catgaatggc ggcgctgagg cctccctcaa tcacaggcgc    2940
aaacaccaaa cagctcccgc cgacggcgct aaaggcgtta aggtagcaaa cggagccatg    3000
gggaagccgt cctcttccaa gcactcctgc ggcgcgtcgt tcatgaaatg gaccgtggct    3060
gacgctgtcc acgtggtgac gcaccattgg atgccgtgct tgttcgcatt ggggcttctc    3120
ttcttcatgg ccgtggagta cacgcttctc atggtgccgc cgtcgtcgcc gcccttcgac    3180
cttggcttca tcgccacacg ctccctccac gcgctcctcg agtcgtcgcc gaatctcaac    3240
acgctcttcg ccgggctcaa tacggtacgt cgtttacact ctctccagat ctgaatcttc    3300
agatctgaac gagtccgggt atttttttt tcttatttca gatttcgttg tgggtaattg    3360
cggaatcgaa tttgtttgaa ggaaatgcaa atgggttggt ctcaaaatct gatatttta    3420 ctgcgttttt taggttttag cattattcac tttgcattaa tgggttttga catgggtagg    3480
tgtttgtggg gatgcaaacg agttatatct tatggacgtg gctgattgaa ggacgcccca    3540
gagccacaat ttcagcattg ttcatgttca catgccgtgg gatttaggc tactccaccc    3600 agctcccatt gcctcaggtg agattcatca accaaacttt gaatcttga atttttcatt    3660 attttaactt ctttctttt ttgggaaaat agtctaccta cccaggattt ttttatacct    3720
```

-continued

```
tcattcaatg acttttcaaa gttttcaatt tttttgatag aataacgttg taatttttt     3780
tagattaaac tattcacttg ctctccatgt ttattctctt ttaagttttg gtcctatacc     3840
aacagaaaaa aaaactctaa attttagtct gtacgcaaat ttttatagca attttatacg     3900
aagagaacca tatctagtga tagcaacata aaccaaaact tcactaatat acatgtgttg     3960
gggactaaaa tctctaattt tctgatatat gaactaaaac ttaaaataaa aacaaattta     4020
aaggtaagtg aatagattaa tcttttgaat aagtaatcat tttgtcctta tctctaggtt     4080
ttagtttta tagaagtaat tttttatgt tttagtcttt gttatgagtt ttctgacagt       4140
gtaaaattgt caaaagtaa aagatataag aggattaaga cataacataa ttgttggaga      4200
ttaacatcta ggagcaaatg attaattaaa ccttaaacct taacctttt acacagtgta      4260
tagaaattaa acttttttgt ttgtttgatg ttgaacaggg ttttgggc tcgggtgtgg       4320
acttccctgt tgggaacgtg tctttttct tgtttttttc tgggcacgtt gcagggtcag     4380
tgattgcttc attggacatg aggaggatgc agaggtggga actggcttgg acttttgatg    4440
tgctcaatgt tttgcaagct gtgaggttgc tgggtacaag aggccattac actattgatt    4500
tggccgtagg ggttggtgct ggaattctct ttgattcttt agctggcaag tacgaagata    4560
gcaaaggaa tggtgctctc aaacacaatt tgattgcgtg aacaatgtgg atatagctaa     4620
aaaaattaac aaaccatcat ggaaaagtac acatggaggt gtaaagtaa aagagtgaga     4680
gggcaagggt ttgaatcgta aaaaaaataa ggtcaaagag tgatacatca tattattagg    4740
atttaggaca agtcttaaat cttaattacc gcgtaatttt aaatttgatt tatttcacta   4800
ctttttgtaa cctgttatta tagtatagag ttttttttcc ctactagtgg agtctgagtt   4860
ggaattcact tgccaattgc tatgatccca tgattgattg ctctaggtgg gtgttgttcc    4920
cactttgtgg acgacagtgt gttaaggag gttgatttta acatcaaatt ttaagatttt     4980
acttttagtt gattcatagt cattggagaa ctttgattgt attaaatttt gatttgattt    5040
taatttgaat acagtggtta ttgacttatt tctgaatgca agtttccttt tcttcgcccc    5100
cctcccaaag acaaatcgga tggacaaata cgaaaattcc actataaaaa aatctgaaac    5160
atatgagctg gttaagaaaa ttccttccca tgaatgaaat cgcattagag ctcattaatc    5220
ggtgacactt taccatgaaa ctgaatgcat ttttgttatc aaagtactat gtactagtag    5280
taaattgtag ttttggtaat attattaggg cgttggggt tagattcaac tttatacaaa     5340
attaattcta attccatgtt gaaagtcaaa acaacaaata ttagttattt ctattttttc    5400
agttttttaa catgatttg aggatcagaa tcaattccag taactattca aactcattat     5460
atgtatactt ttctcaaatt aattacactt tcagctggac taagagaaag aagaacctgt    5520
ttcaataata gtaacagatt aaagagataa ataaggtaac aagaccagca atttcctatg    5580
tccaatgtaa agagtggact ttacaatata cactatgtac ttaaaccaa cataagtatg     5640
atcgaaatga atatttatgt aaagtataat gctattcttc agactcagaa tccaattcaa   5700
tagtacacgt tccatcatct acattggcta gcgggttgta taggtgagaa ctaggatctg   5760
tgcatcctac aacaaaattc agatcgcagc gatcaccctg cgaagatgtt tcattcata    5820
attaagaaac tgaaagtgtt ccaaggagaa aaacagtgat tatttaaaag agtaaagaca   5880
ttgaagaatg gaagaatata ctcaccccctt cttttgacaa attaccaatc atagcacatt  5940
tggttataac tttatttgtg tctggaaata ttgcttgctc gcatgctcct tctttactca    6000
gttcctccgc caagccctac cacagaatag tacacccaat tcagggtcat gttaactaat   6060
gctctgaatg attccattgt tgtacattta gtttctttaa tagtgtcaaa attcatgtac   6120
```

-continued

```
taaattctca caagctcaaa tatagttgtc ttgtaatctt gtcatataaa aacaatagat      6180
aggaggactc attcttcact actcgactaa tgttttcttt tggggctact ttattatagt      6240
tttgccaaca acctccttttt agaatga                                         6267

<210> SEQ ID NO 2
<211> LENGTH: 1153
<212> TYPE: DNA
<213> ORGANISM: Soybean
<220> FEATURE:
<221> NAME/KEY: CDS
<222> LOCATION: (30)..(833)

<400> SEQUENCE: 2
gcactgacaa aaaacgatat ccaacggtc atg aat ggc ggc gct gag gcc tcc       53
                                Met Asn Gly Gly Ala Glu Ala Ser
                                1               5 ctc aat cac agg cgc aaa cac caa aca gct ccc gcc gac ggc gct aaa      101
Leu Asn His Arg Arg Lys His Gln Thr Ala Pro Ala Asp Gly Ala Lys
    10              15                  20 ggc gtt aag gta gca aac gga gcc atg ggg aag ccg tcc tct tcc aag      149
Gly Val Lys Val Ala Asn Gly Ala Met Gly Lys Pro Ser Ser Ser Lys
25              30                  35                  40 cac tcc tgc ggc gcg tcg ttc atg aaa tgg acc gtg gct gac gct gtc      197
His Ser Cys Gly Ala Ser Phe Met Lys Trp Thr Val Ala Asp Ala Val
                45                  50                  55 cac gtg gtg acg cac cat tgg atg ccg tgc ttg ttc gca ttg ggg ctt      245
His Val Val Thr His His Trp Met Pro Cys Leu Phe Ala Leu Gly Leu
            60                  65                  70 ctc ttc ttc atg gcc gtg gag tac acg ctt ctc atg gtg ccg ccg tcg      293
Leu Phe Phe Met Ala Val Glu Tyr Thr Leu Leu Met Val Pro Pro Ser
        75                  80                  85 tcg ccg ccc ttc gac ctt ggc ttc atc gcc aca cgc tcc ctc cac gcg      341
Ser Pro Pro Phe Asp Leu Gly Phe Ile Ala Thr Arg Ser Leu His Ala
    90                  95                  100 ctc ctc gag tcg tcg ccg aat ctc aac acg ctc ttc gcc ggg ctc aat      389
Leu Leu Glu Ser Ser Pro Asn Leu Asn Thr Leu Phe Ala Gly Leu Asn
105                 110                 115                 120 acg gtg ttt gtg ggg atg caa acg agt tat atc tta tgg acg tgg ctg      437
Thr Val Phe Val Gly Met Gln Thr Ser Tyr Ile Leu Trp Thr Trp Leu
                125                 130                 135 att gaa gga cgc ccc aga gcc aca att tca gca ttg ttc atg ttc aca      485
Ile Glu Gly Arg Pro Arg Ala Thr Ile Ser Ala Leu Phe Met Phe Thr
            140                 145                 150 tgc cgt ggg att tta ggc tac tcc acc cag ctc cca ttg cct cag ggg      533
Cys Arg Gly Ile Leu Gly Tyr Ser Thr Gln Leu Pro Leu Pro Gln Gly
        155                 160                 165 ttt ttg ggc tcg ggt gtg gac ttc cct gtt ggg aac gtg tct ttt ttc      581
Phe Leu Gly Ser Gly Val Asp Phe Pro Val Gly Asn Val Ser Phe Phe
    170                 175                 180 ttg ttt ttt tct ggg cac gtt gca ggg tca gtg att gct tca ttg gac      629
Leu Phe Phe Ser Gly His Val Ala Gly Ser Val Ile Ala Ser Leu Asp
185                 190                 195                 200 atg agg agg atg cag agg tgg gaa ctg gct tgg act ttt gat gtg ctc      677
Met Arg Arg Met Gln Arg Trp Glu Leu Ala Trp Thr Phe Asp Val Leu
                205                 210                 215 aat gtt ttg caa gct gtg agg ttg ctg ggt aca aga ggc cat tac act      725
Asn Val Leu Gln Ala Val Arg Leu Leu Gly Thr Arg Gly His Tyr Thr
            220                 225                 230 att gat ttg gcc gta ggg gtt ggt gct gga att ctc ttt gat tct tta      773
Ile Asp Leu Ala Val Gly Val Gly Ala Gly Ile Leu Phe Asp Ser Leu
```

```
Ile Asp Leu Ala Val Gly Val Gly Ala Gly Ile Leu Phe Asp Ser Leu
            235                 240                 245 gct ggc aag tac gaa gat agc aaa agg aat ggt gct ctc aaa cac aat    821
Ala Gly Lys Tyr Glu Asp Ser Lys Arg Asn Gly Ala Leu Lys His Asn
250                 255                 260 ttg att gcg tga acaatgtgga tatagctaaa aaaattaaca aaccatcatg        873
Leu Ile Ala
265 gaaaagtaca catggaggtg taaaagtaaa agagtgagag ggcaagggtt tgaatcgtaa   933 aaaaaataag gtcaaagagt gatacatcat attattagga tttaggacaa gtcttaaatc   993 ttaattaccg cgtaatttta aatttgattt atttcactac tttttgtaac ctgttattat  1053 agtatagagt tttttttccc tactagtgga gtctgagttg gaattcactt gccaattgct  1113 atgatcccat gattgattgc tctaggtggg tgttgttccc                        1153

<210> SEQ ID NO 3
<211> LENGTH: 267
<212> TYPE: PRT
<213> ORGANISM: Soybean

<400> SEQUENCE: 3

Met Asn Gly Gly Ala Glu Ala Ser Leu Asn His Arg Arg Lys His Gln
1               5                   10                  15

Thr Ala Pro Ala Asp Gly Ala Lys Gly Val Lys Val Ala Asn Gly Ala
            20                  25                  30

Met Gly Lys Pro Ser Ser Ser Lys His Ser Cys Gly Ala Ser Phe Met
        35                  40                  45

Lys Trp Thr Val Ala Asp Ala Val His Val Val Thr His His Trp Met
50                  55                  60

Pro Cys Leu Phe Ala Leu Gly Leu Leu Phe Phe Met Ala Val Glu Tyr
65                  70                  75                  80

Thr Leu Leu Met Val Pro Pro Ser Ser Pro Pro Phe Asp Leu Gly Phe
                85                  90                  95

Ile Ala Thr Arg Ser Leu His Ala Leu Leu Glu Ser Ser Pro Asn Leu
            100                 105                 110

Asn Thr Leu Phe Ala Gly Leu Asn Thr Val Phe Val Gly Met Gln Thr
        115                 120                 125

Ser Tyr Ile Leu Trp Thr Trp Leu Ile Glu Gly Arg Pro Arg Ala Thr
    130                 135                 140

Ile Ser Ala Leu Phe Met Phe Thr Cys Arg Gly Ile Leu Gly Tyr Ser
145                 150                 155                 160

Thr Gln Leu Pro Leu Pro Gln Gly Phe Leu Gly Ser Gly Val Asp Phe
                165                 170                 175

Pro Val Gly Asn Val Ser Phe Phe Leu Phe Phe Ser Gly His Val Ala
            180                 185                 190

Gly Ser Val Ile Ala Ser Leu Asp Met Arg Arg Met Gln Arg Trp Glu
        195                 200                 205

Leu Ala Trp Thr Phe Asp Val Leu Asn Val Leu Gln Ala Val Arg Leu
    210                 215                 220

Leu Gly Thr Arg Gly His Tyr Thr Ile Asp Leu Ala Val Gly Val Gly
225                 230                 235                 240

Ala Gly Ile Leu Phe Asp Ser Leu Ala Gly Lys Tyr Glu Asp Ser Lys
                245                 250                 255

Arg Asn Gly Ala Leu Lys His Asn Leu Ile Ala
            260                 265
```

<210> SEQ ID NO 4
<211> LENGTH: 6321
<212> TYPE: DNA
<213> ORGANISM: Soybean
<220> FEATURE:
<221> NAME/KEY: Intron
<222> LOCATION: (3319)..(3514)
<223> OTHER INFORMATION: First intron
<220> FEATURE:
<221> NAME/KEY: Intron
<222> LOCATION: (3653)..(4079)
<223> OTHER INFORMATION: Second intron

<400> SEQUENCE: 4

```
caaaaatata ctcagatccg tttgtttaca aagatagata gtaaaaaaag aaaaggattg      60
aataataaaa tgacgtgaga ctcatttttta tattttactt taaatcaaaa attttatctt     120
tctatttttt tttctctgcc aaatcgaccc tggaagtgga gtgcaactaa ttttcactcc     180
gatcttcacc tcataaattt cgtccactcc tattgtgagt agaatgtgtt taatgtttaa     240
agccaaaaac gatcatgtgt gagtagaata tgttgctgta ttcttttttt gattttttt      300 ttctatttt aacttttgag gttatttttg caatactaca agaaaggtgg ccaatttctg      360
aaatttgaat cctaatcttg gtccaaccat ataatatata tatatagatg atattttat       420 tatttcctca ctagcattgc tttgcttctt tgtgaaattt actctgaagt gctgctatat     480 aattttggt aaaaggcagc attgtatttt gttcattgta actcttatat tattcaaagg      540
ttgttttgct gcccttttcg ttttgactca tgaatatttt gtcttccaat tccaaactat     600
actgctacat atgtattatt atttgcaatt tatcaaaagg ataaccaact tatcctttga     660
ttttttttgc cttgtatgat ggtcatgttt accgtctttc cttgagaggg tcatagactt     720
agcgttcttt gttgaagaga taggttcgtc tcttggctag gtagttttgt tgcgtaaaat     780
ttttcaatgg ctcactttgt ctgtggatta tgggtacatg catgttttta attcttttgag    840 atgtcctgtt gacaaactta ttgttggggt tcaacttgta ggcacacgtg catggtggaa     900
aagtgactga tttgtcattg tcccaataga tgattaatcg attagtatgt gcatctaatg     960
tttttcataa ttaaataata tttggtaatt atccaaattt tttcatcttt actcattttt   1020 cactttatt ttttaatttt attcaccatc ctgcaataga gatttgatt gcgagatttg     1080 aaaattatt accattttga ttcttcttat aacaaatcta cggtttgatc aaattttgtg    1140
aaataatttt agcattttt aaaaaatcaa tatattgtta cttgtgaatg aaaatgtagg    1200
ttattatcaa cgagggttac ttctctatat actcattcat aaaatcaaac tactaccaac    1260
atatttgaga actatttatt tacctagttt gatgaacttt gttgattcat acagaagtta   1320
ttaatgaatg tatattcttt catcaaccct tatgtaaaaa ataatgtaat catattatga    1380
agtaaaaaat ggatcgatac ataaaagaaa gcacttgaat attgtatcgg aatttattgt    1440
tgtatttctt gtaatttgtt gtatatatat ataagagtac aagaatctgt atactaattg    1500
cctataattg tctagtctat aattgcctat aatagaaatc ctatacaatg atataattgc    1560
ctatgataga aatcctatt aaatataatt atgatacgtt gcctataatt gccgttagtg    1620
aggtcaattt tagtgccacg tggactatcc acgtggcact aaaggatgac gtgacatgac    1680
acgtggacgt gtctgatgcc acgtcatttg atgataacaa aatgagtaaa tagacaattt   1740
agtccctaac tttgtacccc tgttgcatat tagtccctaa cttaatgaaa aattcaaaat   1800
agtctctatc ttttacataa gtattgcaaa atagtccttc cgttaaattt taaagtaatg   1860
```

```
ttgttagtaa gttcaatttt agtatcacgt catttgatga tgatagaatg agtgacttct    1920
tcaaatttga tggttttaaa ccaattgagg catatatacg aaaaagaact cacacacact    1980
tgcacaaata aaagaacca aaaatccaca gcaacaacct tatctctgta gctgtcaaca     2040
ccaatgggcg aggtctgcat aaccattctc ttttcctctt tttttactt caattaccat     2100 caatgtatca tcttgggttc tgattttttt tgtgtgtttt gaataggaag agaaaaaacc    2160
agaggaaaac aaagtggagg agaaaaaagc aaatgaagaa gaaaagaaag aagaagagaa    2220
aaaaccagaa gaatcaaaag atgacaagga atccaaggag gaatctgcgc tgtcagaaat    2280
cgtgctaggc acaacctttg caatgcatgg acactttaag catgatttct gacatctttt    2340
aagttaggga ttatttttgca acacttatgc aaaagatagg gactattttg aattttttcat 2400 taagttaggg actaatatac aacaggggta caaagtcagg gactaaatta cctatttact   2460
tgttttgtta tcatcaaatg tcgtggcatc agcacgtcca cgtgtcatgc cacgtcatcc    2520
tttagaactt aacggcgtta ctttaaaact taacggaagg actattttgc aacacttata   2580
caaagatagg gactatttta aatttaatat taaattaggt actaatatat aaaatgggta   2640
taatctcaga gactaaattg tctattcact gtattcgcaa ttctcataat cttccctgtg   2700
cggctgtgcg tgtaaataac catagagaat cacacccaca tcacatgcaa tgcaagacta   2760 attaccccctt tgcattttt tattcttaaa aaagaaaaa aataggaaaa ttaccaaaaa    2820
agaaaacttc gtagtcctag aaacgtaaaa ccaacctcaa cctaacatgg gaaactccgt   2880
caccactttc cctcttccga tttttatatc attcgccaca tccattatta tgtcgtccgc   2940
acttaaaaaa aacgatctcc aacggtcatg aacggcggcg ctgaggcctc cgtcaatcac    3000
aggcgcagac accaagcagc ttccgctaac ggcgttaaga tagcaaacgg ggccatggcg    3060
aagccgtcct cgacgctctg ctacgacgcc tcgttcatga aatggaccgt ggcggatgct    3120
gtccacgtgg cgacgcatca ttggatgccg tgcttattcg cattagggct tctcttcttc    3180
atggccgtga aatacacgct cctcatggtt ccgccgtcgt cgccgccttt cgatctgggc    3240
ttcattgcca cgcgttccct ccacgcactc ctcgagtcat cgccgaatct caacacgctc    3300
ttcgccgggc tcaatacggt acgtcgttta cactttctcc agatctgaac gaatcgggac    3360 acttttttt tctggtttcg gatttcgttg tgggcaattg ggagatcgaa tttgtttgga    3420
ggaaatgcaa atgggttggt ctcaaaatct gatcttttta ctgctttttt ggttttagta    3480
ttcattttgc attaatgggt tttgacatgg ataggtgttt gtgggatgc aaacgagtta     3540 tatcttatgg acgtggctga ttgaaggacg ccccagagcc acgatttcag cattgttcat    3600
gttcacatgc cgtggaattt tagggtactc cacccagctc ccattgcctc aggtgattca    3660
ttacttcatc aaccaaagtt tcaattttt tcattatttt aatctttttt tattactacc     3720
tacccaggat tttttatacc ttcattcaat gactttaaa tgttatcata ttttttattg     3780
aataacgttg taaatctttt tatagattaa actattcact tgctctctat gtttattctc    3840
ttttaagttt tggtccttta ccaaaaaaaa aaaactcta atttagtct gtatgccaag      3900 ttttatagca atcttatacg aaaagagtca tatctagtga tagcaatgga ccaaaactta   3960
actaacatgc aggtttagtg actaaatctc tatttttct gatataggaa ctaaaaccat    4020
aacttttttt tatacaatgt ataaaaatta aactaattta tttatttggt gttgaacagg    4080
gattttgggg ctcgggtgtg gatttcccag ttgggaacgt gtcgttttc ttgtttttt      4140 cggggcatgt tgcgggttca gtgattgctt ccttggacat gaggaggatg cagaggtggg    4200
aactggcttg gacttttgat gtgctcaatg ttttgcaagc tgtgaggttg ctgggtacaa    4260
```

```
gaggacatta cactattgat ttggccgtag gggttggtgc tggaattctc tttgattctt    4320
tagctggcaa gtacgaagat agcaaaagga atgctgctct atccacaacc cacagagcac    4380
aatttgattg cgtcaacaat gtggatatag ctaaaaaaat taacaaatga tcatggaaaa    4440
gtacacatgg agtgtaaaag tacaagggtg agtgagaggg caagagtctg aattgtaaaa    4500
aagataagaa aaggtcagag agtgatatat atcattatta ggagtagtct taaatcttaa    4560
ttaccgcgta attttaaatc tgatttattt tagtttttat aacctgttat tatagtggag    4620
tctaggttgg aattcggttg ccatgatccc atgattgatt gctctgggtg ttgttcccac    4680
tttgtggacg gcagtgcgtg ttaaaggatg ttgattgtaa catcaaattt taagatttta    4740
ttttagttga ttcatagtca ttggagaact atgactgcat taaattttga tttgatttga    4800
ttttaatttg aatataatgg ttattatgca agtttccttt tctttggtcc ccaaagacaa    4860
atcggatgga caaatgcgaa aattccacca aattcaaact atacaagaaa atctgaaact    4920
tatgagctgg ttaagaaaat tccttcccat gaatgaaatc gcagtagagc tcattgatcg    4980
gtgccacttt acccaagcat gtactagtag taaattgtag ttttggtaat attattagtt    5040
tagtccgttg ggattagatt caactttta caaaatcaat tctaattcca cgttgaatgt    5100
caaaaacatc aaatactagt tgtttttatt ttttcagttt ttcaccatga ttttgagggt    5160
cagaatcaat tcttgtaatt atccaaacac actgtatgta acttttctc aaataaatta    5220 cactttcaac tagacaagga aagagaaaaa cttgtttcta tagtaacaga ttaaggagag    5280
aaataaggta acaagaccag caattgccta tgtccaatgt tgagagtgga atttacaata    5340
tacactgtgt acttaaaacc aacataaagt atgatcgaaa tgaatattta tgcaaagtat    5400
aatgctattc ttcagactca atccaattca attgtacatg ttccatcatc tacattggct    5460
agcgggttgt acaggtgcga actaggatct gtgcatccta aaacaaaatt cagatcgcag    5520
cgatcaccct gcatggatgt tctcattcat cattaagaaa gtgacagtgt tccaaggaga    5580
agcaatgatt taaagagtaa agaaattgaa gaatttactc accccttctt ttgacaaatt    5640
accaatcata gcacatttgg ttataatttt atttgtgtct ggaaatattg cttgctcaca    5700
tgctccttct ttactcagtt cctcagccaa gccctaccac aatagtacac ccaattcagg    5760
gtcatgttaa ctaatactct aaaagattcc attgttgtac ttttggtttc tttaataact    5820
catcagtgtc aaaattgatg tactaaattc tcacaagctc gaatatactt gtcttgtaat    5880
gctgtcttat aaaaacaata ggtagaactc attcttcact acttgactaa tgttttcttt    5940
tggggctaaa ctatatagct ttgccaacaa cctccttta gaatgaaaaa tttagtaatc    6000
ttaaaatcaa atatgaaact atcaaacata tatgggcctt taattcacag atctacaagt    6060
gctgcctttg cttttatctt atttcctcaa aagacagatt gagagtttga ttataaagct    6120
agaatgactt ttgtattaag ctagaaattg tgtggctggc tatttacctt attaaagaag    6180
tcaattggct tgttttgtaa tgccttggga acttgaaact gtagtctata tggaccatcc    6240
cagtctactc catttgtaaa tgaaaagatc aagttcaaag ctgcacaaaa aagagaagtt    6300
agcaagaaaa aactgaatga t                                              6321
```

<210> SEQ ID NO 5
<211> LENGTH: 1580
<212> TYPE: DNA
<213> ORGANISM: Soybean
<220> FEATURE:
<221> NAME/KEY: CDS
<222> LOCATION: (342)..(1181)

<400> SEQUENCE: 5

```
atataaaatg ggtataatct cagagactaa attgtctatt cactgtattc gcaattctca      60
taatcttccc tgtgcggctg tgcgtgtaaa taaccataga gaatcacacc cacatcacat     120
gcaatgcaag actaattacc cctttgcatt tttttattct taaaaaaaga aaaaatagg      180 aaaattacca aaaagaaaa cttcgtagtc ctagaaacgt aaaaccaacc tcaacctaac      240
atgggaaact ccgtcaccac tttccctctt ccgattttta tatcattcgc cacatccatt     300
attatgtcgt ccgcacttaa aaaaaacgat ctccaacggt c atg aac ggc ggc gct     356
                                              Met Asn Gly Gly Ala
                                              1               5 gag gcc tcc gtc aat cac agg cgc aga cac caa gca gct tcc gct aac      404
Glu Ala Ser Val Asn His Arg Arg Arg His Gln Ala Ala Ser Ala Asn
            10                  15                  20 ggc gtt aag ata gca aac ggg gcc atg gcg aag ccg tcg tcg acg ctc      452
Gly Val Lys Ile Ala Asn Gly Ala Met Ala Lys Pro Ser Ser Thr Leu
        25                  30                  35 tgc tac gac gcc tcg ttc atg aaa tgg acc gtg gcg gat gct gtc cac      500
Cys Tyr Asp Ala Ser Phe Met Lys Trp Thr Val Ala Asp Ala Val His
    40                  45                  50 gtg gcg acg cat cat tgg atg ccg tgc tta ttc gca tta ggg ctt ctc      548
Val Ala Thr His His Trp Met Pro Cys Leu Phe Ala Leu Gly Leu Leu
55                  60                  65 ttc ttc atg gcc gtg gaa tac acg ctc ctc atg gtt ccg ccg tcg tcg      596
Phe Phe Met Ala Val Glu Tyr Thr Leu Leu Met Val Pro Pro Ser Ser
70                  75                  80                  85 ccg cct ttc gat ctg ggc ttc att gcc acg cgt tcc ctc cac gca ctc      644
Pro Pro Phe Asp Leu Gly Phe Ile Ala Thr Arg Ser Leu His Ala Leu
                90                  95                 100 ctc gag tca tcg ccg aat ctc aac acg ctc ttc gcc ggg ctc aat acg      692
Leu Glu Ser Ser Pro Asn Leu Asn Thr Leu Phe Ala Gly Leu Asn Thr
            105                 110                 115 gtg ttt gtg ggg atg caa acg agt tat atc tta tgg acg tgg ctg att      740
Val Phe Val Gly Met Gln Thr Ser Tyr Ile Leu Trp Thr Trp Leu Ile
        120                 125                 130 gaa gga cgc ccc aga gcc acg att tca gca ttg ttc atg ttc aca tgc      788
Glu Gly Arg Pro Arg Ala Thr Ile Ser Ala Leu Phe Met Phe Thr Cys
    135                 140                 145 cgt gga att tta ggg tac tcc acc cag ctc cca ttg cct cag gga ttt      836
Arg Gly Ile Leu Gly Tyr Ser Thr Gln Leu Pro Leu Pro Gln Gly Phe
150                 155                 160                 165 ttg ggc tcg ggt gtg gat ttc cca gtt ggg aac gtg tcg ttt ttc ttg      884
Leu Gly Ser Gly Val Asp Phe Pro Val Gly Asn Val Ser Phe Phe Leu
                170                 175                 180 ttt ttt tcg ggg cat gtt gcg ggt tca gtg att gct tcc ttg gac atg      932
Phe Phe Ser Gly His Val Ala Gly Ser Val Ile Ala Ser Leu Asp Met
            185                 190                 195 agg agg atg cag agg tgg gaa ctg gct tgg act ttt gat gtg ctc aat      980
Arg Arg Met Gln Arg Trp Glu Leu Ala Trp Thr Phe Asp Val Leu Asn
        200                 205                 210 gtt ttg caa gct gtg agg ttg ctg ggt aca aga gga cat tac act att     1028
Val Leu Gln Ala Val Arg Leu Leu Gly Thr Arg Gly His Tyr Thr Ile
    215                 220                 225 gat ttg gcc gta ggg gtt ggt gct gga att ctc ttt gat tct tta gct     1076
Asp Leu Ala Val Gly Val Gly Ala Gly Ile Leu Phe Asp Ser Leu Ala
230                 235                 240                 245 ggc aag tac gaa gat agc aaa agg aat gct gct cta tcc aca acc cac     1124
Gly Lys Tyr Glu Asp Ser Lys Arg Asn Ala Ala Leu Ser Thr Thr His
```

```
                    250                 255                 260
aga gca caa ttt gat tgc gtc aac aat gtg gat ata gct aaa aaa att     1172
Arg Ala Gln Phe Asp Cys Val Asn Asn Val Asp Ile Ala Lys Lys Ile
        265                 270                 275 aac aaa tga tcatggaaaa gtacacatgg agtgtaaaag tacaagggtg             1221
Asn Lys agtgagaggg caagagtctg aattgtaaaa aagataagaa aaggtcagag agtgatatat   1281
atcattatta ggagtagtct taaatcttaa ttaccgcgta attttaaatc tgatttattt   1341 tagttttat aacctgttat tatagtggag tctaggttgg aattcggttg ccatgatccc    1401
atgattgatt gctctgggtg ttgttccac tttgtggacg gcagtgcgtg ttaaaggatg    1461
ttgattgtaa catcaaattt taagatttta ttttagttga ttcatagtca ttggagaact   1521
atgactgcat taaattttga tttgatttga ttttaatttg aatataatgg ttattatgc    1580
```

<210> SEQ ID NO 6
<211> LENGTH: 279
<212> TYPE: PRT
<213> ORGANISM: Soybean

<400> SEQUENCE: 6

```
Met Asn Gly Gly Ala Glu Ala Ser Val Asn His Arg Arg His Gln
1               5                   10                  15

Ala Ala Ser Ala Asn Gly Val Lys Ile Ala Asn Gly Ala Met Ala Lys
            20                  25                  30

Pro Ser Ser Thr Leu Cys Tyr Asp Ala Ser Phe Met Lys Trp Thr Val
            35                  40                  45

Ala Asp Ala Val His Val Ala Thr His His Trp Met Pro Cys Leu Phe
50                  55                  60

Ala Leu Gly Leu Leu Phe Phe Met Ala Val Glu Tyr Thr Leu Leu Met
65                  70                  75                  80

Val Pro Pro Ser Ser Pro Phe Asp Leu Gly Phe Ile Ala Thr Arg
                85                  90                  95

Ser Leu His Ala Leu Leu Glu Ser Ser Pro Asn Leu Asn Thr Leu Phe
            100                 105                 110

Ala Gly Leu Asn Thr Val Phe Val Gly Met Gln Thr Ser Tyr Ile Leu
            115                 120                 125

Trp Thr Trp Leu Ile Glu Gly Arg Pro Arg Ala Thr Ile Ser Ala Leu
            130                 135                 140

Phe Met Phe Thr Cys Arg Gly Ile Leu Gly Tyr Ser Thr Gln Leu Pro
145                 150                 155                 160

Leu Pro Gln Gly Phe Leu Gly Ser Gly Val Asp Phe Pro Val Gly Asn
                165                 170                 175

Val Ser Phe Phe Leu Phe Phe Ser Gly His Val Ala Gly Ser Val Ile
            180                 185                 190

Ala Ser Leu Asp Met Arg Arg Met Gln Arg Trp Glu Leu Ala Trp Thr
            195                 200                 205

Phe Asp Val Leu Asn Val Leu Gln Ala Val Arg Leu Leu Gly Thr Arg
            210                 215                 220

Gly His Tyr Thr Ile Asp Leu Ala Val Gly Val Gly Ala Gly Ile Leu
225                 230                 235                 240

Phe Asp Ser Leu Ala Gly Lys Tyr Glu Asp Ser Lys Arg Asn Ala Ala
                245                 250                 255
```

```
Leu Ser Thr Thr His Arg Ala Gln Phe Asp Cys Val Asn Asn Val Asp
            260                 265                 270

Ile Ala Lys Lys Ile Asn Lys
        275
```

SOYBEAN ROD1 GENE SEQUENCES AND USES THEREOF

CROSS REFERENCE TO RELATED APPLICATIONS

This application claims the benefit of U.S. Provisional Application Ser. No. 61/669,703, filed Jul. 10, 2012 and European Patent Application Ser. No. 12175304.0, filed Jul. 6, 2012, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS12-2012_ST25sequence listing," created on Jul. 16, 2013, and having a size of 32 kilobytes and is filed concurrently with the specification. The sequence listing contained in this ASCII formatted document is part of the specification and is herein incorporated by reference in its entirety.

FIELD OF THE INVENTION

The invention relates to the field of agronomy. Methods and means are provided to modulate fatty acid composition in Soybeans, such as to increase levels of unsaturated fatty acids in soybeans by modulation of expression of ROD1 genes in various manners, including provision of knock-out ROD1 alleles or providing inhibitory RNAs to the ROD1 genes.

BACKGROUND OF THE INVENTION

Many plant species store triacylglycerols (TAGs) in their seeds as a carbon reserve. These TAGs are the major source of energy and carbon material that supports seedling development during the early stages of plant life. Vegetable oils from soybean (*Glycine max*), Brassica (*Brassica napus* or *B. rapa*), sunflower (*Helianthus annuus*) and many other oilseed crops are also an important source of oil for the human diet or industrial applications including, but not limited to biofuels, biolubricants, nylon precursors, and detergent feedstocks. The degree and/or amount of polyunsaturated fatty acids of vegetable oils are characteristic and determinative properties with respect to oil uses in food or non-food industries. More specifically, the characteristic properties and utilities of vegetable oils are largely determined by their fatty acyl compositions in TAG.

Major vegetable oils are comprised primarily of palmitic (16:0), stearic (18:0), oleic (18:1cis $\Delta^9$), linoleic (18:2cis $\Delta^{9,12}$), and α-linolenic (18:3cis $\Delta^{9,12,15}$ or C18:3) acids. Palmitic and stearic acids are, respectively, 16 and 18 carbon-long, saturated fatty acids. Oleic, linoleic, and linolenic acids are 18-carbon-long, unsaturated fatty acids containing one, two, and three double bonds, respectively. Oleic acid is referred to as a monounsaturated fatty acid, while linoleic and linolenic acids are referred to as polyunsaturated fatty acids. Modifications of the fatty acid compositions have been sought after for at least a century in order to provide optimal oil products for human nutrition and chemical (e.g., oleochemical) uses (Gunstone, 1998, Prog Lipid Res 37:277; Broun et al., 1999, Annu Rev Nutr 19:107; Jaworski et al, 2003, Curr Opin Plant Biol 6:178). In particular, the polyunsaturated fatty acids (18:2 and 18:3) have received considerable attention because they are major factors that affect nutritional value and oil stability. However, while these two fatty acids provide essential nutrients for humans and animals, they increase oil instability because they comprise multiple double bonds that may be easily oxidized during processing and storage.

The desaturation of 18:1 into 18:2 is a critical step for synthesizing polyunsaturated fatty acids. During storage lipid biosynthesis, this reaction is known to be catalyzed by the fatty acid desaturase, FAD2, a membrane-bound enzyme located on the endoplasmic reticulum (ER) (Browse and Somerville, 1991, Annu Rev Plant Physiol Plant Mol Biol 42:467). The FAD2 substrate 18:1 must be esterified on the sn-2 position of phosphatidylcholine (PC) (Miguel and Browse, 1992, J Biol Chem 267:1502; Okuley et al., 1994, Plant Cell 6:147), which is the major membrane phospholipid of plant cells. Not surprisingly, therefore, down-regulation of FAD2 (and FAD3) genes has become a preferred strategy for avoiding the need to hydrogenate vegetable oils and the concomitant production of undesirable trans fatty acids. For example, soybean has both seed-specific and constitutive FAD2 desaturases, so that gene silencing of the seed-specific isoform has allowed the production of high-oleate cultivars (>88% 18:1 in the oil) in which membrane unsaturation and plant performance are largely unaffected. Significantly, however, such FAD2 gene-silencing strategies are substantially limited because, for example, canola and other oilseed plants have only constitutive FAD2 enzymes. Therefore, in canola and other such constitutive FAD2 crops, silencing or down-regulation of FAD2 not only alters the fatty acid composition of the storage triacylglycerol (TAG) in seeds, but also of the cellular membranes, which severely compromises growth and yield of the plant. For example, the defective FAD2 in the *Arabidopsis* mutant fad2 alters fatty acid compositions of seeds as well as vegetable tissues, and severely compromises plant growth (Browse and Somerville, supra). FAD2 mutations and silencing that produce the highest 18:1 levels in the oil also reduce membrane unsaturation in vegetative and seed tissues, resulting in plants that germinate and grow poorly. As a result, only partial downregulation of FAD2 expression is possible, producing approximately 70-75% 18:1 in the oil of commercial cultivars such as Nexera/Natreon (Dow AgroSciences) and Clear Valley 75 (Cargill).

Lu et al (2009, Proc Natl Acad Sci USA 106:18837) and WO2009/111587 describe the identification of phosphatidylcholine:diacylglycerol cholinephosphotransferase (PDCT) from *Arabidopsis*, which is endoced by the ROD1 gene, which is involved in the transfer of 18:1 into phosphatidylcholine for desaturation and also for the reverse transfer of 18:2 and 18:3 into the triacylglycerol synthesis pathway. The PDCT enzyme catalyzes transfer of 18:2 and 18:3 into the triacylglycerol synthesis pathway. Seeds of an *Arabidopsis* rod1 mutant have a decrease in 18:2 and 18:3 polyunsaturated fatty acids and a concomitant increase in 18:1 relative to wild-type, whereas there is no effect on the fatty acid compositions of leaf or root tissues. identified in *Arabidopsis*. WO2009/111587 further describes ROD1 homologs from *Brassica napus, Brassica rapa*, and *Brassica oleracea*.

In order to use the ROD1 gene to increase 18:1 levels and reduce 18:2 and 18:3 levels in soybean, a need remains for knowing all ROD1 gene sequences and the functionality of the encoded proteins in the soybean genome. The isolation of mutant alleles corresponding to rod1 in soybeans may be complicated by the polyploid history and consequent possibility of the presence of multiple copies of the ROD1 gene.

Thus, the prior art is deficient in teaching the ROD1 gene sequences and the number of ROD1 genes in soybean, and which of the ROD1 genes encode a functional protein or need to be inactivated in order to increase the levels of 18:1 in soybeans. As described hereinafter, this problem has been solved, allowing to modulate expression of PDCT with the aim to modulate the 18:1 levels in soybeans, as will become apparent from the different embodiments and the claims.

SUMMARY OF THE INVENTION

It is a first embodiment of the invention to provide a soybean plant or plant cell, part, seed or progeny thereof, comprising at least one ROD1 gene, characterized in that at least one ROD1 gene is an inactivated or a knock-out rod1 gene. In a further embodiment, said plant comprises two knock-out rod1 genes. In yet a further embodiment, said knock-out gene is a knock-out allele of the ROD1 gene encoding a protein having at least 90% sequence identity to SEQ ID No. 3 or SEQ ID No. 6. In a further embodiment, said soybean plant is homozygous for said knock-out rod1 gene.

In a further embodiment, a transgenic soybean plant is provided comprising a chimeric gene, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells. In another embodiment, said RNA molecule is inhibitory to a ROD1 gene encoding a protein having at least 90% sequence identity to SEQ ID No. 3 or SEQ ID No. 6.

In a further embodiment, seeds are provided from the plants according to the invention, i.e. plants comprising a knock-out ROD1 gene or an RNA inhibitory to a ROD1 gene. In yet another embodiment, oil from the seeds of the plants according to the invention is provided.

In another embodiment, a method is provided for increasing the C18:1 levels in soybean seed oil, comprising modulating the expression of a ROD1 gene. In yet another embodiment, a method is provided for increasing the C18:1 levels in soybean seed oil, comprising the steps of introducing or providing an chimeric gene to a soybean plant cell, to create transgenic cells, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells; and regenerating transgenic plants from said transgenic cells.

In again another embodiment, a method is provided for increasing the C18:1 levels in seed oil, comprising the steps of treating seeds or plant material with a mutagenic chemical substance or with ionizing radiation; identifying plants with a mutated ROD1 gene, wherein the ROD1 gene, prior to being mutated, encodes a polypeptide having at least 90% sequence identity to SEQ ID No. 3 or to SEQ ID No. 6; and selecting a plant with an increased level of C18:1 in the seeds compared to a plant in which the ROD1 gene is not mutated.

In a further embodiment, a method is provided for obtaining a soybean plant with increased levels of C18:1 in the seeds comprising the step of introducing a knock-out allele of a ROD1 gene in said soybean plant, and selecting said soybean plant with increased levels of C18:1 levels in the seeds for the presence of said knock-out allele of a ROD1 gene by analyzing genomic DNA from said plant for the presence of at least one molecular marker, wherein said at least one molecular marker is linked to said knock-out allele of a ROD1 gene.

In another embodiment, a method is provided to determine the presence or absence of a knock-out allele of a ROD1 gene in a biological sample, comprising providing genomic DNA from said biological sample, and analyzing said DNA for the presence of at least one molecular marker, wherein the at least one molecular marker is linked to said knock-out allele of a ROD1 gene.

Yet another embodiment provides a kit for the detection of a knock-out allele of a ROD1 gene in soybean DNA samples, wherein said kit comprises one or more PCR primer pairs, which are able to amplify a DNA marker linked to said knock-out allele of a ROD1 gene.

In a further embodiment, a method is provided for determining the zygosity status of a mutant ROD1 allele in a soybean plant, or a cell, part, seed or progeny thereof, comprising determining the presence of a mutant and/or a corresponding wild type ROD1 specific region in the genomic DNA of said plant, or a cell, part, seed or progeny thereof.

Yet a further embodiment provides method for transferring at least one knock-out ROD1 allele from one soybean plant to another soybean plant comprising the steps of: identifying a first soybean plant comprising at least one knock-out ROD1 allele; crossing the first soybean plant with a second soybean plant not comprising the at least one knock-out ROD1 allele and collecting F1 seeds from the cross; optionally, identifying F1 soybean plants comprising the at least one knock-out ROD1 allele; backcrossing F1 soybean plants comprising the at least one knock-out ROD1 allele with the second plant not comprising the at least one knock-out ROD1 allele for at least one generation (x) and collecting BCx seeds from the crosses; identifying in every generation BCx soybean plants comprising the at least one knock-out ROD1 allele by analyzing genomic DNA of said BCx plants for the presence of at least one molecular marker, wherein the at least one molecular marker is linked to said knock-out ROD1 allele.

Another embodiment provides a chimeric gene comprising the following operably linked elements: a plant-expressible promoter; a DNA region, which when transcribed yields an RNA molecule inhibitory to at least one ROD1 gene, said ROD1 gene encoding a protein having at least 90% sequence identity to SEQ ID No. 3 or SEQ ID No. 6; and optionally a transcription termination and polyadenylation region functional in plant cells.

In again another embodiment, a knock-out allele of an ROD1 gene is provided, wherein the knock-out ROD1 allele is a mutated version of the native ROD1 gene selected from the group consisting of: a nucleic acid molecule which comprises at least 90% sequence identity to SEQ ID No. 1 or SEQ ID No. 4; or a nucleic acid molecule encoding an amino acid sequence comprising at least 90% sequence identity to SEQ ID No. 3 or SEQ ID No. 6, wherein said mutant rod1 allele comprises a mutated DNA region consisting of one or more inserted, deleted or substituted nucleotides compared to a corresponding wild-type DNA region in the functional ROD1 gene and wherein said mutant rod1 allele encodes no functional ROD1 protein or encodes a ROD1 protein with reduced activity.

In a further embodiment, a method is provided for producing oil, comprising harvesting seeds from the plants according to the invention, i.e. soybean plants comprising an inactivated or a knock-out ROD1 gene or an RNA inhibitory to a ROD1 gene, and extracting the oil from said seeds.

In yet a further embodiment, a method is provided of producing food or feed, such as oil, meal, grain, starch, flour or protein, or an industrial product, such as biofuel, fiber, industrial chemicals, a pharmaceutical or a neutraceutical, comprising obtaining the soybean plant or a part thereof according to the invention, and preparing the food, feed or industrial product from the plant or part thereof.

GENERAL DEFINITIONS

A "ROD1 gene" or "ROD1 allele", as used herein, is a gene or allele comprising a sequence having at least 55% sequence identity to the coding sequence of the ROD1 gene of *Arabidopsis thaliana*, as described in WO2009/111587.

A ROD1 gene or ROD1 allele can, but does not need to encode a functional ROD1 protein. Functionality of the ROD1 protein can be tested, for example, in yeast as described in example 4 or as described by Lu et al. (2009) Proc Natl Acad Sci USA 106:18839.

A "knock-out rod1 gene" or "knock-out rod1 allele" as used herein is a rod1 gene or a rod1 allele which encodes no functional ROD1 protein, or which encodes a ROD1 protein with reduced activity. Said "knock-out rod1 gene" can be a full knock-out rod1 gene, encoding no functional ROD1 protein, or can be a partial knock-out rod1 gene, encoding a ROD1 protein with reduced activity. Said "knock-out rod1 gene" or "knock-out rod1 allele" can be a mutant rod1 allele or a mutant rod1 gene, which may encode no functional ROD1 protein, or which may encode a mutant ROD1 protein with reduced activity. The gene or allele may also be referred to as an inactivated gene or allele.

A "functional ROD1 gene" or "functional ROD1 allele" as used herein is a ROD1 gene or a ROD1 allele which encodes a functional ROD1 protein.

A "mutant rod1 gene" or "mutant rod1 allele" as used herein refers to any rod1 gene or rod1 allele which is not found in plants in the natural population or breeding population, but which is produced by human intervention such as mutagenesis or gene targeting. A mutant rod1 allele comprises knock-out rod1 alleles, and functional rod1 alleles.

Functional ROD1 protein is a ROD1 protein which has at least 5%, or at least 10%, or at least 15%, or at least 20%, or at least 25%, or at least 30% of the activity of the protein encoded by the *Arabidopsis* ROD1 gene as described in WO2009/111587, as tested, for example, in yeast as described in example 3.

A mutant ROD1 protein with reduced functionality is a ROD1 protein encoded by a mutant rod1 gene which has reduced activity as compared to the corresponding wild-type ROD1 protein encoded by the wild-type ROD1 gene. Said activity may be reduced with at least 10%, or at least 20%, or at least 30%, or at least 40%, or at least 50%, or at least 60%, or at least 70%, or at least 80%, or at least 90%.

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence within a plant cell, e.g. an endogenous allele of an ROD1 gene present within the nuclear genome of a soybean cell. An "isolated nucleic acid sequence" is used to refer to a nucleic acid sequence that is no longer in its natural environment, for example in vitro or in a recombinant bacterial or plant host cell.

The term "gene" means a DNA sequence comprising a region (transcribed region), which is transcribed into an RNA molecule (e.g. into a pre-mRNA, comprising intron sequences, which is then spliced into a mature mRNA, or directly into a mRNA without intron sequences) in a cell, operably linked to regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. "Endogenous gene" is used to differentiate from a "foreign gene", "transgene" or "chimeric gene", and refers to a gene from a plant of a certain plant genus, species or variety, which has not been introduced into that plant by transformation (i.e. it is not a "transgene"), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (polypeptide), and translation termination by translation stop codons. The term "functionally expressed" is used herein to indicate that a functional protein is produced; the term "not functionally expressed" to indicate that a protein with significantly reduced or no functionality (biological activity) is produced or that no protein is produced (see further below).

The terms "protein" or "polypeptide" are used interchangeably and refer to molecules consisting of a chain of amino acids, without reference to a specific mode of action, size, 3-dimensional structure or origin. A "fragment" or "portion" of an ROD1 protein may thus still be referred to as a "protein". An "isolated protein" is used to refer to a protein that is no longer in its natural environment, for example in vitro or in a recombinant bacterial or plant host cell.

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In amphidiploid species, essentially two sets of diploid genomes exist, whereby the chromosomes of the two genomes are referred to as "homeologous chromosomes" (and similarly, the loci or genes of the two genomes are referred to as homeologous loci or genes). A diploid, or amphidiploid, plant species may comprise a large number of different alleles at a particular locus.

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

As used herein, the term "locus" (loci plural) means a specific place or places or a site on a chromosome where for example a gene or genetic marker is found.

"Wild type" (also written "wildtype" or "wild-type"), as used herein, refers to a typical form of a plant or a gene as it most commonly occurs in nature. A "wild type plant" refers to a plant in the natural population or in a breeding population. A "wild type allele" refers to an allele of a gene occurring in wild-type plants.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the fruit dehiscence properties), such as seed obtained by selfing or crossing, plants and plant parts derived there from are encompassed herein, unless otherwise indicated.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

"Mutagenesis", as used herein, refers to the process in which plant cells (e.g., a plurality of seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), T-DNA insertion mutagenesis (Azpiroz-Leehan et al. (1997) Trends Genet 13:152-156), transposon mutagenesis (McKenzie et al. (2002) Theor Appl Genet 105:23-33), or tissue culture mutagenesis (induction of somaclonal variations), or a combination of two or more of these. Thus, the desired mutagenesis of one or more ROD1 alleles may be accomplished by one of the above methods. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, plants are regenerated from the treated cells using known techniques. For instance, the resulting seeds may be planted in accordance with conventional growing procedures and following self-pollination seed is formed on the plants. Additional seed that is formed as a result of such self-pollination in the present or a subsequent generation may be harvested and screened for the presence of mutant rod1 alleles. Several techniques are known to screen for specific mutant alleles, e.g., Deleteagene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant rod1 alleles are described in the Examples below.

The term "gene targeting" refers herein to directed gene modification that uses mechanisms such as homologous recombination, mismatch repair or site-directed mutagenesis. The method can be used to replace, insert and delete endogenous sequences or sequences previously introduced in plant cells. Methods for gene targeting can be found in, for example, WO 2006/105946 or WO2009/002150. Gene targeting can be used to create mutant rod1 alleles, such as knock-out rod1 alleles.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Substantially identical" or "essentially similar", as used herein, refers to sequences, which, when optimally aligned as defined above, share at least a certain minimal percentage of sequence identity (as defined further below).

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (T$_m$) for the specific sequences at a defined ionic strength and pH. The T$_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 μg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

DETAILED DESCRIPTION

The current invention is based on the identification of two ROD1 genes in soybean (*Glycine max*).

It is a first embodiment of the invention to provide a soybean plant or plant cell, part, seed or progeny thereof, comprising at least one ROD1 gene, characterized in that at least one ROD1 gene is an inactivated or a knock-out rod1 gene. Said at least one ROD1 gene can be, for example, one ROD1 gene, or two ROD1 genes, or at least two ROD1 genes. In a further embodiment, said plant comprises two knock-out rod1 genes. In yet a further embodiment, said knock-out gene is a knock-out allele of the ROD1 gene encoding a protein having at least 90% sequence identity to SEQ ID No. 3 or SEQ ID No. 6. In a further embodiment, said soybean plant is homozygous for said knock-out rod1 gene.

At least 90% sequence identity as used herein can be at least 90% sequence identity, or at least 95% sequence identity, or at least 98% sequence identity, or can be 100% sequence identity.

A knock-out allele of the ROD1 gene encoding a protein having at least 90% sequence identity to SEQ ID No. 3 or to SEQ ID No. 6 can be a knock-out allele of the ROD1 gene having at least 90% sequence identity, or at least 95% sequence identity, or at least 98% sequence identity, or having 100% sequence identity to SEQ ID No. 1, SEQ ID No. 4, respectively.

Said knock-out allele of said ROD1 gene can be a mutant ROD1 gene comprising one or more nucleotide deletions, insertions or substitutions relative to the wild type nucleic acid sequences. The mutation(s) can result in one or more changes (deletions, insertions and/or substitutions) in the amino acid sequence of the encoded protein is not a functional ROD1 protein.

Nucleic Acid Sequences According to the Invention Provided are both wild type ROD1 nucleic acid sequences encoding functional ROD1 proteins and mutant rod1 nucleic acid sequences (comprising one or more mutations, preferably mutations which result in no or a significantly reduced biological activity of the encoded ROD1 protein or in no ROD1 protein being produced) of ROD1 genes from soybean.

However, isolated ROD1 and rod1 nucleic acid sequences (e.g. isolated from the plant by cloning or made synthetically by DNA synthesis), as well as variants thereof and fragments of any of these are also provided herein, as these can be used to determine which sequence is present endogenously in a plant or plant part, whether the sequence encodes a functional, a non-functional or no protein (e.g. by expression in a recombinant host cell as described below) and for selection and transfer of specific alleles from one plant into another, in order to generate a plant having the desired combination of functional and mutant alleles.

Nucleic acid sequences of ROD1-1 and ROD1-2 have been isolated from soybean, nucleic as depicted in the sequence listing. The wild type ROD1 sequences are depicted, while the mutant rod1 sequences of these sequences, and of sequences essentially similar to these, are described herein below and in the Examples, with reference to the wild type ROD1 sequences. The genomic ROD1 protein-encoding DNA from soybean do comprise introns. The coding sequences or cDNA sequences, of the soybean ROD1 genes, not comprising the introns, are also depicted in the sequence listing.

A "soybean ROD1-1 gene", "GmROD1-1 gene", "soybean ROD1-1 allele", "GmROD1-1 allele" or "ROD1-1 from soybean", or variant nucleic acid sequences thereof as used herein refers to a gene, allele or a sequence having at least 90%, or at least 95%, or at least 98%, or at least 99%, or 100% sequence identity SEQ ID No. 1.

A "soybean ROD1-2 gene", "GmROD1-2 gene", "soybean ROD1-2 allele", "GmROD1-2 allele" or "ROD1-2 from soybean", or variant nucleic acid sequences thereof as used herein refers to a gene, allele or a sequence having at least 90%, or at least 95%, or at least 98%, or at least 99%, or 100% sequence identity SEQ ID No. 4.

Thus the invention provides both nucleic acid sequences encoding wild type, functional ROD1 proteins, including variants and fragments thereof (as defined further below), as well as mutant nucleic acid sequences of any of these, whereby the mutation in the nucleic acid sequence preferably results in one or more amino acids being inserted, deleted or substituted in comparison to the wild type ROD1 protein. Preferably the mutation(s) in the nucleic acid sequence result in one or more amino acid changes (i.e. in relation to the wild type amino acid sequence one or more amino acids are inserted, deleted and/or substituted) whereby the biological activity of the ROD1 protein is significantly reduced or completely abolished.

Functionality of the ROD1 protein can be tested, for example, in yeast as described in example 3 or as described by Lu et al. (2009) Proc Natl Acad Sci USA 106:18839.

Both endogenous and isolated nucleic acid sequences are provided herein. Also provided are fragments of the ROD1 sequences and ROD1 variant nucleic acid sequences defined above, for use as primers or probes and as components of kits according to another aspect of the invention (see further below). A "fragment" of a ROD1 or rod1 nucleic acid sequence or variant thereof (as defined) may be of various lengths, such as at least 10, 12, 15, 18, 20, 50, 100, 200, 500, 600 contiguous nucleotides of the ROD1 or rod1 sequence (or of the variant sequence).

Wild-type Nucleic Acid Sequences Encoding Wild-type ROD1 Proteins

The nucleic acid sequences depicted in the sequence listing encode wild type ROD1 proteins from soybean. Thus, these sequences are endogenous to the soybean plants from which they were isolated.

Other soybean varieties, breeding lines or wild accessions may be screened for other ROD1 alleles, encoding the same ROD1 proteins or variants thereof. For example, nucleic acid hybridization techniques (e.g. Southern blot analysis, using for example stringent hybridization conditions) or nucleic acid amplification-based techniques such as PCR techniques may be used to identify ROD1 alleles endogenous to other soybean varieties, lines or accessions. To screen such plants, plant organs or tissues for the presence of ROD1 alleles, the ROD1 nucleic acid sequences provided in the sequence listing, or variants or fragments of any of these, may be used. For example whole sequences or fragments may be used as probes or primers. For example specific or degenerate primers may be used to amplify nucleic acid sequences encoding ROD1 proteins from the genomic DNA of the plant, plant organ or tissue. These ROD1 nucleic acid sequences may be isolated and sequenced using standard molecular biology techniques. Bioinformatics analysis may then be used to characterize the allele(s), for example in order to determine which ROD1 allele the sequence corresponds to and which ROD1 protein or protein variant is encoded by the sequence.

In addition, it is understood that ROD1 nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided, which are described further below.

Mutant Nucleic Acid Sequences Encoding Mutant ROD1 Proteins

Nucleic acid sequences comprising one or more nucleotide deletions, insertions or substitutions relative to the wild type nucleic acid sequences are another embodiment of the invention, as are fragments of such mutant nucleic acid molecules. Such mutant nucleic acid sequences (referred to as rod1 sequences) can be generated and/or identified using various known methods, as described further below. Again, such nucleic acid molecules are provided both in endogenous form and in isolated form. In one embodiment, the mutation(s) result in one or more changes (deletions, insertions and/or substitutions) in the amino acid sequence of the encoded ROD1 protein (i.e. it is not a "silent mutation"). In another embodiment, the mutation(s) in the nucleic acid sequence result in a significantly reduced or completely abolished biological activity of the encoded ROD1 protein relative to the wild type protein.

The knock-out ROD1 genes may, thus, comprise one or more mutations, such as:

(a) a "missense mutation", which is a change in the nucleic acid sequence that results in the substitution of an amino acid for another amino acid;

(b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation;

(c) an "insertion mutation" of one or more amino acids, due to one or more codons having been added in the coding sequence of the nucleic acid;

(d) a "deletion mutation" of one or more amino acids, due to one or more codons having been deleted in the coding sequence of the nucleic acid;

(e) a "frameshift mutation", resulting in the nucleic acid sequence being translated in a different frame downstream of the mutation. A frameshift mutation can have various causes, such as the insertion, deletion or duplication of one or more nucleotides;

(f) a splice site mutation, resulting in altered splicing, which results in an altered mRNA processing and, consequently, in an altered encoded protein which contains either deletions, substitutions or insertions of various lengths, possibly combined with premature translation termination.

Thus in one embodiment, nucleic acid sequences comprising one or more of any of the types of mutations described above are provided. In another embodiment, rod1 sequences comprising one or more stop codon (nonsense) mutations, one or more missense mutations, one or more frameshift mutations, and/or one or more splice site mutations are provided. Any of the above mutant nucleic acid sequences are provided per se (in isolated form), as are plants and plant parts comprising such sequences endogenously. In the tables herein below the most preferred rod1 alleles are described.

A range of possible EMS stop codon mutations in the GmROD1-1 and GmROD1-2 genes are shown in Tables 1a and b, respectively, and a range of possible EMS splice site mutations in the GmROD1-1 and GmROD1-2 genes are shown in Tables 1c and d, respectively.

TABLE 1a possible stop codon mutations in GmROD1-1.

| position relative to the genomic sequence (SEQ ID No. 1) | WT codon | AA | position relative to the protein | stop codon | AA |
|---|---|---|---|---|---|
| 2947-2949 | CAA | GLN | 16 | TAA | STOP |
| 3049-3051 | TGG | TRP | 50 | TAG | STOP |
|  |  |  |  | TAA | STOP |
|  |  |  |  | TGA | STOP |
| 3088-3090 | TGG | TRP | 63 | TAG | STOP |
|  |  |  |  | TAA | STOP |
|  |  |  |  | TGA | STOP |
| 3495-3497 | CAA | GLN | 127 | TAA | STOP |
| 3513-3515 | TGG | TRP | 133 | TAG | STOP |
|  |  |  |  | TAA | STOP |
|  |  |  |  | TGA | STOP |
| 3519-3521 | TGG | TRP | 135 | TAG | STOP |
|  |  |  |  | TAA | STOP |
|  |  |  |  | TGA | STOP |
| 3600-3602 | CAG | GLN | 162 | TAG | STOP |
|  |  |  |  | TAA | STOP |
| 3615-3617 | CAG | GLN | 167 | TAG | STOP |
|  |  |  |  | TAA | STOP |
| 4410-4412 | CAG | GLN | 205 | TAG | STOP |
|  |  |  |  | TAA | STOP |
| 4416-4418 | TGG | TRP | 207 | TAG | STOP |
|  |  |  |  | TAA | STOP |
|  |  |  |  | TGA | STOP |

TABLE 1a-continued possible stop codon mutations in GmROD1-1.

| position relative to the genomic sequence (SEQ ID No. 1) | WT codon | AA | position relative to the protein | stop codon | AA |
|---|---|---|---|---|---|
| 4428-4430 | TGG | TRP | 211 | TAG | STOP |
|  |  |  |  | TAA | STOP |
|  |  |  |  | TGA | STOP |
| 4455-4457 | CAA | GLN | 220 | TAA | STOP |

TABLE 1b possible stop codon mutations in GmROD1-2.

| position relative to the genomic sequence (SEQ ID No. 4) | WT codon | AA | position relative to the protein | stop codon | AA |
|---|---|---|---|---|---|
| 3013-3015 | CAA | GLN | 16 | TAA | STOP |
| 3103-3105 | TGG | TRP | 46 | TAG | STOP |
|  |  |  |  | TAA | STOP |
|  |  |  |  | TGA | STOP |
| 3142-3144 | TGG | TRP | 59 | TAG | STOP |
|  |  |  |  | TAA | STOP |
|  |  |  |  | TGA | STOP |
| 3530-3532 | CAA | GLN | 123 | TAA | STOP |
| 3548-3550 | TGG | TRP | 129 | TAG | STOP |
|  |  |  |  | TAA | STOP |
|  |  |  |  | TGA | STOP |
| 3554-3556 | TGG | TRP | 131 | TAG | STOP |
|  |  |  |  | TAA | STOP |
|  |  |  |  | TGA | STOP |
| 3635-3637 | CAG | GLN | 158 | TAG | STOP |
|  |  |  |  | TAA | STOP |
| 4077-4079 | CAG | GLN | 163 | TAG | STOP |
|  |  |  |  | TAA | STOP |
| 4191-4193 | CAG | GLN | 201 | TAG | STOP |
|  |  |  |  | TAA | STOP |
| 4197-4199 | TGG | TRP | 203 | TAG | STOP |
|  |  |  |  | TAA | STOP |
|  |  |  |  | TGA | STOP |
| 4209-4211 | TGG | TRP | 207 | TAG | STOP |
|  |  |  |  | TAA | STOP |
|  |  |  |  | TGA | STOP |
| 4236-4238 | CAA | GLN | 216 | TAA | STOP |
| 4380-4382 | CAA | GLN | 264 | TAA | STOP |

TABLE 1c possible splice site mutations in GmROD1-1.

| position relative to the genomic sequence (SEQ ID No. 1) | Splice site | WT | mutant |
|---|---|---|---|
| 3264 | Intron 1 - donor | g[gt | a[gt |
| 3265 | Intron 1 - donor | g[gt | g[at |
| 3479 | Intron 1 - acceptor | ag]g | aa]g |
| 3480 | Intron 1 - acceptor | ag]g | ag]a |
| 3617 | Intron 2 - donor | g[gt | a[gt |
| 3618 | Intron 2 - donor | g[gt | g[at |
| 4298 | Intron 2 - acceptor | ag]g | aa]g |
| 4299 | Intron 2 - acceptor | ag]g | ag]a |

TABLE 1d possible splice site mutations in GmROD1-2.

| position relative to the genomic sequence (SEQ ID No. 4) | Splice site | WT | mutant |
|---|---|---|---|
| 3318 | Intron 1 - donor | g[gt | a[gt |
| 3319 | Intron 1 - donor | g[gt | g[at |
| 3514 | Intron 1 - acceptor | ag]g | aa]g |
| 3515 | Intron 1 - acceptor | ag]g | ag]a |
| 3652 | Intron 2 - donor | g[gt | a[gt |
| 3653 | Intron 2 - donor | g[gt | g[at |
| 4079 | Intron 2 - acceptor | ag]g | aa]g |
| 4080 | Intron 2 - acceptor | ag]g | ag]a |

Obviously, mutations are not limited to the ones shown in the above tables and it is understood that analogous STOP mutations may be present in rod1 alleles other than those depicted in the sequence listing and referred to in the tables above. Not only stopcodon mutations, but also mutations resulting in an amino acid substitution may lead to proteins with reduced functionality or with no detectable activity. Amino acids that, when substituted, may lead to proteins with reduced activity are Glu at position 138, Thr at position 144, Arg at position 154, Gly at position 155, and Pro at position 166 of the GmROD1-1 protein, or Glu at position 134, Thr at position 140, Arg at position 150, Gly at position 151, and Pro at position 162 of the GmROD1-2 protein.

Amino Acid Sequences According to the Invention

Provided are both wild type ROD1 amino acid sequences and mutant ROD1 amino acid sequences (comprising one or more mutations, preferably mutations which result in a significantly reduced or no biological activity of the ROD1 protein) from soybean. In addition, mutagenesis methods can be used to generate mutations in wild type ROD1 alleles, thereby generating mutant alleles which can encode further mutant ROD1 proteins. In one embodiment the wild type and/or mutant ROD1 amino acid sequences are provided within a soybean plant (i.e. endogenously). However, isolated ROD1 amino acid sequences (e.g. isolated from the plant or made synthetically), as well as variants thereof and fragments of any of these are also provided herein.

Amino acid sequences of soybean ROD1-1 and ROD1-2 proteins have been isolated as depicted in the sequence listing. The wild type ROD1 sequences are depicted, while the mutant ROD1 sequences of these sequences, and of sequences essentially similar to these, are described herein below, with reference to the wild type ROD1 sequences.

"Soybean ROD1-1 amino acid sequences" or "GmROD1-1 amino acid sequences" or variant amino acid sequences thereof according to the invention are amino acid sequences having at least 95%, 98%, 99% or 100% sequence identity with SEQ ID NO: 3. These amino acid sequences may also be referred to as being "essentially similar" or "essentially identical" to the ROD1 sequences provided in the sequence listing.

"Soybean ROD1-2 amino acid sequences" or "GmROD1-2 amino acid sequences" or variant amino acid sequences thereof according to the invention are amino acid sequences having at least 95%, 98%, 99% or 100% sequence identity with SEQ ID NO: 6. These amino acid sequences may also be referred to as being "essentially similar" or "essentially identical" to the ROD1 sequences provided in the sequence listing.

Thus, the invention provides both amino acid sequences of wild type proteins, including variants and fragments thereof (as defined further below), as well as mutant amino acid sequences of any of these, whereby the mutation in the amino acid sequence preferably results in a significant reduction in or a complete abolishment of the biological activity of the ROD1 protein as compared to the biological activity of the corresponding wild type ROD1 protein.

Both endogenous and isolated amino acid sequences are provided herein. Also provided are fragments of the ROD1 amino acid sequences and ROD1 variant amino acid sequences defined above. A "fragment" of a ROD1 amino acid sequence or variant thereof (as defined) may be of various lengths, such as at least 10, 12, 15, 18, 20, 50, 100, 150, 175, 180 contiguous amino acids of the ROD1 sequence (or of the variant sequence).

Amino Acid Sequences of Wild-type ROD1 Proteins

The amino acid sequences depicted in the sequence listing are wild type ROD1 proteins from soybeans. Thus, these sequences are endogenous to the soybean plants from which they were isolated. Other soybean varieties, breeding lines or wild accessions may be screened for other functional ROD1 proteins with the same amino acid sequences or variants thereof, as described above.

In addition, it is understood that ROD1 amino acid sequences and variants thereof (or fragments of any of these) may be identified in silico, by screening amino acid databases for essentially similar sequences. Fragments of amino acid molecules according to the invention are also provided.

Amino Acid Sequences of Mutant ROD1 Proteins

Amino acid sequences comprising one or more amino acid deletions, insertions or substitutions relative to the wild type amino acid sequences are another embodiment of the invention, as are fragments of such mutant amino acid molecules. Such mutant amino acid sequences can be generated and/or identified using various known methods, as described above. Again, such amino acid molecules are provided both in endogenous form and in isolated form.

In one embodiment, the mutation(s) in the amino acid sequence result in a significantly reduced or completely abolished biological activity of the ROD1 protein relative to the wild type protein. As described above, basically, any mutation which results in a protein comprising at least one amino acid insertion, deletion and/or substitution relative to the wild type protein can lead to significantly reduced or no biological activity.

Thus in one embodiment, mutant ROD1 proteins are provided comprising one or more deletion or insertion mutations, whereby the deletion(s) or insertion(s) result(s) in a mutant protein which has significantly reduced or no activity. Such mutant ROD1 proteins are ROD1 proteins wherein at least 1, at least 2, 3, 4, 5, 10, 20, 30, 50, 100, 150, 200 or more amino acids are deleted, inserted or substituted as compared to the wild type ROD1 protein, whereby the deletion(s) or insertion(s) result(s) in a mutant protein which has significantly reduced or no activity.

In another embodiment, mutant ROD1 proteins are provided which are truncated whereby the truncation results in a mutant protein that has significantly reduced or no activity.

In yet another embodiment, mutant ROD1 proteins are provided comprising one or more substitution mutations, whereby the substitution(s) result(s) in a mutant protein that has significantly reduced or no activity.

In a further embodiment, a transgenic soybean plant is provided comprising a chimeric gene, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells. In another embodiment, said RNA molecule is inhibitory to a ROD1 gene encoding a protein having at least 90% sequence identity to SEQ ID No. 3 or SEQ ID No. 6.

An RNA molecule inhibitory to at least one ROD1 gene can be an RNA that downregulates ROD1 gene expression by decreasing the levels of ROD1 mRNAs available for translation. Said RNA can downregulate ROD1 gene expression through, for example, co-suppression (sense RNA suppression), antisense RNA, double-stranded RNA (dsRNA) or microRNA (miRNA), or ta-siRNA.

Said RNA molecule inhibitory to at least one ROD1 gene is characterized tin that said RNA molecule comprises a region with sufficient homology to said ROD1 genes to be downregulated.

Sufficient homology to the ROD1 genes to be downregulated as used herein means that the transcribed DNA region (and resulting RNA molecule) comprises at least 20 consecutive nucleotides having at least 95% sequence identity to the nucleotide sequence or the complement of the nucleotide of the ROD1 gene to be downregulated.

Said RNA molecule inhibitory to at least one ROD1 gene may be a sense RNA molecule capable of down-regulating expression of one or more functional ROD1 genes by co-suppression. Said RNA molecule comprises at least 20 consecutive nucleotides having at least 95% sequence identity to the nucleotide sequence of one or more ROD1 genes present in the plant cell or plant.

Said RNA molecule inhibitory to at least one ROD1 gene may further be an antisense RNA molecule capable of down-regulating expression of one or more functional ROD1 genes. Said RNA molecule comprises at least 20 consecutive nucleotides having at least 95% sequence identity to the complement of the nucleotide sequence of one or more functional ROD1 genes present in the plant cell or plant.

The minimum nucleotide sequence of the antisense or sense RNA region of about 20 nt of the ROD1 gene may be comprised within a larger RNA molecule, varying in size from 20 nt to a length equal to the size of the target gene. The mentioned antisense or sense nucleotide regions may thus be about from about 21 nt to about 1300 nt long, such as 21 nt, 40 nt, 50 nt, 100 nt, 200 nt, 300 nt, 500 nt, 1000 nt, or even about 1300 nt or larger in length. Moreover, it is not required for the purpose of the invention that the nucleotide sequence of the used inhibitory ROD1 RNA molecule or the encoding region of the transgene, is completely identical or complementary to the endogenous ROD1 gene the expression of which is targeted to be reduced in the plant cell. The longer the sequence, the less stringent the requirement for the overall sequence identity is. Thus, the sense or antisense regions may have an overall sequence identity of about 40% or 50 or 60% or 70% or 80% or 90% or 100% to the nucleotide sequence of the endogenous ROD1 gene or the complement thereof. However, as mentioned, antisense or sense regions should comprise a nucleotide sequence of 20 consecutive nucleotides having about 95 to about 100% sequence identity to the nucleotide sequence of the endogenous ROD1 gene. The stretch of about 95 to about 100% sequence identity may be about 50, 75 or 100 nt. It will be clear that all combinations between mentioned length and sequence identity can be made, both in sense and/or antisense orientation.

The abovementioned chimeric gene may further comprise DNA elements which result in the expression of aberrant, non-polyadenylated ROD1 inhibitory RNA molecules. One such DNA element suitable for that purpose is a DNA region encoding a self-splicing ribozyme, as described in WO 00/01133. The efficiency may also be enhanced by providing the generated RNA molecules with nuclear localization or retention signals as described in WO 03/076619.

Said RNA molecule inhibitory to at least one ROD1 gene may further be a double-stranded RNA molecule capable of down-regulating ROD1 gene expression. Upon transcription of the DNA region the RNA is able to form dsRNA molecule through conventional base paring between a sense and antisense region, whereby the sense and antisense region are nucleotide sequences as hereinbefore described. dsRNA-encoding ROD1 expression-reducing chimeric genes according to the invention may further comprise an intron, such as a heterologous intron, located e.g. in the spacer sequence between the sense and antisense RNA regions in accordance with the disclosure of WO 99/53050. To achieve the construction of such a transgene, use can be made of the vectors described in WO 02/059294 A1.

Said RNA molecule inhibitory to at least one ROD1 gene may further be a pre-miRNA molecule which is processed into a miRNA capable of guiding the cleavage of ROD1 mRNA. miRNAs are small endogenous RNAs that regulate gene expression in plants, but also in other eukaryotes. In plants, these about 21 nucleotide long RNAs are processed from the stem-loop regions of long endogenous pre-miR-NAs by the cleavage activity of DICERLIKE1 (DCL1). Plant miRNAs are highly complementary to conserved target mRNAs, and guide the cleavage of their targets. miRNAs appear to be key components in regulating the gene expression of complex networks of pathways involved inter alia in development.

As used herein, a "miRNA" is an RNA molecule of about 20 to 22 nucleotides in length which can be loaded into a RISC complex and direct the cleavage of a target RNA molecule, wherein the target RNA molecule comprises a nucleotide sequence essentially complementary to the nucleotide sequence of the miRNA molecule whereby one or more of the following mismatches may occur:

A mismatch between the nucleotide at the 5' end of said miRNA and the corresponding nucleotide sequence in the target RNA molecule;

A mismatch between any one of the nucleotides in position 1 to position 9 of said miRNA and the corresponding nucleotide sequence in the target RNA molecule;

Three mismatches between any one of the nucleotides in position 12 to position 21 of said miRNA and the corresponding nucleotide sequence in the target RNA molecule provided that there are no more than two consecutive mismatches.

No mismatch is allowed at positions 10 and 11 of the miRNA (all miRNA positions are indicated starting from the 5' end of the miRNA molecule).

As used herein, a "pre-miRNA" molecule is an RNA molecule of about 100 to about 200 nucleotides, preferably about 100 to about 130 nucleotides which can adopt a secondary structure comprising a dsRNA stem and a single stranded RNA loop and further comprising the nucleotide sequence of the miRNA and its complement sequence of the miRNA* in the double-stranded RNA stem. Preferably, the miRNA and its complement are located about 10 to about 20 nucleotides from the free ends of the miRNA dsRNA stem. The length and sequence of the single stranded loop region are not critical and may vary considerably, e.g. between 30 and 50 nt in length. Preferably, the difference in free energy between unpaired and paired RNA structure is between −20 and −60 kcal/mole, particularly around −40 kcal/mole. The complementarity between the miRNA and the miRNA* do not need to be perfect and about 1 to 3 bulges of unpaired nucleotides can be tolerated. The secondary structure adopted by an RNA molecule can be predicted by computer algorithms conventional in the art such as mFold, UNAFold and RNAFold. The particular strand of the dsRNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional because the "wrong" strand is loaded on the RISC complex, it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds.

Said RNA molecule inhibitory to at least one ROD1 gene may further be a ta-siRNAs as described in WO2006/074400.

Said RNA molecule may be inhibitory to all ROD1 genes present in said soybean plant. For example, said RNA molecule is inhibitory to a ROD1 gene encoding a protein having at least 90% sequence identity to SEQ ID No. 3 and SEQ ID No. 6, such as a ROD1 gene having at least 90% sequence identity, or at least 95% sequence identity, or at least 98% sequence identity or having 100% sequence identity to SEQ ID No. 1 or SEQ ID No. 4, respectively.

Said RNA molecule may further be inhibitory to only one ROD1 gene, such as the ROD1 genes encoding a protein having at least 90% sequence identity to SEQ ID No. 3 only, such as a ROD1 gene having at least 90% sequence identity, or at least 95% sequence identity, or at least 98% sequence identity or having 100% sequence identity to SEQ ID No. 1, or to the ROD1 gene encoding a protein having at least 90% sequence identity to SEQ ID No. 6 only, such as a ROD1 gene having at least 90% sequence identity, or at least 95% sequence identity, or at least 98% sequence identity or having 100% sequence identity to SEQ ID No. 4.

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al. (1988) *Mol Gen Genet.* 212(1):182-90, the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al. (1996) *Plant Cell* 8(1):15-30), stem-specific promoters (Keller et al., (1988) *EMBO J.* 7(12): 3625-3633), leaf specific promoters (Hudspeth et al. (1989) *Plant Mol Biol.* 12: 579-589), mesophyl-specific promoters (such as the light-inducible Rubisco promoters), root-specific promoters (Keller et al. (1989) *Genes Dev.* 3: 1639-1646), tuber-specific promoters (Keil et al. (1989) *EMBO J.* 8(5): 1323-1330), vascular tissue specific promoters (Peleman et al. (1989) *Gene* 84: 359-369), stamen-selective promoters (WO 89/10396, WO 92/13956), dehiscence zone specific promoters (WO 97/13865) and the like.

A "heterologous promoter" as used herein refers to a promoter which is not normally associated in its natural context with the coding DNA region operably linked to it in the DNA molecules according to the invention.

Said plant-expressible promoter can, for example, be a constitutive promoter, such as the CaMV35S promoter (Harpster et al. (1988) *Mol Gen Genet.* 212(1):182-90), or a seed-specific promoter, such as the *Arabidopsis* oleosin promoter (WO1998/045461).

Constitutive promoters are well known in the art, and include the CaMV35S promoter (Harpster et al. (1988) *Mol Gen Genet.* 212(1):182-90), Actin promoters, such as, for example, the promoter from the Rice Actin gene (McElroy et al., 1990, Plant Cell 2:163), the promoter of the Cassava Vein Mosaic Virus (Verdaguer et al., 1996 Plant Mol. Biol. 31: 1129), the GOS promoter (de Pater et al., 1992, Plant J. 2:837), the Histone H3 promoter (Chaubet et al., 1986, Plant Mol Biol 6:253), the *Agrobacterium tumefaciens* Nopaline Synthase (Nos) promoter (Depicker et al., 1982, J. Mol. Appl. Genet. 1: 561), or Ubiquitin promoters, such as, for example, the promoter of the maize Ubiquitin-1 gene (Christensen et al., 1992, Plant Mol. Biol. 18:675).

Seed specific promoters are well known in the art, including the *Arabidopsis* oleosin promoter (WO1998/045461), the USP promoter from *Vicia faba* described in DE10211617; the promoter sequences described in WO2009/073738; promoters from *Brassica napus* for seed specific gene expression as described in WO2009/077478; the plant seed specific promoters described in US2007/0022502; the plant seed specific promoters described in WO03/014347; the seed specific promoter described in WO2009/125826; the promoters of the omega_3 fatty acid desaturase family described in WO2006/005807 and the like.

A "transcription termination and polyadenylation region" as used herein is a sequence that drives the cleavage of the nascent RNA, whereafter a poly(A) tail is added at the resulting RNA 3' end, functional in plants. Transcription termination and polyadenylation signals functional in plants include, but are not limited to, 3'nos, 3'35S, 3'his and 3'g7.

In a further embodiment, the seeds of the plants according to the invention have increased levels of C18:1, or increased levels of C18:1 and decreased levels of C18:2, or increased levels of C18:1 and decreased levels of SATS.

In a further embodiment, seeds are provided from the plants according to the invention, i.e. plants comprising a knock-out ROD1 gene or an RNA inhibitory to a ROD1 gene. In yet another embodiment, oil from the seeds of the plants according to the invention is provided.

In another embodiment, a method is provided for increasing the C18:1 levels in soybean seed oil, comprising modulating the expression of a ROD1 gene. In yet another embodiment, a method is provided for increasing the C18:1 levels in soybean seed oil, comprising the steps of introducing or providing an chimeric gene to a soybean plant cell, to create transgenic cells, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells; and regenerating transgenic plants from said transgenic cells.

"C18:1", also referred to as "oleic acid", "cis-9-octadecenoic", "18:1", "18:1 (n-9)", "9c-18:1" or "18:1cis $\Delta^9$" as used herein, refers to a monounsaturated omega-9 fatty acid, with the IUPAC name (9Z)-Octadec-9-enoic acid.

"C18:2", also referred to as "linoleic acid", "cis-9,12-octadecadienoic acid", "18:2", "18:2 (n-6)", "9c12c-18:1 or "18:2cis $\Delta^{9, 12}$", as used herein, refers to a carboxylic acid with an 18-carbon chain and two double bonds with the IUPAC name cis, cis-9,12-Octadecadienoic acid.

SATS, as used herein, refers to saturated fatty acids, which refers to the sum of the levels of C12:0, C14:0, C16:0, C18:0, C20:0, C22:0 and C24:0.

Increasing the C18:1 levels or increased C18:1 levels in seed oil can be an increase of C18:1 levels with at least 2%, or at least 5%, or at least 8%, or at least 10%, or at least 12%. Said increase is an increase with respect to C18:1 levels as obtained in control plants.

Decreased levels of C18:2 can be a decrease of C18:2 levels in seed oil with at least 2%, or at least 5%, or at least 8%, or at least 10%, or at least 20%, or at least 30%.

Decreased levels of SATS can be a decrease in the levels of SATS in seed oil with at least 2%, or at least 3%, or at least 5%. A decrease in the levels of SATS refers to a decrease in the total levels of the sum of C16:0, C18:0, C20:0, C22:0 and C24:0. As such, a decrease in the levels of SATS can be a decrease in the levels of only one of the saturated fatty acids, or of more than one of the saturated fatty acids.

Optionally, the increase of the C18:1 levels or decrease of the C18:2 or SATS in seeds or in seed oil is higher than an increase in C18:1 levels or decrease of the C18:2 or SATS in membrane lipids. For example, the levels of C18:1 are increased, or the C18:2 levels or SATS are increased in the seeds, but the C18:1, C18:2 and SATS levels are unchanged in membrane lipids.

C18:1, C18:2 and SATS levels can be measured as described herein, such as, for example, using the methods as described in Examples 4 and 5.

The "control plant" as used herein is generally a plant of the same species which has wild-type levels of ROD1. "Wild-type levels of ROD1" as used herein refers to the typical levels of ROD1 protein in a plant as it most commonly occurs in nature. Said control plant does contain an RNA molecule inhibitory to ROD1, and in which the ROD1 genes are wild-type ROD1 genes.

A chimeric gene can be provided to a plant or plant cell using methods well-known in the art. Methods to provide plant cells with a chimeric are not deemed critical for the current invention and any method to provide plant cells with a chimeric gene suitable for a particular plant species can be used. Such methods are well known in the art and include *Agrobacterium*-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. Said chimeric can be transiently introduced into the plant cell or plant cell nucleus. Said chimeric may be stably integrated into the genome of said plant cell, resulting in a transformed plant cell. The transformed plant cells obtained in this way may then be regenerated into mature fertile transformed plants.

The obtained transformed plant, comprising the RNA molecule inhibitory to at least one ROD1 gene, can be used in a conventional breeding scheme to produce more transformed plants with the same characteristics or to introduce the transgene according to the invention in other varieties of the same or related plant species, or in hybrid plants. Seeds obtained from the transformed plants contain the chimeric genes of the invention as a stable genomic insert and are also encompassed by the invention.

In again another embodiment, a method is provided for increasing the C18:1 levels in seed oil, comprising the steps of treating seeds or plant material with a mutagenic chemical substance or with ionizing radiation; identifying plants with a mutated rod1 gene, wherein the ROD1 gene, prior to being mutated, encodes a polypeptide having at least 90% sequence identity to SEQ ID No. 3 or to SEQ ID No. 6; and selecting a plant with an increased level of C18:1 in the seeds compared to a plant in which the ROD1 gene is not mutated.

Said ROD1 gene, prior to being mutated, can be, for example, a ROD1 gene having at least 90% sequence identity, or at least 95% sequence identity, or at least 98% sequence identity or having 100% sequence identity to SEQ ID No. 1, or SEQ ID no. 4.

In a further embodiment, a method is provided for obtaining a soybean plant with increased levels of C18:1 in the seeds comprising the step of introducing a knock-out allele of a ROD1 gene in said soybean plant, and selecting said soybean plant with increased levels of C18:1 in the seeds for the presence of said knock-out allele of a ROD1 gene by analyzing genomic DNA from said plant for the presence of at least one molecular marker, wherein said at least one molecular marker is linked to said knock-out allele of a ROD1 gene.

Introducing said knock-out allele of ROD1 can occur through mutagenesis or gene targeting as described above. Introducing said knock-out allele can also occur through introduction of a knock-out ROD1 allele from one plant into another.

In another embodiment, a method is provided to determine the presence or absence of a knock-out allele of a ROD1 gene in a biological sample, comprising providing genomic DNA from said biological sample, and analyzing said DNA for the presence of at least one molecular marker, wherein the at least one molecular marker is linked to said knock-out allele of a ROD1 gene.

Said genomic DNA can be provided by isolating genomic DNA from said biological sample. Isolating genomic DNA refers to isolating a biological sample comprising genomic DNA from, such as isolating part of a tissue, such as, for example part of a leaf.

Isolating genomic DNA from said biological sample can, but does not need to comprise, purification of genomic DNA from said sample.

Yet another embodiment provides a kit for the detection of a knock-out allele of a ROD1 gene in soybean DNA samples, wherein said kit comprises one or more PCR primer pairs, which are able to amplify a DNA marker linked to said knock-out allele of a ROD1 gene. In yet another embodiment, said kit further comprises one or more probes.

In a specific embodiment, said knock-out allele of a ROD1 gene is a mutant ROD1 allele.

In a further embodiment, a method is provided for determining the zygosity status of a mutant ROD1 allele in a soybean plant, or a cell, part, seed or progeny thereof, comprising determining the presence of a mutant and/or a corresponding wild type ROD1 specific region in the genomic DNA of said plant, or a cell, part, seed or progeny thereof.

Yet a further embodiment provides method for transferring at least one knock-out ROD1 allele from one soybean plant to another soybean plant comprising the steps of identifying a first soybean plant comprising at least one knock-out ROD1 allele; crossing the first soybean plant with a second soybean plant not comprising the at least one knock-out ROD1 allele and collecting F1 seeds from the cross; optionally, identifying F1 soybean plants comprising the at least one knock-out ROD1 allele; backcrossing F1 soybean plants comprising the at least one knock-out ROD1 allele with the second plant not comprising the at least one knock-out ROD1 allele for at least one generation (x) and collecting BCx seeds from the crosses; identifying in every generation BCx soybean plants comprising the at least one knock-out ROD1 allele by analyzing genomic DNA of said BCx plants for the presence of at least one molecular marker, wherein the at least one molecular marker is linked to said knock-out ROD1 allele.

A molecular marker which is linked to said knock-out allele of a ROD1 gene or said mutant ROD1 allele can comprise on or more primers or probes that specifically detect said knock-out allele of said ROD1 gene as described herein below.

Methods According to the Invention

Mutant rod1 alleles may be generated (for example induced by mutagenesis) and/or identified using a range of methods, which are conventional in the art, for example using nucleic acid amplification based methods to amplify part or all of the rod1 genomic or cDNA.

Following mutagenesis, plants are grown from the treated seeds, or regenerated from the treated cells using known techniques. For instance, mutagenized seeds may be planted in accordance with conventional growing procedures and following self-pollination seed is formed on the plants. Additional seed which is formed as a result of such self-pollination in the present or a subsequent generation may be harvested and screened for the presence of mutant ROD1 alleles, using techniques which are conventional in the art, for example nucleic acid amplification based techniques, such as polymerase chain reaction (PCR) based techniques (amplification of the rod1 alleles) or hybridization based techniques, e.g. Southern blot analysis, BAC library screening, and the like, and/or direct sequencing of rod1 alleles. To screen for the presence of point mutations (so called Single Nucleotide Polymorphisms or SNPs) in mutant ROD1 alleles, SNP detection methods conventional in the art can be used, for example oligoligation-based techniques, single base extension-based techniques or techniques based on differences in restriction sites, such as TILLING.

As described above, mutagenization (spontaneous as well as induced) of a specific wild-type ROD1 allele results in the presence of one or more deleted, inserted, or substituted nucleotides (hereinafter called "mutation region") in the resulting mutant ROD1 allele. The mutant ROD1 allele can thus be characterized by the location and the configuration of the one or more deleted, inserted, or substituted nucleotides in the wild type ROD1 allele. The site in the wild type ROD1 allele where the one or more nucleotides have been inserted, deleted, or substituted, respectively, is herein also referred to as the "mutation region or sequence". A "5' or 3' flanking region or sequence" as used herein refers to a DNA region or sequence in the mutant (or the corresponding wild type) ROD1 allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) ROD1 allele which is located either immediately upstream of and contiguous with (5' flanking region or sequence") or immediately downstream of and contiguous with (3' flanking region or sequence") the mutation region in the mutant ROD1 allele (or in the corresponding wild type ROD1 allele). A "joining region" as used herein refers to a DNA region in the mutant (or the corresponding wild type) ROD1 allele where the mutation region and the 5' or 3' flanking region are linked to each other.

A "sequence spanning the joining region between the mutation region and the 5' or 3' flanking region thus comprises a mutation sequence as well as the flanking sequence contiguous therewith.

The tools developed to identify a specific mutant ROD1 allele or the plant or plant material comprising a specific mutant ROD1 allele, or products which comprise plant material comprising a specific mutant ROD1 allele are based on the specific genomic characteristics of the specific mutant ROD1 allele as compared to the genomic characteristics of the corresponding wild type ROD1 allele, such as, a specific restriction map of the genomic region comprising the mutation region, molecular markers comprising primers and/or probes as described below, or the sequence of the flanking and/or mutation regions.

Once a specific mutant ROD1 allele has been sequenced, molecular markers, such as primers and probes can be developed which specifically recognize a sequence within the 5' flanking, 3' flanking and/or mutation regions of the mutant ROD1 allele in the nucleic acid (DNA or RNA) of a sample by way of a molecular biological technique. For instance an amplification method can be developed to identify the mutant ROD1 allele in biological samples (such as samples of plants, plant material or products comprising plant material). Such an amplification is based on at least two specific "primers": one recognizing a sequence within the 5' or 3' flanking region of the mutant ROD1 allele and the other recognizing a sequence within the 3' or 5' flanking region of the mutant ROD1 allele, respectively; or one recognizing a sequence within the 5' or 3' flanking region of the mutant ROD1 allele and the other recognizing a sequence within the mutation region of the mutant ROD1 allele; or one recognizing a sequence within the 5' or 3' flanking region of the mutant ROD1 allele and the other recognizing a sequence spanning the joining region between the 3' or 5' flanking region and the mutation region of the specific mutant ROD1 allele (as described further below), respectively.

The primers preferably have a sequence of between 15 and 35 nucleotides which under optimized amplification conditions "specifically recognize" a sequence within the 5' or 3' flanking region, a sequence within the mutation region, or a sequence spanning the joining region between the 3' or 5' flanking and mutation regions of the specific mutant ROD1 allele, so that a specific fragment ("mutant ROD1 specific fragment" or discriminating amplicon) is amplified from a nucleic acid sample comprising the specific mutant ROD1 allele. This means that only the targeted mutant ROD1 allele, and no other sequence in the plant genome, is amplified under optimized amplification conditions.

PCR primers suitable for the invention may be the following:
 oligonucleotides ranging in length from 17 nt to about 200 nt, comprising a nucleotide sequence of at least 17 consecutive nucleotides, preferably 20 consecutive nucleotides selected from the 5' or 3' flanking sequence of a specific mutant ROD1 allele or the complement thereof (i.e., for example, the sequence 5' or 3' flanking the one or more nucleotides deleted, inserted or substituted in the mutant ROD1 alleles of the invention, such as the sequence 5' or 3' flanking the non-sense, mis-sense, frameshift or splice site mutations described above or the sequence 5' or 3' flanking the STOP codon mutations indicated in the above Tables or the substitution mutations indicated above or the complement thereof) (primers recognizing 5' flanking sequences); or
 oligonucleotides ranging in length from 17 nt to about 200 nt, comprising a nucleotide sequence of at least 17 consecutive nucleotides, preferably 20 nucleotides selected from the sequence of the mutation region of a specific mutant ROD1 allele or the complement thereof (i.e., for example, the sequence of nucleotides inserted or substituted in the ROD1 genes of the invention or the complement thereof) (primers recognizing mutation sequences).

The primers may of course be longer than the mentioned 17 consecutive nucleotides, and may e.g. be 18, 19, 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be no longer than 100, more preferably not longer than 50 or even 25 nucleotides.

Moreover, suitable primers may comprise or consist of a nucleotide sequence spanning the joining region between flanking and mutation sequences (i.e., for example, the joining region between a sequence 5' or 3' flanking one or more nucleotides deleted, inserted or substituted in the mutant ROD1 alleles of the invention and the sequence of the one or more nucleotides inserted or substituted or the sequence 3' or 5', respectively, flanking the one or more nucleotides deleted, such as the joining region between a sequence 5' or 3' flanking non-sense, missense, frameshift or splice site mutations in the ROD1 genes of the invention described above and the sequence of the non-sense, missense, frameshift or splice site mutations, or the joining region between a sequence 5' or 3' flanking a potential STOP codon mutation as indicated in the above Tables or the substitution mutations indicated above and the sequence of the potential STOP codon mutation or the substitution mutations, respectively), provided the nucleotide sequence is not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A ←→T; G ←→C) and reading the sequence in the 5' to 3' direction, i.e. in opposite direction of the represented nucleotide sequence.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, to a sequence within the mutation region, or to a sequence spanning the joining region between the 3' or 5' flanking and mutation regions of the specific mutant ROD1 allele, provided the mismatches still allow specific identification of the specific mutant ROD1 allele with these primers under optimized amplification conditions. The range of allowable mismatches however, can easily be determined experimentally and are known to a person skilled in the art.

Detection and/or identification of a "mutant ROD1 specific fragment" can occur in various ways, e.g., via size estimation after gel or capillary electrophoresis or via fluorescence-based detection methods. The mutant ROD1 specific fragments may also be directly sequenced. Other sequence specific methods for detection of amplified DNA fragments are also known in the art.

Standard nucleic acid amplification protocols, such as PCR protocols are described in the art, such as in "PCR Applications Manual" (Roche Molecular Biochemicals, 2nd Edition, 1999) and other references. The optimal conditions for the amplification, including the sequence of the specific primers, is specified in a "PCR identification protocol" for each specific mutant ROD1 allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, $MgCl_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify a mutant ROD1 specific fragment that can be used as a "specific probe" for identifying a specific mutant ROD1 allele in biological samples. Contacting nucleic acid of a biological sample, with the probe, under conditions that allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant ROD1 allele. Such identification methods based on hybridization with a specific probe (either on a solid phase carrier or in solution) have been described in the art. The specific probe is preferably a sequence that, under optimized conditions, hybridizes specifically to a region within the 5' or 3' flanking region and/or within the mutation region of the specific mutant ROD1 allele (hereinafter referred to as "mutant ROD1 specific region"). Preferably, the specific probe comprises a sequence of between 10 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 13 to about 100 contiguous nucleotides identical (or complementary) to a specific region of the specific mutant ROD1 allele.

Specific probes suitable for the invention may be the following:
oligonucleotides ranging in length from 13 nt to about 1000 nt, comprising a nucleotide sequence of at least 13 consecutive nucleotides selected from the 5' or 3' flanking sequence of a specific mutant ROD1 allele or the complement thereof (i.e., for example, the sequence 5' or 3' flanking the one or more nucleotides deleted, inserted or substituted in the mutant ROD1 alleles of the invention, such as the sequence 5' or 3' flanking the non-sense, mis-sense, frameshift or splice site mutations described above or the sequence 5' or 3' flanking the potential STOP codon mutations indicated in the above Tables or the substitution mutations indicated above), or a sequence having at least 80% sequence identity therewith (probes recognizing 5' flanking sequences); or
oligonucleotides ranging in length from 13 nt to about 1000 nt, comprising a nucleotide sequence of at least 13 consecutive nucleotides selected from the mutation sequence of a specific mutant ROD1 allele or the complement thereof (i.e., for example, the sequence of nucleotides inserted or substituted in the ROD1 genes of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be no longer than 50, more preferably not longer than 25 or even no longer than 20 or 15 nucleotides.

Moreover, suitable probes may comprise or consist of a nucleotide sequence spanning the joining region between flanking and mutation sequences (i.e., for example, the joining region between a sequence 5' or 3' flanking one or more nucleotides deleted, inserted or substituted in the mutant ROD1 alleles of the invention and the sequence of the one or more nucleotides inserted or substituted or the sequence 3' or 5', respectively, flanking the one or more nucleotides deleted, such as the joining region between a sequence 5' or 3' flanking non-sense, mis-sense, frameshift or splice site mutations in the ROD1 genes of the invention described above and the sequence of the non-sense, mis-sense, frameshift or splice site mutations, or the joining region between a sequence 5' or 3' flanking a potential STOP codon mutation as indicated in the above Tables or the substitution mutations indicated above and the sequence of the potential STOP codon or substitution mutation, respectively), provided the mentioned nucleotide sequence is not derived exclusively from either the mutation region or flanking regions.

Detection and/or identification of a "mutant ROD1 specific region" hybridizing to a specific probe can occur in various ways, e.g., via size estimation after gel electrophoresis or via fluorescence-based detection methods. Other sequence specific methods for detection of a "mutant ROD1 specific region" hybridizing to a specific probe are also known in the art.

Alternatively, plants or plant parts comprising one or more mutant rod1 alleles can be generated and identified using other methods, such as the "Delete-a-gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants or plant parts comprising one or more mutant rod1 alleles and methods for generating and identifying such plants, plant organs, tissues and seeds is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in ROD1 alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant rod1 alleles. In ECOTILLING natural polymorphisms in breeding lines or related species are screened for by the TILLING methodology described above, in which individual or pools of plants are used for PCR amplification of the rod1 target, heteroduplex formation and high-throughput analysis. This can be followed by selecting individual plants having a required mutation that can be used subsequently in a breeding program to incorporate the desired mutant allele.

The identified mutant alleles can then be sequenced and the sequence can be compared to the wild type allele to identify the mutation(s). Optionally functionality can be tested as indicated above. Using this approach a plurality of mutant rod1 alleles (and plants comprising one or more of these) can be identified. The desired mutant alleles can then be combined with the desired wild type alleles by crossing and selection methods as described further below. Finally a single plant comprising the desired number of mutant rod1 and the desired number of wild type ROD1 alleles is generated.

Oligonucleotides suitable as PCR primers or specific probes for detection of a specific mutant ROD1 allele can also be used to develop methods to determine the zygosity status of the specific mutant ROD1 allele.

To determine the zygosity status of a specific mutant ROD1 allele, a nucleic acid amplification-based assay can be developed to determine the presence of a mutant and/or corresponding wild type ROD1 specific allele:

To determine the zygosity status of a specific mutant ROD1 allele, two primers specifically recognizing the wild-type ROD1 allele can be designed in such a way that they are directed towards each other and have the mutation region located in between the primers. These primers may be primers specifically recognizing the 5' and 3' flanking sequences, respectively. This set of primers allows simultaneous diagnostic amplification of the mutant, as well as of the corresponding wild type ROD1 allele.

Alternatively, to determine the zygosity status of a specific mutant ROD1 allele, two primers specifically recognizing the wild-type ROD1 allele can be designed in such a way that they are directed towards each other and that one of them specifically recognizes the mutation region. These primers may be primers specifically recognizing the sequence of the 5' or 3' flanking region and the mutation region of the wild type ROD1 allele, respectively. This set of primers, together with a third primer which specifically recognizes the sequence of the mutation region in the mutant ROD1 allele, allow simultaneous diagnostic amplification of the mutant ROD1 gene, as well as of the wild type ROD1 gene.

Alternatively, to determine the zygosity status of a specific mutant ROD1 allele, two primers specifically recognizing the wild-type ROD1 allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type ROD1 allele, respectively. This set of primers, together with a third primer which specifically recognizes the joining region between the mutation region and the 3' or 5' flanking region of the mutant ROD1 allele, respectively, allow simultaneous diagnostic amplification of the mutant ROD1 gene, as well as of the wild type ROD1 gene.

Alternatively, the zygosity status of a specific mutant ROD1 allele can be determined by using alternative primer sets that specifically recognize mutant and wild type ROD1 alleles.

If the plant is homozygous for the mutant ROD1 gene or the corresponding wild type ROD1 gene, the diagnostic amplification assays described above will give rise to a single amplification product typical, preferably typical in length, for either the mutant or wild type ROD1 allele. If the plant is heterozygous for the mutant ROD1 allele, two specific amplification products will appear, reflecting both the amplification of the mutant and the wild type ROD1 allele.

Identification of the wild type and mutant ROD1 specific amplification products can occur e.g. by size estimation after gel or capillary electrophoresis (e.g. for mutant ROD1 alleles comprising a number of inserted or deleted nucleotides which results in a size difference between the fragments amplified from the wild type and the mutant ROD1 allele, such that said fragments can be visibly separated on a gel); by evaluating the presence or absence of the two different fragments after gel or capillary electrophoresis, whereby the diagnostic amplification of the mutant ROD1 allele can, optionally, be performed separately from the diagnostic amplification of the wild type ROD1 allele; by direct sequencing of the amplified fragments; or by fluorescence-based detection methods.

Alternatively, to determine the zygosity status of a specific mutant ROD1 allele, a hybridization-based assay can be developed to determine the presence of a mutant and/or corresponding wild type ROD1 specific allele:

To determine the zygosity status of a specific mutant ROD1 allele, two specific probes recognizing the wild-type ROD1 allele can be designed in such a way that each probe specifically recognizes a sequence within the ROD1 wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type ROD1 allele.

Alternatively, to determine the zygosity status of a specific mutant ROD1 allele, two specific probes recognizing the wild-type ROD1 allele can be designed in such a way that one of them specifically recognizes a sequence within the ROD1 wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type ROD1 allele, respectively. The use of one or, preferably, both of these probes, optionally, together with a third probe which specifically recognizes the sequence of the mutation region in the mutant ROD1 allele, allow diagnostic hybridization of the mutant and of the wild type ROD1 gene.

Alternatively, to determine the zygosity status of a specific mutant ROD1 allele, a specific probe recognizing the wild-type ROD1 allele can be designed in such a way that the probe specifically recognizes the joining region between the 5' or 3' flanking region, preferably the 5' flanking region, and the mutation region of the wild type ROD1 allele. This probe, optionally, together with a second probe that specifically recognizes the joining region between the 5' or 3' flanking region, preferably the 5' flanking region, and the mutation region of the mutant ROD1 allele, allows diagnostic hybridization of the mutant and of the wild type ROD1 gene.

Alternatively, the zygosity status of a specific mutant ROD1 allele can be determined by using alternative sets of probes that specifically recognize mutant and wild type ROD1 alleles.

If the plant is homozygous for the mutant ROD1 gene or the corresponding wild type ROD1 gene, the diagnostic hybridization assays described above will give rise to a single specific hybridization product, such as one or more hybridizing DNA (restriction) fragments, typical, preferably typical in length, for either the mutant or wild type ROD1 allele. If the plant is heterozygous for the mutant ROD1 allele, two specific hybridization products will appear, reflecting both the hybridization of the mutant and the wild type ROD1 allele.

Identification of the wild type and mutant ROD1 specific hybridization products can occur e.g. by size estimation after gel or capillary electrophoresis (e.g. for mutant ROD1 alleles comprising a number of inserted or deleted nucleotides which results in a size difference between the hybridizing DNA (restriction) fragments from the wild type and the mutant ROD1 allele, such that said fragments can be visibly separated on a gel); by evaluating the presence or absence of the two different specific hybridization products after gel or capillary electrophoresis, whereby the diagnostic hybridization of the mutant ROD1 allele can, optionally, be performed separately from the diagnostic hybridization of the wild type ROD1 allele; by direct sequencing of the hybridizing DNA (restriction) fragments; or by fluorescence-based detection methods.

Furthermore, detection methods specific for a specific mutant ROD1 allele that differ from PCR- or hybridization-based amplification methods can also be developed using the specific mutant ROD1 allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

A "kit", as used herein, refers to a set of reagents for the purpose of performing the method of the invention, more particularly, the identification of a specific mutant ROD1 allele in biological samples or the determination of the zygosity status of plant material comprising a specific mutant ROD1 allele. More particularly, a preferred embodiment of the kit of the invention comprises at least two specific primers, as described above, for identification of a specific mutant ROD1 allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant ROD1 allele therein, as described above, for identification of a specific mutant ROD1 allele, or at least two or three specific probes for the determination of the zygosity status. Optionally, the kit can further comprise any other reagent (such as but not limited to hybridizing buffer, label) for identification of a specific mutant ROD1 allele in biological samples, using the specific probe.

The kit of the invention can be used, and its components can be specifically adjusted, for purposes of quality control (e.g., purity of seed lots), detection of the presence or absence of a specific mutant ROD1 allele in plant material or material comprising or derived from plant material, such as but not limited to food or feed products.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant ROD1 allele under the conditions set forth in the method (such as the conditions of the PCR identification protocol), whereby the specificity is determined by the presence of positive and negative controls.

The term "hybridizing", as used herein when referring to specific probes, refers to the fact that the probe binds to a specific region in the nucleic acid sequence of a specific mutant ROD1 allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denatured carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material that is obtained or derived from a plant. Products comprising plant material relate to food, feed or other products that are produced using plant material or can be contaminated by plant material. It is understood that, in the context of the present invention, such biological samples are tested for the presence of nucleic acids specific for a specific mutant ROD1 allele, implying the presence of nucleic acids in the samples. Thus the methods referred to herein for identifying a specific mutant ROD1 allele in biological samples, relate to the identification in biological samples of nucleic acids that comprise the specific mutant ROD1 allele.

Another embodiment provides a chimeric gene comprising the following operably linked elements: a plant-expressible promoter; a DNA region, which when transcribed yields an RNA molecule inhibitory to at least one ROD1 gene, said ROD1 gene encoding a protein having at least 90% sequence identity to SEQ ID No. 3 or SEQ ID No. 6; and optionally a transcription termination and polyadenylation region functional in plant cells.

In again another embodiment, a knock-out allele of a ROD1 gene is provided, wherein the knock-out ROD1 allele is a mutated version of the native ROD1 gene selected from the group consisting of: a nucleic acid molecule which comprises at least 90% sequence identity to SEQ ID No. 1 or SEQ ID No. 4; or a nucleic acid molecule encoding an amino acid sequence comprising at least 90% sequence identity to SEQ ID No. 3 or SEQ ID No. 6, wherein said mutant rod1 allele comprises a mutated DNA region consisting of one or more inserted, deleted or substituted nucleotides compared to a corresponding wild-type DNA region in the functional ROD1 gene and wherein said mutant rod1 allele encodes no functional ROD1 protein or encodes a ROD1 protein with reduced activity.

The chimeric gene according to the invention can be used to produce plants, such as soybean plants, with increased levels of C18:1 in the seeds, or with decreased levels of C18:2 or SATS in the seeds, or to produce seed oil with increased levels of C18:1, or with decreased levels of C18:2 or SATS.

In a further embodiment, a method is provided for producing oil, comprising harvesting seeds from the plants according to the invention, i.e. soybean plants comprising a knock-out ROD1 gene or an RNA inhibitory to a ROD1 gene, and extracting the oil from said seeds.

In yet a further embodiment, a method is provided of producing food or feed, such as oil, meal, grain, starch, flour or protein, or an industrial product, such as bio fuel, fiber, industrial chemicals, a pharmaceutical or a neutraceutical, comprising obtaining the soybean plant or a part thereof according to the invention, and preparing the food, feed or industrial product from the plant or part thereof.

Plants according to the invention, such as plants comprising at least one knock-out ROD1 gene or plants comprising an RNA molecule inhibitory to at least one ROD1 gene can further be used to produce seeds, such as seeds with increased levels of C18:1, or seeds with decreased levels of C18:2 or SATS, or to produce seed oil with increased levels of C18:1, or with decreased levels of C18:2 or SATS.

The plants according to the invention may additionally contain an endogenous or a transgene, which confers herbicide resistance, such as the bar or pat gene, which confer resistance to glufosinate ammonium (Liberty®, Basta® or Ignite®); aryloxyalkanoate dioxygenase-12 to confer 2,4-D tolerance, or any modified EPSPS gene, such as a 2mEPSPS gene, or glyphosate acetyltransferase, which confer resistance to glyphosate (RoundupReady®), dicamba monooxygenase which confers dicamba resistance, any modified AHAS gene, which confers tolerance to ALS inhibitor herbicides, a hydroxyphenylpyruvate dioxygenase (HPPD) gene to confer tolerance to HPPD inhibitors, any gene encoding an insecticidal crystal protein (or cry gene), such as cry genes from *Bacillus thuringiensis* (for example the cry1Ac gene), to confer insect resistance, such as resistance to Lepidoptera. Further, the plants according to the invention may additionally contain an endogenous or a transgene which confers increased oil content or improved oil composition, such as and acyl-CoA:diacylglycerol acyltransferase, any fatty acid desaturase or fatty acyl-ACP thioesterase, or such as Vistive® low-linolenic soybeans, or such as trans fat free and reduced saturated fat Vistive® Gold soybeans.

Also, in accordance with the current invention, the plants according to the invention may be treated with the following insecticides, herbicides or fungicides or soybean seeds according to the invention may be coated with a coat comprising the following insecticides, herbicides or fungicides:

Soybean Herbicides:

Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Isoxaflutole.

Soybean Insecticides:

Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin.

Soybean Fungicides:

Azoxystrobin, Cyproconazole, Epoxiconazole, Flutriafol, Pyraclostrobin, Tebuconazole, Trifloxystrobin, Prothioconazole, Tetraconazole.

The knock-out rod1 gene according to the invention or the RNA inhibitory to a ROD1 gene according to the invention can be introduced by repeated back-crossing into commercial soybean cultivars such as but not limited to Soybean Cultivar 7631014 (US2009252860); Soybean Cultivar 7431014 (US2009252859); Soybean Cultivar 7925084 (US2009252858); Soybean Cultivar 7311153 (US2009252857); Soybean Cultivar S070159 (US2009252856); Soybean Cultivar 7535357 (US2009246353); Soybean Cultivar S070160 (US2009246352); Soybean Cultivar 26074414 (US2009249508); Soybean Cultivar 7509171 (US2009249507); Soybean Cultivar S070158 (US2009246351); Soybean Cultivar 7511119 (US2009249506); Soybean Cultivar 7113111 (US2009238945); Soybean cultivar S06-02RM018047 (U.S. Pat. No. 7,592,518); Soybean Cultivar 7013345 (US2009232957); Soybean Cultivar 7041461 (US2009235376); Soybean Cultivar 7549450 (US2009232956); Soybean Cultivar 7317090 (US2009232955); Soybean Cultivar 2N2V58015 (US2009226597); Soybean Cultivar 7243182 (US2009226596); Soybean Cultivar 7143182 (US2009226595); Soybean Cultivar 7043182 (US2009220673); Soybean Cultivar S070157 (US2009222950); Soybean Cultivar 306924721 (US2009220672); Soybean Cultivar 7614385 (US2009220671); Soybean Cultivar 7925118 (US2009214750); Soybean Cultivar 7821295 (US2009214749); Soybean Cultivar 7811336 (US2009214748); Soybean Cultivar S070150 (US2009214747); Soybean Cultivar 6214260 (US2009214746); Soybean Cultivar S070152 (US2009214745); Soybean Cultivar 7429331 (US2009214751); Soybean Cultivar 26034631 (US2009208634); Soybean cultivar S07-03JR108674 (U.S. Pat. No. 7,560,621); Soybean cultivar S07-03KL016279 (U.S. Pat. No. 7,560,620); Soybean cultivar S06-CL959411 (U.S. Pat. No. 7,554,017); SOYBEAN CULTIVAR SG3870NRR (US2009158453); SOYBEAN CULTIVAR HFPR-G (CA2645702); Soybean cultivar S06-02JR423016 (U.S. Pat. No. 7,521,606); Soybean cultivar S06-01JR119814 (U.S. Pat. No. 7,518,039); Soybean cultivar S06-01JR119448 (U.S. Pat. No. 7,518,038); Soybean Cultivar 6540220 (US2009055960); Soybean Cultivar S060292 (US2009055959); Soybean Cultivar S050228 (US2009055958); Soybean cultivar 506-02JR423003 (U.S. Pat. No. 7,491,873); Soybean cultivar S06-02JR423005 (U.S. Pat. No. 7,491,872); Soybean cultivar S06-02JR409114 (U.S. Pat. No. 7,485,782); Soybean cultivar S06-5E44056 (U.S. Pat. No. 7,473,823); Soybean cultivar (U.S. Pat. No. 7,470,835); Soybean cultivar 6910450 (US2008282369); SOYBEAN CULTIVAR 6223012 (U.S. Pat. No. 7,446,246); SOYBEAN CULTIVAR 6549250 (U.S. Pat. No. 7,446,245); Soybean Cultivar 17731225 (US2008271204); Soybean Cultivar 6928285 (US2008271203); Soybean Cultivar 6736054 (US2008271169); Soybean Cultivar S060299 (US2008271199); Soybean Cultivar S060294 (US2008271202); Soybean Cultivar 6943322 (US2008271201); Soybean cultivar 5343260 (US2008263719); Soybean cultivar 6439359 (US2008263704); Soybean cultivar 6238359 (US2008263703); Soybean cultivar 6547272 (US2008263702); Soybean cultivar 6929431 (US2008263701); Soybean cultivar 6703392 (US2008263700); Soybean cultivar 6044483 (US2008263699); Soybean cultivar S050224 (US2008263698); Soybean cultivar 6719022 (US2008263697); Soybean cultivar 5826056 (US2008263696); Soybean cultivar 6265047 (US2008263724); Soybean cultivar 6928331 (US2008263695); Soybean cultivar 6719331 (US2008263694); Soybean cultivar 6636454 (US2008263693); Soybean cultivar 6226454 (US2008263718); Soybean cultivar Q0073801 (US2008256657); SOYBEAN CULTIVAR 6326393 (US2008256652); SOYBEAN CULTIVAR 6408448 (US2008256651); Soybean cultivar 6449315 (US2008250524); Soybean cultivar S060296 (US2008250523); Soybean cultivar 6012078 (US2008250522); Soybean cultivar 6342078 (US2008250521); Soybean cultivar 6419156 (US2008250520); Soybean cultivar 5723264 (US2008250519); Soybean cultivar S050225 (US2008250518); Soybean cultivar S060298 (US2008244783); Soybean cultivar 6935331 (US2008244782); Soybean cultivar 6819456 (US2008244787); Soybean cultivar S060297 (US2008244781); Soybean cultivar 6135319 (US2008244786); Soybean cultivar 6819331 (US2008244780); Soybean cultivar 6137445 (US2008244779); Soybean cultivar 6917445 (US2008244778); Soybean cultivar 6111333 (US2008244777); Soybean Cultivar S050229 (US2008244776); Soybean Cultivar 6114011 (US2008244775); Soybean Cultivar 6900358 (US2008244784); Soybean Cultivar 6345184 (US2008244774); Soybean Cultivar 6836085 (US2008244773); Soybean Cultivar 6635047 (US2008244772); Soybean Cultivar 6139105 (US2008244771); SOYBEAN CULTIVAR 6434385 (US2008244770); SOYBEAN CULTIVAR S060295 (US2008244769); Soybean Cultivar 6035184 (US2008244768); Soybean Cultivar S060293 (US2008209590); Soybean Cultivar 6733322 (US2008209594); SOYBEAN CULTIVAR 6421326 (US2008209593); Soybean Cultivar S060077 (US2008209589); SOYBEAN CULTIVAR 6600375 (US2008209592); Soybean cultivar S06-CL821457 (U.S. Pat. No. 7,420,104); Soybean cultivar S07-02KG294306 (U.S. Pat. No. 7,414,178); Soybean cultivar S06-BA046119 (U.S. Pat. No. 7,414,175); Soybean cultivar S07-02KG294307 (U.S. Pat. No. 7,411,114); Soybean Cultivar SG3865N (US2008189802); Soybean cultivar 6701475 (U.S. Pat. No. 7,408,097); Soybean Cultivar 1335025 (US2008178316); Soybean Cultivar 1686017 (US2008178315); Soybean Cultivar 2388028 (US2008178314); Soybean Cultivar 2387029 (US2008178313); Soybean cultivar S06-WW152330 (U.S. Pat. No. 7,388,129); Soybean cultivar 6424090 (U.S. Pat. No. 7,385,118); Soybean cultivar 6723322 (U.S. Pat. No. 7,385,115); Soybean cultivar SG4377NRR (U.S. Pat. No. 7,385,114); Soybean cultivar S06-02JR111334 (U.S. Pat. No. 7,381,864); Soybean cultivar 6141287 (U.S. Pat. No. 7,378,577); Soybean cultivar MT110501 (U.S. Pat. No. 7,378,576); Soybean cultivar (U.S. Pat. No. 7,378,575); Soybean cultivar S06-WW169267 (U.S. Pat. No. 7,375,261); Soybean cultivar 6223392 (U.S. Pat. No. 7,371,939); Soybean cultivar S06-CL968413 (U.S. Pat. No. 7,371,937);

Soybean cultivar S06-CL951107 (U.S. Pat. No. 7,368,636); Soybean cultivar S06-MT9152077 (U.S. Pat. No. 7,361,810); Soybean Cultivar 4211676 (US2008092253); Soybean cultivar S06-M059029 (U.S. Pat. No. 7,355,101); Soybean Cultivar 6548193 (U.S. Pat. No. 7,345,228); Soybean cultivar 6440261 (U.S. Pat. No. 7,345,227); Soybean cultivar S060291 (U.S. Pat. No. 7,342,151); Soybean cultivar S06-MT9206166 (U.S. Pat. No. 7,339,094); Soybean cultivar S06-WW013107 (U.S. Pat. No. 7,339,093); Soybean cultivar S06-M03256 (U.S. Pat. No. 7,335,820); Soybean cultivar 6134466 (U.S. Pat. No. 7,332,656); Soybean cultivar S06-01JR123373 (U.S. Pat. No. 7,329,800); Soybean cultivar S06-MT9211059 (U.S. Pat. No. 7,326,831); Soybean cultivar 26170838 (US2008016590); Soybean cultivar 306612412 (US2008016588); Soybean cultivar 26660135 (US2008016587); Soybean cultivar 306734323 (US2008016586); Soybean cultivar S06-01JR122235 (U.S. Pat. No. 7,317,144); SOYBEAN CULTIVAR 5900450 (U.S. Pat. No. 7,314,986); Soybean cultivar S06-MT116260 (U.S. Pat. No. 7,314,984); Soybean cultivar S06-SJ143606 (U.S. Pat. No. 7,312,381); Soybean cultivar S06-98181-G01-35167 (U.S. Pat. No. 7,309,819); SOYBEAN CULTIVAR 26082635 (U.S. Pat. No. 7,304,219); Soybean cultivar BA922834 (U.S. Pat. No. 7,304,217); Soybean cultivar 01JR123480 (U.S. Pat. No. 7,304,216); Soybean cultivar M061422 (U.S. Pat. No. 7,304,215); Soybean cultivar 17082821 (US2007277262); Soybean cultivar 17621620 (US2007277261); Soybean cultivar 00977706 (US2007277260); Soybean cultivar S060182 (US2007277259); Soybean cultivar 26312034 (U.S. Pat. No. 7,301,078); Soybean cultivar 26143837 (U.S. Pat. No. 7,301,077); Soybean cultivar 435.TCS (US2007271626); Soybean cultivar 495.RC (US2007271625); Soybean cultivar 5306230 (U.S. Pat. No. 7,297,845); Soybean cultivar S06-WW167686 (U.S. Pat. No. 7,291,772);

Soybean cultivar 6141145 (US2007245426); Soybean cultivar S050232 (US2007226829); Soybean cultivar 5333301 (US2007226828); SOYBEAN CULTIVAR S050215 (US2007226827); SOYBEAN CULTIVAR 3235020 (US2007226826); Soybean cultivar 5720482 (US2007226825); Soybean cultivar S050216 (US2007226824); Soybean Cultivar 5512112 (US2007226823); Soybean cultivar 3233021 (US2007226822); SOYBEAN CULTIVAR 1336024 (US2007226821); Soybean cultivar 5348287 (US2007226820); Soybean cultivar 5204220 (US2007226819); Soybean cultivar 6188027 (US2007226818); Soybean cultivar 4183026 (US2007226817); Soybean cultivar S06-WW157958 (U.S. Pat. No. 7,271,325); Soybean cultivar 5733056 (US2007209091); Soybean cultivar 90501911 (US2007209090); Soybean cultivar S050221 (US2007204361); SOYBEAN CULTIVAR 5802205 (US2007204360); Soybean cultivar 1000642 (US2007204359); Soybean cultivar 5420128 (US2007204358); Soybean cultivar S050222 (US2007199094); Soybean cultivar S050217 (US2007199093); SOYBEAN CULTIVAR S050223 (US2007199092); Soybean cultivar S050218 (US2007199091);

Soybean cultivar 5419227 (US2007199089); Soybean cultivar 5319227 (US2007199088); Soybean cultivar 5723045 (US2007199087); SOYBEAN CULTIVAR 5051007 (US2007199086); Soybean cultivar 5826175 (US2007192893); Soybean cultivar S050231 (US2007192892); SOYBEAN CULTIVAR 5826376 (US2007192891); SOYBEAN CULTIVAR 5628386 (US2007192890); Soybean cultivar 5138236 (US2007186307); Soybean cultivar 5608398 (US2007186306); SOYBEAN CULTIVAR S050230 (US2007186305); SOYBEAN CULTIVAR 5624126 (US2007180561); SOYBEAN CULTIVAR 5019225 (US2007180560); SOYBEAN CULTIVAR 5549483 (US2007180559); SOYBEAN CULTIVAR 4189010 (US2007180551); SOYBEAN CULTIVAR 1486018 (US2007180550); SOYBEAN CULTIVAR S050235 (US2007180549); SOYBEAN CULTIVAR 5023230 (US2007180548); SOYBEAN CULTIVAR S050238 (US2007174930); SOYBEAN CULTIVAR 5830261 (US2007174928); SOYBEAN CULTIVAR S050226 (U.S. Pat. No. 7,247,772); SOYBEAN CULTIVAR 5806063 (U.S. Pat. No. 7,247,771); SOYBEAN CULTIVAR S050233 (U.S. Pat. No. 7,244,881); SOYBEAN CULTIVAR 5726085 (U.S. Pat. No. 7,241,939); Soybean cultivar MT000792 (U.S. Pat. No. 7,238,867); Soybean cultivar 5521161 (U.S. Pat. No. 7,235,718); Soybean cultivar WW109447 (U.S. Pat. No. 7,235,717); Soybean cultivar BA947474 (U.S. Pat. No. 7,220,898); Soybean cultivar 5939002 (U.S. Pat. No. 7,217,870); Soybean cultivar 5726175 (U.S. Pat. No. 7,217,869); Soybean cultivar 5432082 (U.S. Pat. No. 7,217,868); Soybean cultivar SG085ORR (U.S. Pat. No. 7,211,715); Soybean cultivar SG1750NRR (U.S. Pat. No. 7,208,658); Soybean cultivar MT017827 (U.S. Pat. No. 7,208,657); Soybean cultivar 4N2V74028 (U.S. Pat. No. 7,205,458); Soybean cultivar CL431203 (U.S. Pat. No. 7,202,400); Soybean cultivar 4N0S63222 (U.S. Pat. No. 7,199,288); Soybean cultivar 5520279 (U.S. Pat. No. 7,196,253); Soybean cultivar 5834401 (U.S. Pat. No. 7,196,252); Soybean cultivar 5621161 (U.S. Pat. No. 7,196,251); Soybean cultivar CL722114 (U.S. Pat. No. 7,196,250); Soybean cultivar 5741081 (U.S. Pat. No. 7,193,140); Soybean cultivar CL727422 (U.S. Pat. No. 7,186,895); Soybean cultivar 4N2V55022 (U.S. Pat. No. 7,183,468); Soybean cultivar 5083011 (U.S. Pat. No. 7,173,169); Soybean cultivar 5626085 (U.S. Pat. No. 7,169,976); SOYBEAN CULTIVAR S050051 (U.S. Pat. No. 7,169,974); SOYBEAN CULTIVAR 4506816 (US2006294626); Soybean cultivar WW152201 (U.S. Pat. No. 7,132,594); Soybean cultivar CL727636 (U.S. Pat. No. 7,132,593); Soybean cultivar M08851 (U.S. Pat. No. 7,126,047); Soybean cultivar 4324401 (U.S. Pat. No. 7,105,728); Soybean cultivar S050164 (U.S. Pat. No. 7,105,727); Soybean cultivar 4136015 (US2006195931); Soybean cultivar 3133014 (US2006195930); Soybean cultivar S040132 (US2006195929); Soybean Cultivar 4328386 (US2006195928); Soybean cultivar 1339013 (US2006195927); SOYBEAN CULTIVAR 4423183 (US2006195925); Soybean cultivar S040131 (US2006195924); Soybean cultivar 4929388 (US2006195923); Soybean cultivar 4817034 (US2006195922); Soybean cultivar 4916816 (U.S. Pat. No. 7,098,385); Soybean cultivar 4713487 (US2006191032); Soybean cultivar 4348019 (US2006191031); Soybean cultivar S040122 (US2006191030); Soybean cultivar S040133 (US2006185031); Soybean cultivar CL821418 (U.S. Pat. No. 7,091,404); SOYBEAN CULTIVAR 4441080 (U.S. Pat. No. 7,091,403); Soybean cultivar 4805442 (US2006179509); Soybean cultivar 4921237 (US2006179508); Soybean cultivar 4417380 (US2006174369); Soybean cultivar 4405070 (US2006174368); Soybean cultivar 4417779 (U.S. Pat. No. 7,084,328); Soybean cultivar S040125 (US2006168678); Soybean cultivar 4909380 (U.S. Pat. No. 7,081,572); Soybean cultivar S050162 (U.S. Pat. No. 7,081,571); Soybean cultivar 6084016 (U.S. Pat. No. 7,081,570); Soybean cultivar S050163 (U.S. Pat. No. 7,078,600); Soybean cultivar S040135 (U.S. Pat. No. 7,078,598); Soybean cultivar S040117 (U.S. Pat. No. 7,078,597); Soybean cultivar M03393 (U.S. Pat. No. 7,071,391); Soybean cultivar 4145306 (U.S. Pat. No. 7,064,253); Soybean cultivar 900213 (US2006117405); Soybean cultivar 1000126 (US2006117404); Soybean cultivar 901023 (US2006117403); Soybean cultivar S040130 (U.S. Pat. No. 7,053,280); Soybean cultivar 4706198 (U.S. Pat. No. 7,053,279); Soybean cultivar S040118 (U.S. Pat. No. 7,053,278); Soybean cultivar S040119 (U.S. Pat. No. 7,053,277); Soybean cultivar S040123 (U.S. Pat. No. 7,053,276); Soybean cultivar 4442112 (U.S. Pat. No. 7,049,497); SOYBEAN CULTIVAR 917013 (U.S. Pat. No. 7,045,689); Soybean cultivar S040124 (U.S. Pat. No. 7,045,691); Soybean cultivar 4238491 (U.S. Pat. No. 7,045,690); Soybean cultivar S010136 (U.S. Pat. No. 7,041,882); Soybean cultivar 900613 (U.S. Pat. No. 7,030,297); Soybean cultivar 4337175 (U.S. Pat. No. 7,030,301); Soybean cultivar S040121 (U.S. Pat. No. 7,030,300); Soybean cultivar 4216033 (U.S. Pat. No. 7,030,299); Soybean cultivar S040128 (U.S. Pat. No. 7,022,901); Soybean cultivar S040120 (U.S. Pat. No. 7,022,900); Soybean cultivar S040127 (U.S. Pat. No. 7,019,199); Soybean cultivar S040134 (U.S. Pat. No. 7,015,378); Soybean cultivar S040129 (U.S. Pat. No. 7,015,377); Soybean cultivar 4513420 (U.S. Pat. No. 7,005,564); Soybean cultivar 943013 (US2006031958); Soybean cultivar S030136 (US2006021081); Soybean cultivar 927013 (US2006021080); Soybean cultivar 1000109 (US2006015962); Soybean cultivar 90046112 (US2006010530); Soybean cultivar 90897327 (US2006010529); Soybean cultivar 90362421 (US2006010528); Soybean cultivar 03022253 (US2006010527); Soybean cultivar 02022433 (US2006010526); Soybean cultivar 02022323 (US2006010525); Soybean cultivar 02912951 (US2006010524); Soybean cultivar 0102115 (US2006010523); Soybean cultivar 915034 (US2006010522); Soybean cultivar 0509255 (US2006010521); Soybean cultivar 4803070 (U.S. Pat. No. 6,982,368); Soybean cultivar 4704310 (U.S. Pat. No. 6,979,762); Soybean cultivar SJ919784 (US2005268362); Soybean cultivar CL615261 (US2005268361); Novel soybean (US2004199964); Soybean cultivar 0509214 (US2005210542); Soybean cultivar 70826751 (US2005193442); Soybean cultivar 0509243 (US2005193441); Soybean cultivar 0509246 (US2005193440); Soybean cultivar 0509253 (US2005193439); Soybean cultivar 0509247 (US2005193438); Soybean cultivar 0509252 (US2005193437); Soybean cultivar 0509241 (US2005193436); Soybean cultivar 0509249 (U.S. Pat. No. 6,884,927); Soybean cultivar 0509244 (US2005183158); Soybean cultivar 0509240 (US2005183157); Soybean cultivar 0509239 (US2005183156); Soybean cultivar 0509254 (US2005183155); Soybean cultivar 0509245 (US2005183154); Soybean cultivar 0509251 (US2005183153); Soybean cultivar 4283008 (U.S. Pat. No. 6,888,050); Soybean cultivar 2386009 (US2005183152); Soybean cultivar 3282002 (U.S. Pat. No. 6,870,080); Soybean cultivar 0509248 (US2005183151); Soybean cultivar 5091007 (U.S. Pat. No. 6,906,249( ); Soybean cultivar 0509236 (US2005166281); Soybean cultivar 0509235 (US2005166280); Soybean cultivar 0509237 (US2005166279); Soybean cultivar SG5322NRR (US2005164390); Soybean cultivar SG5030NRR (US2005166278); Soybean cultivar SG4911NRR (US2005166277); Soybean cultivar S030153 (US2005160504); Soybean cultivar S030158 (US2005144680); SOYBEAN CULTIVAR S030160 (US2005144679); Soybean cultivar S030161 (US2005144678); Soybean cultivar S030157 (US2005144677); Soybean cultivar S030155 (US2005144676); Soybean cultivar S030156 (US2005144675); SOYBEAN CULTIVAR S030159 (US2005144674); Soybean cultivar S030154 (U.S. Pat. No. 6,900,376); Soybean cultivar S020030 (US2005114929); Soybean cultivar S030010 (US2005114928); Soybean cultivar SG1431RR (US2005097629); SOYBEAN CULTIVAR SG1330NRR (US2005097642); Soybean cultivar S030150 (US2005071900); SOYBEAN CULTIVAR S022209 (US2005050601); Soybean cultivar S022217 (US2005050600); Soybean cultivar S022219 (US2005050599); Soybean cultivar S030151 (US2005050598); Soybean cultivar 0491735 (US2005022272); Soybean cultivar S022218 (US2005022271); Soybean cultivar 6190006 (US2004268447); Soybean cultivar SG112ORR (US2004250316); Soybean cultivar 0487681 (US2004237153); Soybean cultivar 0491717 (US2004237152); Soybean cultivar S022220 (US2004237151); Soybean cultivar 0491715 (US2004237150); Soybean cultivar 0491712 (US2004237149); Soybean cultivar 0491718 (US2004237148); Soybean cultivar 99271316 (US2004221344); Soybean cultivar S022212 (US2004221343); Soybean cultivar 0491737 (US2004221342); Soybean cultivar S022211 (US2004221341); Soybean cultivar S022210 (US2004221340); Soybean cultivar S022213 (US2004221339); Soybean cultivar 0491725 (US2004221346); Soybean cultivar 03129016 (US2004221329); Soybean cultivar S022208 (US2004221328); Soybean cultivar S022207 (US2004221345); Soybean cultivar 02932 (US2004210968); Soybean cultivar 94137321 (US2004205862); Soybean cultivar 94106224 (US2004205861); Soybean cultivar 94143901 (US2004205859); SOYBEAN CULTIVAR 0487685 (US2004205858); SOYBEAN CULTIVAR 92440927 (US2004205857); Soybean cultivar 0487686 (US2004205856); Soybean cultivar S022215 (US2004205855); Soybean cultivar S022214 (US2004205854); SOYBEAN CULTIVAR 0491726 (US2004205849); SOYBEAN CULTIVAR 92478609 (US2004205853); Soybean cultivar 922013 (U.S. Pat. No. 6,781,040); SOYBEAN CULTIVAR 0491727 (US2004205852); SOYBEAN CULTIVAR 0491728 (US2004205851); Soybean cultivar 1465003 (US2004098766); Soybean cultivar 3186004 (US2004019936); Soybean cultivar 7085005 (US2004205850); Soybean cultivar S022204 (US2004199958); Soybean cultivar S022206 (US2004199957); Soybean cultivar 0491731 (US2004199956); Soybean cultivar 0491733 (US2004199955); Soybean cultivar 0491738 (US2004199954); Soybean cultivar 0491732 (US2004199953); Soybean cultivar 0491729 (US2004199952); Soybean cultivar S020011 (US2004199951); Soybean cultivar 0491739 (US2004199950); Soybean cultivar 0491730

(US2004199949); Soybean cultivar 13873 (US2004199948); Soybean cultivar 954011 (US2004181822); Soybean cultivar 010022 (US2004181831); Soybean cultivar 4181001 (US2003229926); Soybean cultivar 0491721 (US2004168228); Soybean cultivar 0491723 (U.S. Pat. No. 6,911,581); Soybean cultivar 0491716 (US2004168226); Soybean cultivar 0491713 (US2004168225); Soybean cultivar 0491711 (US2004168224); Soybean cultivar 0491722 (US2004168223); Soybean cultivar 0491724 (US2004168222); Soybean cultivar 0491720 (US2004168221); Soybean cultivar 0487682 (US2004168220); Soybean cultivar 0491714 (US2004168219); Soybean cultivar 0491719 (US2004168218); Soybean cultivar DP 5634 RR (US2003177540); Soybean Cultivar S56-D7 (US2004098765); Soybean cultivar 926877 (US2004064859); Soybean cultivar SE73753 (US2004055059); Soybean cultivar SN83594 (US2004055058); Soybean cultivar SE71112 (US2004055056); Soybean cultivar SE73090 (US2004055054); Soybean cultivar SN79526 (US2004055053); Soybean cultivar SW90702 (US2004055052); Soybean cultivar SN79525 (US2004055051); Soybean cultivar SE90345 (US2004055050); Soybean cultivar 0149928 (US2004055049); Soybean cultivar SN83780 (US2004055048); Soybean cultivar 0053840 (US2004055047); Soybean cultivar 924001 (US2004055046); Soybean cultivar 0004747 (US2004055057); Soybean cultivar 0037357 (US2004055045); Soybean cultivar SN83366 (US2004055044); Soybean cultivar SN76208 (US2004055043); Soybean cultivar 0037370 (US2004055042); Soybean cultivar SX95512 (US2004049821); Soybean cultivar 0096008 (US2004049820); Soybean cultivar SN83544 (US2004049819); Soybean cultivar 0088401 (US2004049818); Soybean cultivar SN64195 (US2004049817); Soybean cultivar 0034754 (US2004049816); Soybean cultivar SN71173 (US2004049815); Soybean cultivar SN83211 (US2004049814); Soybean cultivar 92422749 (US2004045058); Soybean cultivar 0120311 (US2004045057); Soybean cultivar 5010344 (US2004003438); Soybean cultivar 70876922 (US2004003437); Soybean cultivar 924496 (US2004003436); Soybean cultivar 19705120 (US2003237116); Soybean cultivar 19704220 (US2003235914); Soybean Cultivar 19704280 (US2003237115); Soybean cultivar 19704210 (US2003237114); Soybean cultivar S37-N4 (US2003237113); Soybean cultivar 19602310 (US2003233685); Soybean cultivar 19704120 (US2003233684); Soybean cultivar 19704230 (US2003233683); Soybean cultivar 1000126 (US2003233682); Soybean cultivar 93831526 (US2003221226); Soybean cultivar 0322581 (US2003221225); Soybean cultivar 0332149 (US2003213028); Soybean cultivar 0332144 (US2003213027); Soybean cultivar 924788 (US2003213026); Soybean cultivar 924861 (US2003213025); Soybean cultivar 928070 (US2003213024); Soybean cultivar 5010354 (US2003213023); Soybean cultivar 5010360 (US2003213022); Soybean cultivar 5010361 (US2003213021); Soybean cultivar 5010363 (US2003213020); Soybean cultivar 5010364 (US2003213019); Soybean cultivar 0332148 (US2003208805); Soybean cultivar 0332147 (US2003208804); Soybean cultivar 0332146 (US2003208803); Soybean cultivar 0332135 (US2003208802); Soybean cultivar 1000144 (US2003208801); Soybean cultivar 0332143 (US2003208800); Soybean cultivar 0332145 (US2003208799); Soybean cultivar 5010345 (US2003204884); Soybean cultivar 0332131 (US2003204883); Soybean cultivar 0332130 (US2003204882); Soybean cultivar 0332129 (US2003204881); Soybean cultivar 0332122 (US2003204880); Soybean cultivar 5010350 (US2003204879); Soybean cultivar 5010355 (US2003204878); Soybean cultivar 031766 (US2003204877); Soybean cultivar S010353 (US2003204876); Soybean cultivar 0322580 (US2003200579); Soybean cultivar 0322579 (US2003200578); Soybean cultivar S010347 (US2003200577); Soybean cultivar S010349 (US2003200576); Soybean cultivar 0332141 (US2003200575); Soybean cultivar 0332142 (US2003200574); Soybean Cultivar 0332133 (US2003200573); Soybean cultivar 0332134 (US2003200572); Soybean cultivar 0332139 (US2003200571); Soybean cultivar 0332137 (US2003200570); Soybean variety XB33U08 (U.S. Pat. No. 7,598,435); Soybean variety XB27D08 (U.S. Pat. No. 7,592,519); Soybean variety XB41M08 (U.S. Pat. No. 7,589,261); Soybean variety XB05J08 (U.S. Pat. No. 7,589,260); Soybean variety XB33T08 (U.S. Pat. No. 7,589,259); Soybean variety XB30Y08 (U.S. Pat. No. 7,586,025); Soybean variety XB40U08 (U.S. Pat. No. 7,582,813); Soybean variety XB29M08 (U.S. Pat. No. 7,582,811); SOYBEAN VARIETY 93Y10 (US2009144843); SOYBEAN VARIETY D4325666 (US2009055957); SOYBEAN VARIETY D4125897 (US2009055956); SOYBEAN VARIETY D4698573 (US2009055955); SOYBEAN VARIETY D4356652 (US2009019592); SOYBEAN VARIETY D4456885 (US2009019591); SOYBEAN VARIETY D4698013 (US2009019590); SOYBEAN VARIETY D4637114 (US2009019589); SOYBEAN VARIETY D4102367 (US2009019595); SOYBEAN VARIETY D4266582 (US2009019594); SOYBEAN VARIETY D4422801 (US2009019593); SOYBEAN VARIETY D4520980 (US2009019588); SOYBEAN VARIETY D4521369 (US2009019587); SOYBEAN VARIETY D4223057 (US2009019586); SOYBEAN VARIETY D4682156 (US2009019585); SOYBEAN VARIETY D4233569 (US2009019584); SOYBEAN VARIETY D4925614 (US2009019583); SOYBEAN VARIETY D4203144 (US2009019604); SOYBEAN VARIETY D4102536 (US2009019582); SOYBEAN VARIETY D4865324 (US2009019581); SOYBEAN VARIETY D4825495 (US2009019580); SOYBEAN VARIETY D4659251 (US2009019579); SOYBEAN VARIETY D4258962 (US2009019578); SOYBEAN VARIETY D4253969 (US2009019577); SOYBEAN VARIETY D4696658 (US2009019603); SOYBEAN VARIETY D4256925 (US2009019576); SOYBEAN VARIETY D4253681 (US2009019575); SOYBEAN VARIETY D4789254 (US2009019574); SOYBEAN VARIETY D4713125 (US2009019573); SOYBEAN VARIETY D4526223 (US2009019572); SOYBEAN VARIETY D4556201 (US2009019571); SOYBEAN VARIETY D4012368 (US2009019570); SOYBEAN VARIETY D4452019 (US2009019569); SOYBEAN VARIETY D4201483 (US2009019568); SOYBEAN VARIETY D4463892 (US2009019567); SOYBEAN VARIETY D4159630 (US2009019566); SOYBEAN VARIETY D4470236 (US2009019565); SOYBEAN VARIETY D4063284 (US2009019564); SOYBEAN VARIETY D4021792 (US2009013429); SOYBEAN VARIETY D4902530 (US2009013428); SOYBEAN VARIETY D4367012 (US2009013427); SOYBEAN VARIETY D4923560 (US2009013426); SOYBEAN VARIETY D4253854 (US2009013425); SOYBEAN VARIETY D4210110 (US2009007290); SOYBEAN VARIETY D4523081 (US2009007289); SOYBEAN VARIETY D4328762 (US2009007288); SOYBEAN VARIETY D4483789 (US2009007287); SOYBEAN VARIETY D4311702 (US2009007286); SOYBEAN VARIETY D4127789 (US2008313765); SOYBEAN VARIETY D4361423 (US2008313764); SOYBEAN VARIETY D4208814 (US2008313763); SOYBEAN VARIETY D4201139 (US2008313762); SOYBEAN VARIETY D4120384 (US2008313761); SOYBEAN VARIETY D4572906 (US2008313760); SOYBEAN VARIETY D4301279 (US2008313759); SOYBEAN VARIETY D4422957 (US2008313758); SOYBEAN VARIETY D4256958 (US2008313757); SOYBEAN VARIETY 4074328 (US2008282366); SOYBEAN VARIETY XB47Q06 (US2008244767); SOYBEAN VARIETY XB26R06 (US2008244766); SOYBEAN VARIETY 4991629 (US2008216190); SOYBEAN VARIETY 4158090 (US2008216189); Soybean Variety XB40K07 (US2008209582); SOYBEAN VARIETY D0069201 (US2008178345); SOYBEAN VARIETY D0064801 (US2008178320); SOYBEAN VARIETY D0063801 (US2008178344); SOYBEAN VARIETY D0061501 (US2008178343); SOYBEAN VARIETY 4938051 (US2008178319); SOYBEAN VARIETY 4880500 (US2008178318); SOYBEAN VARIETY 4835953 (US2008178317); SOYBEAN VARIETY 4684181 (US2008178342); SOYBEAN VARIETY 4427363 (US2008178340); SOYBEAN VARIETY 4676311 (US2008178339); SOYBEAN VARIETY 4953710 (US2008178337); SOYBEAN VARIETY 4857548 (US2008178336); SOYBEAN VARIETY 4551757 (US2008178335); SOYBEAN VARIETY 4027271 (US2008178334); SOYBEAN VARIETY 4274171 (US2008178333); SOYBEAN VARIETY 0341931 (US2008178332); SOYBEAN VARIETY 4282159 (US2008178331); SOYBEAN VARIETY 4852004 (US2008178330); SOYBEAN VARIETY 4688589 (US2008178329); SOYBEAN VARIETY 4614131 (US2008178327); SOYBEAN VARIETY 4201823 (US2008178326); SOYBEAN VARIETY 92M22 (US2008178350); SOYBEAN VARIETY 4174206 (US2008178322); SOYBEAN VARIETY 4305498 (US2008178321); SOYBEAN VARIETY 4423586 (US2008172761); SOYBEAN VARIETY 4568207 (US2008172756); SOYBEAN VARIETY 4840308 (US2008172755); SOYBEAN VARIETY 4256323 (US2008172754); SOYBEAN VARIETY 4789516 (U.S. Pat. No. 7,399,907); SOYBEAN VARIETY 90Y40 (US2008168581); SOYBEAN VARIETY 4959932 (U.S. Pat. No. 7,396,983); SOYBEAN VARIETY 4062885 (U.S. Pat. No. 7,394,000); Soybean variety 4858197 (U.S. Pat. No. 7,390,940); Soybean variety 4092390 (U.S. Pat. No. 7,390,939); Soybean variety 4735486 (U.S. Pat. No. 7,390,938); Soybean variety 4219527 (U.S. Pat. No. 7,388,132); Soybean variety 4599695 (U.S. Pat. No. 7,388,131); Soybean variety 4554257 (U.S. Pat. No. 7,388,130); Soybean variety 4896902 (U.S. Pat. No. 7,385,113); Soybean variety 4367308 (U.S. Pat. No. 7,385,112); Soybean variety 4589609 (U.S. Pat. No. 7,385,111); Soybean variety 4640250 (U.S. Pat. No. 7,385,110); Soybean variety 4540394 (U.S. Pat. No. 7,385,109); Soybean variety 4297661 (U.S. Pat. No. 7,385,108); Soybean variety 4958786 (U.S. Pat. No. 7,381,866); Soybean variety 4440685 (U.S. Pat. No. 7,375,262); Soybean variety 4008211 (U.S. Pat. No. 7,371,938); Soybean variety 4778469 (U.S. Pat. No. 7,368,637); Soybean variety 4766295 (U.S. Pat. No. 7,355,103); Soybean variety 4436909 (U.S. Pat. No. 7,355,102); Soybean variety 4812469 (U.S. Pat. No. 7,351,886); Soybean variety 4761767 (U.S. Pat. No. 7,351,885); Soybean variety 4142393 (U.S. Pat. No. 7,329,801); Soybean variety 4502135 (U.S. Pat. No. 7,326,832); Soybean variety 4353363 (U.S. Pat. No. 7,321,082); Soybean variety 91B42 (U.S. Pat. No. 7,317,143); SOYBEAN VARIETY 0330739 (US2007271622); Soybean variety 0384279 (U.S. Pat. No. 7,294,768); SOYBEAN VARIETY 4175567 (US2007256187); SOYBEAN VARIETY 4336643 (US2007256186); SOYBEAN VARIETY 4671685 (US2007256185); SOYBEAN VARIETY 4309194 (US2007256190); SOYBEAN VARIETY 0330738 (US2007256184); SOYBEAN VARIETY 0045477 (US2007256183); SOYBEAN VARIETY 0437973 (US2007256182); SOYBEAN VARIETY 0457028 (US2007256181); SOYBEAN VARIETY 0367478 (US2007256180); SOYBEAN VARIETY 0358232 (US2007256179); SOYBEAN VARIETY 0417158 (US2007256178); SOYBEAN VARIETY 4559809 (US2007256177); SOYBEAN VARIETY 0196172 (US2007256176); SOYBEAN VARIETY 4785923 (US2007256175); SOYBEAN VARIETY 4587513 (US2007256174); SOYBEAN VARIETY 0409670 (US2007256173); SOYBEAN VARIETY 4010165 (US2007256172); SOYBEAN VARIETY 0421133 (US2007256171); SOYBEAN VARIETY 0240187 (US2007256170); SOYBEAN VARIETY 0387907 (US2007256169); SOYBEAN VARIETY 0232405 (US2007256168); SOYBEAN VARIETY 0146529 (US2007256167); SOYBEAN VARIETY 4788561 (US2007256166); SOYBEAN VARIETY 457114 (US2007256165); SOYBEAN VARIETY 0149217 (US2007256164); SOYBEAN VARIETY 4247825 (US2007254366); SOYBEAN VARIETY 0212938 (US2007256163); SOYBEAN VARIETY 0146565 (US2007256162); SOYBEAN VARIETY 4647672 (US2007256161); SOYBEAN VARIETY 0215818 (US2007256160); SOYBEAN VARIETY 0384531 (US2007256159); SOYBEAN VARIETY 4878185 (US2007254365); SOYBEAN VARIETY 4498438 (US2007256158); SOYBEAN VARIETY 0436052 (US2007256157); SOYBEAN VARIETY 4782157 (US2007256156); SOYBEAN VARIETY 0385457 (US2007256155); SOYBEAN VARIETY 0385240 (US2007256154); SOYBEAN VARIETY 4735316 (US2007256153); SOYBEAN VARIETY 0277524 (US2007256152); SOYBEAN VARIETY 0276951 (US2007256151); Soybean Variety XB37L07 (US2007245429); Soybean Variety XB35X07 (US2007226837); Soybean Variety XB35S07 (US2007226836); Soybean Variety XB35F07 (US2007226835); Soybean Variety XB34R07 (US2007226834); Soybean Variety XB34L07 (US2007226833); Soybean Variety XB34D07

(US2007226832); Soybean Variety XB33G07 (US2007226831); Soybean Variety 98Y11 (US2007169220); Soybean variety 0137335 (U.S. Pat. No. 7,241,941); Soybean Variety XB15E07 (US2007150980); Soybean Variety 92M52 (US2007150979); Soybean Variety XB47R07 (US2007136888); Soybean Variety XB46V07 (US2007136887); Soybean Variety XB57E07 (US2007136886); Soybean Variety XB54X07 (US2007136885); Soybean Variety XB54V07 (US2007136884); Soybean Variety XB52Q07 (US2007136883); Soybean Variety XB37M07 (US2007136882); Soybean Variety XB37J07 (US2007136881); Soybean Variety XB34Q07 (US2007136880); Soybean Variety XB32S07 (US2007136879); Soybean Variety XB32J07 (US2007136878); Soybean Variety XB31R07 (US2007136877); Soybean Variety XB31J07 (US2007136876); Soybean Variety XB29K07 (US2007136875); Soybean Variety XB31H07 (US2007136874); Soybean Variety XB30G07 (US2007136873); Soybean Variety XB30E07 (US2007136872); Soybean Variety XB25E07 (US2007136871); Soybean Variety XB26X07 (US2007136870); Soybean Variety XB23L07 (US2007136869); Soybean Variety XB19Z07 (US2007136868); Soybean Variety XB19E07 (US2007136867); Soybean Variety XB18M07 (US2007136866); Soybean Variety XB18K07 (US2007136865); Soybean Variety XB18J07 (US2007136864); Soybean Variety XB17W07 (US2007136863); Soybean Variety XB17U07 (US2007136862); Soybean Variety XB15B07 (US2007136861); Soybean Variety XB12R07 (US2007136860); Soybean Variety XB11J07 (US2007136859); Soybean Variety XB04E07 (US2007136858); Soybean Variety XB02K07 (US2007136857); Soybean Variety XB49V07 (US2007136856); Soybean Variety XB48X07 (US2007136855); Soybean Variety 92M75 (US2007136854); Soybean Variety XB48W07 (US2007136853); Soybean Variety XB44G07 (US2007136852); Soybean Variety XB42K07 (US2007136851); Soybean Variety XB42H07 (US2007136850); Soybean Variety XB41J07 (US2007136849); Soybean Variety XB40Y07 (US2007136848); Soybean Variety XB40X07 (US2007136847); Soybean Variety XB39E07 (US2007136846); Soybean Variety XB38W07 (US2007136845); Soybean Variety XB38S07 (US2007136844); Soybean Variety XB23V07 (US2007136843); Soybean Variety XB31M07 (US2007130652); Soybean Variety XB28E07 (US2007130651); Soybean Variety XB25S07 (US2007130650); Soybean Variety XB21N07 (US2007130649); Soybean Variety XB03Q07 (US2007130648); Soybean Variety XB49Q07 (US2007130647); Soybean Variety XB06M07 (US2007130646); Soybean variety S04-97130-15-02 (U.S. Pat. No. 7,196,249); Soybean variety S04-97026-N99-42648-01 (U.S. Pat. No. 7,189,896); Soybean variety S05-97016-G99-21212 (U.S. Pat. No. 7,186,894); Soybean variety S05-99048-19 (U.S. Pat. No. 7,164,064); Soybean variety 92B14 (U.S. Pat. No. 7,161,065); Soybean Variety 98R31 (US2007006350); Soybean variety S05-97177-N00-22972 (U.S. Pat. No. 7,132,592); Soybean variety XB25G06 (US2006225160); Soybean variety 91M70 (US2006174381); Soybean variety XB24R06 (US2006162029); Soybean variety S03-95368-N98-52902 (U.S. Pat. No. 7,078,594); Soybean variety S05-97130-51 (U.S. Pat. No. 7,078,599); Soybean variety XB11L06 (US2006130187); Soybean variety 94B13 (U.S. Pat. No. 7,064,251); Soybean variety 94B74 (U.S. Pat. No. 7,064,250); Soybean variety XB27J06 (US2006112462); Soybean variety XB29N06 (US2006112460); Soybean variety XB28T06 (US2006112459); Soybean variety XB16W06 (US2006112458); Soybean variety XB18C06 (US2006112456); Soybean variety XB10M06 (US2006107391); Soybean variety XB06K06 (US2006107390); Soybean variety XB28V06 (US2006107389); Soybean variety XB004A06 (US2006107388); Soybean variety XB12L06 (US2006107387); Soybean variety XB005A06 (US2006107386); Soybean variety XB25H06 (US2006107385); Soybean variety XB39W06 (US2006107384); Soybean variety XB27K06 (US2006107383); Soybean variety XB29R06 (US2006107382); Soybean variety XB16S06 (US2006107381); Soybean variety XB36V06 (US2006107380); Soybean variety XB07N06 (US2006107379); Soybean variety XB23H06 (US2006107378); Soybean variety XB35C06 (US2006107377); Soybean variety XB32L06 (US2006107376); Soybean variety XB58P06 (US2006107375); Soybean variety XB36M06 (US2006107374); Soybean variety XB22G06 (US2006107373); Soybean variety XB36Q06 (US2006107372); Soybean variety 91M61 (US2006107371); Soybean variety XB32A06 (US2006107370); Soybean variety XB19V06 (US2006107369); Soybean variety XB43C06 (US2006107368); Soybean variety XB22N06 (US2006107367); Soybean variety XB38E06 (US2006107366); Soybean variety XB37U06 (US2006107365); Soybean variety XB37Q06 (US2006107364); Soybean variety XB00D06 (US2006107363); Soybean variety XB14N06 (US2006107362); Soybean variety XB31H06 (US2006107361); Soybean variety XB21Z06 (US2006107360); Soybean variety XBO05B06 (US2006107359); Soybean variety XB15W06 (US2006107358); Soybean variety XB33N06 (US2006107357); Soybean variety XB18W06 (US2006107356); Soybean variety XB32M06 (US2006107355); Soybean variety XB19F06 (US2006107354); Soybean variety S03-95021-55-138-AB (U.S. Pat. No. 7,026,531); Soybean variety 94M41 (U.S. Pat. No. 7,002,061); Soybean variety 91M50 (U.S. Pat. No. 6,998,518); Soybean variety 92B13 (U.S. Pat. No. 6,989,475); Soybean variety 93B68 (U.S. Pat. No. 6,989,474); Soybean variety 93B09 (U.S. Pat. No. 6,979,759); Soybean variety 92M00 (U.S. Pat. No. 6,972,352); Soybean variety XB08P05 (US2005120433); Soybean variety XB26V05 (US2005150023); Soybean variety XB21R05 (US2005108795); Soybean variety XB28E05 (US2005114942); Soybean variety XB58K05 (US2005114941); Soybean variety XB27B05 (US2005114940); Soybean variety XB21S05 (US2005150022); Soybean variety XB26U05 (US2005138695); Soybean variety XB35K05 (US2005150021); Soybean variety XB18S05 (US2005120436); Soybean variety XB25C05 (US2005120435); Soybean variety 90M01 (US2005120434); Soybean variety XB22H05 (US2005150020); Soybean variety XB22K05

(US2005114939); Soybean variety XB58G05 (US2005114938); Soybean variety XB57U05 (US2005120432); Soybean variety XB49M05 (US2005120431); Soybean variety XB20D05 (US2005144683); Soybean variety XB41B05 (US2005150019); Soybean variety XB38T05 (US2005120430); Soybean variety XB13T05 (US2005120429); Soybean variety XB19Y05 (US2005120428); Soybean variety XB43D05 (US2005120427); Soybean variety XB40E05 (US2005120426); Soybean variety XB39N05 (US2005120425); Soybean variety 93M01 (US2005120424); SOYBEAN VARIETY XB31W05 (US2005223439); Soybean variety XB32C05 (US2005114937); Soybean variety XB40D05 (US2005120423); Soybean variety 92M61 (US2005120422); Soybean variety 91M91 (US2005114936); Soybean variety XB33Y05 (US2005120421); Soybean variety XB34A05 (US2005120420); Soybean variety XB13U05 (US2005114935); Soybean variety XB12K05 (US2005114934); Soybean variety XB30P05 (US2005120419); Soybean variety XB57T05 (US2005114933); Soybean variety XB17S05 (US2005114932); Soybean variety XB25Y05 (US2005114930); Soybean variety XB25S05 (US2005150017); Soybean variety XB43W04 (US2004177420); Soybean variety XB44W04 (US2004177419); Soybean variety XB53J04 (US2004199960); Soybean variety XB43V04 (US2004216192); Soybean variety XB49K04 (US2004172668); Soybean variety XB27P04 (US2004205864); Soybean variety XB29L04 (US2004177418); Soybean variety XB29K04 (US2004177417); Soybean variety XB41U04 (US2004231017); Soybean variety XB34D04 (US2004177416); Soybean variety XB09J04 (US2004172711); Soybean variety XB32Y04 (US2004194169); Soybean variety XB44D04 (US2004172710); Soybean variety XB44C04 (US2004172709); Soybean variety XB10L04 (US2004172708); Soybean variety XB19U04 (US2004172707); Soybean variety XB02F04 (US2004172706); Soybean variety XB25X04 (US2004172705); Soybean variety XB26L04 (US2004172704); Soybean variety XB11F04 (US2004172703); Soybean variety XB40Z04 (US2004177415); Soybean variety XB40Y04 (US2004181833); Soybean variety XBO07C04 (US2004181832); Soybean variety 96M20 (US2004172702); Soybean variety XB39J04 (US2004172701); Soybean variety XB29A04 (US2004172700); Soybean variety XB35P04 (US2004172699); Soybean variety XB58Z04 (US2004177414); Soybean variety XB43R04 (US2004172698); Soybean variety XB35L04 (US2004172697); Soybean variety XB06H04 (US2004172696); Soybean variety XB59U04 (US2004172695); Soybean variety XB64C04 (US2004172694); Soybean variety 95M80 (US2004172693); Soybean variety XB35Q04 (US2004177413); Soybean variety XB04D04 (US2004177412); Soybean variety XB08L04 (US2004177411); Soybean variety XB18Q04 (US2004177410); Soybean variety XB16Q04 (US2004177409); Soybean variety XB55K04 (US2004172692); Soybean variety XB57M04 (US2004172691); Soybean variety XB25L04 (US2004205863); Soybean variety XB48T04 (US2004194168); Soybean variety XB42X04 (US2004199959); Soybean variety XB31T04 (US2004177408); Soybean variety XB31U04 (US2004194167); Soybean variety XB30E04 (US2004177407); Soybean variety XB31R04 (US2004177406); Soybean variety S03-95341-A98-60618 (U.S. Pat. No. 6,909,033); Soybean variety 5N97-6946 (US2004168227); Soybean variety 94M70 (U.S. Pat. No. 6,864,408); Soybean variety 92M70 (U.S. Pat. No. 6,797,866); Soybean variety 92M71 (U.S. Pat. No. 6,858,782); Soybean variety 91M40 (U.S. Pat. No. 6,828,490); Soybean variety 93M80 (U.S. Pat. No. 6,849,789); Soybean variety XB39N03 (U.S. Pat. No. 6,864,407); Soybean variety 93M90 (U.S. Pat. No. 6,846,975); Soybean variety 90M90 (U.S. Pat. No. 6,852,913); Soybean variety 92M72 (U.S. Pat. No. 6,960,708); Soybean variety 91M90 (U.S. Pat. No. 6,849,788); Soybean variety 92M50 (U.S. Pat. No. 6,855,876); Soybean variety 92M30 (U.S. Pat. No. 6,951,974); Soybean variety 93M60 (U.S. Pat. No. 6,797,865); Soybean variety 93M40 (U.S. Pat. No. 6,791,016); Soybean variety 93M41 (U.S. Pat. No. 6,835,875); Soybean variety XB15P03 (U.S. Pat. No. 6,797,864); Soybean variety XB24H03 (U.S. Pat. No. 6,936,752); Soybean variety XB05A03 (U.S. Pat. No. 6,815,585); Soybean variety 92M80 (U.S. Pat. No. 6,849,787); Soybean variety XB33S03 (U.S. Pat. No. 6,855,875); Soybean variety XB48P03 (U.S. Pat. No. 6,797,863); Soybean variety XB29X03 (U.S. Pat. No. 6,806,406); Soybean variety XB02C03 (U.S. Pat. No. 6,800,795); Soybean variety XB29W03 (U.S. Pat. No. 6,858,781); Soybean variety 91M10 (U.S. Pat. No. 6,958,437); Soybean variety 92M10 (U.S. Pat. No. 6,916,975); Soybean variety XB10G03 (U.S. Pat. No. 6,806,405); Soybean variety 92M31 (U.S. Pat. No. 6,846,974); Soybean variety XB38D03 (U.S. Pat. No. 6,806,404); Soybean variety XB34N03 (U.S. Pat. No. 6,803,508); Soybean variety XB30W03 (U.S. Pat. No. 6,809,236); Soybean variety XB37J03 (U.S. Pat. No. 6,844,488); Soybean variety SE72581 (US2004148665); Soybean variety SE90076 (US2004148664); Soybean variety SD82997 (US2004148663); Soybean variety 0037393 (US2004148662); Soybean variety 0088414 (US2004148661); Soybean variety 0149926 (US2004148660); Soybean variety 0037209 (US2004148659); Soybean variety 93B36 (U.S. Pat. No. 6,833,498); Soybean variety 90B74 (U.S. Pat. No. 6,812,384); Soybean variety 90B51 (U.S. Pat. No. 6,818,809); Soybean variety 91B03 (U.S. Pat. No. 6,815,584); Soybean variety 95B43 (U.S. Pat. No. 6,818,808); Soybean variety 95B42 (U.S. Pat. No. 6,815,583); Soybean variety 92B47 (U.S. Pat. No. 6,812,383); Soybean variety SE90346 (US2004055055); Soybean variety 0007583 (US2004010824); Soybean variety 0008079 (US2004010823); Soybean variety 502-AP98041-2-333-01 (US2003121076); Soybean variety S02-98041-2-251-01 (US2003182694); Soybean variety 502-AP98041-2-262-02 (US2003196220); Soybean variety S02-95021-55-240-BA (US2003188348); Soybean variety APA94-31572 (US2003061641); Soybean variety AP98041-1-203 (US2003056251); Soybean variety APA95-15294 (US2003061640); Soybean variety AP98041-4-117 (US2003056250); Soybean variety 91B33 (U.S. Pat. No. 6,580,018); Soybean variety 93B85 (U.S. Pat. No. 6,605,762); Soybean variety 92B76 (U.S. Pat. No. 6,610,911); Soybean variety 92B38 (U.S. Pat. No. 6,605,761); Soybean variety 94B24 (U.S. Pat. No. 6,613,967); Soybean variety 94B73 (U.S. Pat. No. 6,605,760); Soybean variety 93B86 (U.S. Pat. No. 6,610,910); Soybean variety 91B12 (U.S. Pat. No. 6,583,343); Soybean variety 95B34 (U.S. Pat. No. 6,605,759); Soybean variety 94B23 (U.S. Pat. No. 6,605,758); Soybean variety 90B11 (U.S. Pat. No. 6,583,342); Soybean variety 91B92 (U.S. Pat. No. 6,586,659); Soybean variety 95B96 (U.S. Pat. No. 6,605,757); Soybean variety 93B72 (U.S. Pat. No. 6,566,589); Soybean variety 95B97 (U.S. Pat. No. 6,613,966); Soybean variety 92B95 (U.S. Pat. No. 6,608,243); Soybean variety 93B47 (U.S. Pat. No. 6,583,341); Soybean variety 97B52 (U.S. Pat. No. 6,605,756); Soybean variety 93B15 (U.S. Pat. No. 6,617,499); Soybean variety 94B54 (U.S. Pat. No. 6,613,965); Soybean variety 93B67 (U.S. Pat. No. 6,573,433); Soybean variety 93B87 (U.S. Pat. No. 6,727,410); Soybean variety 96B51 (U.S. Pat. No. 6,613,964); Soybean variety 92B84 (U.S. Pat. No. 6,730,829); Soybean variety 92B12 (U.S. Pat. No. 6,605,755); Soybean variety 90A07 (U.S. Pat. No. 6,320,105); Soybean variety 93B26 (U.S. Pat. No. 6,342,659); Soybean variety 96B21 (U.S. Pat. No. 6,369,301); Soybean variety 92B63 (U.S. Pat. No. 6,326,529); Soybean variety 93B46 (U.S. Pat. No. 6,323,402); Soybean variety 92B75 (U.S. Pat. No. 6,362,400); Soybean variety 93B08 (U.S. Pat. No. 6,323,401); Soybean variety 97B62 (U.S. Pat. No. 6,323,400); Soybean variety 92B37 (U.S. Pat. No. 6,323,399); Soybean variety 92B56 (U.S. Pat. No. 6,339,186); Soybean variety 93B66 (U.S. Pat. No. 6,307,131); Soybean variety 92B62 (U.S. Pat. No. 6,346,657); Soybean variety 92B36 (U.S. Pat. No. 6,369,300); Soybean variety 90B73 (U.S. Pat. No. 6,316,700); Soybean variety 95B95 (U.S. Pat. No. 6,323,398); Soybean variety 93B65 (U.S. Pat. No. 6,229,074); Soybean variety 92B24 (U.S. Pat. No. 6,284,950); Soybean variety 94B53 (U.S. Pat. No. 6,235,976); Soybean variety 94B22 (U.S. Pat. No. 6,140,557); Soybean variety 93B84 (U.S. Pat. No. 6,143,956); Soybean variety 95B32 (U.S. Pat. No. 6,229,073); Soybean variety 95B53 (U.S. Pat. No. 6,147,283); Soybean variety 93B35 (U.S. Pat. No. 6,153,816); Soybean variety 93B07 (U.S. Pat. No. 6,143,955); Soybean variety 92B74 (U.S. Pat. No. 6,124,526); Soybean variety 92B35 (U.S. Pat. No. 6,166,296); Soybean variety 94B45 (U.S. Pat. No. 6,162,968); Soybean variety 96B01 (U.S. Pat. No. 6,143,954); Soybean variety 93B53 (U.S. Pat. No. 6,335,197).

In some embodiments, the plant cells of the invention, i.e. a plant cell comprising a knock-out rod1 gene or an RNA inhibitory to a ROD1 gene, as well as plant cells generated according to the methods of the invention, may be non-propagating cells.

The obtained plants according to the invention can be used in a conventional breeding scheme to produce more plants with the same characteristics or to introduce the characteristic according to the invention in other varieties of the same or related plant species. The obtained plants can further be used for creating propagating material. Plants according to the invention can further be used to produce gametes, seeds (including crushed seeds and seed cakes), seed oil, embryos, either zygotic or somatic, progeny, or to produce food or feed, such as oil, meal, grain, starch, flour or protein, or an industrial product, such as biofuel, fiber, industrial chemicals, a pharmaceutical or a neutraceutical.

All patents, patent applications, and publications or public disclosures (including publications on internet) referred to or cited herein are incorporated by reference in their entirety.

The sequence listing contained in the file named "BCS12-2012ST25.txt", which is 31.1 kilobytes (size as measured in Microsoft Windows®), contains 6 sequences SEQ ID NO: 1 through SEQ ID NO: 6 and was created on 2 Jul. 2012 is filed herewith by electronic submission and is incorporated by reference herein.

In the description and examples, reference is made to the following sequences:

SEQUENCES

SEQ ID No. 1: Genomic DNA sequence of ROD1-1 from soybean.
SEQ ID No. 2: cDNA sequence of ROD1-1 from soybean.
SEQ ID No. 3: protein sequence of ROD1-1 from soybean.
SEQ ID No. 4: Genomic DNA sequence of ROD1-2 from soybean.
SEQ ID No. 5: cDNA sequence of ROD1-2 from soybean.
SEQ ID No. 6: protein sequence of ROD1-2 from soybean.

EXAMPLES

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany. Standard procedures for AFLP analysis are described in Vos et al. (1995, NAR 23:4407-4414) and in published EP patent application EP 534858.

Example 1

Isolation of the DNA Sequences of Soybean ROD1 Genes

The *Glycine max* ROD1 cDNA sequences were derived from the genomic sequence Gm08-Chromosome8 from bp 17252266 to bp 17258532 exported from the database Glycine_max_JGI_Genome_V1. The intron-exon boundries were identified using the EST sequences BW670367, AW733693, BW670368 and HO041720.

Example 2

Generation and Isolation of Mutant Soybean rod1 Alleles

Soybean seeds (5,000 as a minimum) are placed in a container and flushed with tap water (28 C) through the seeds for 12 hours. Seeds are then transferred to 0.1M KH2PO4 pH 6.0 (1 liter/1,000 seeds) and ethyl methane sulfonate (EMS) is added to give a final concentration of 0.5% (v/v) and the solution in bubbled with air. After six hours exposure to EMS, the mutagen solution is removed and the container is filled with water. The seeds are washed for 4 hours. The mutagenized seeds (M1 seeds) are planted immediately, grown in soil and selfed to generate M2 seeds.

M2 plants, derived from different M1 plants, are grown and DNA samples are prepared from leaf samples of each individual M2 plant. The DNA samples are screened for the presence of point mutations in the ROD1 genes causing the introduction of STOP codons in the protein-encoding regions of the ROD1 genes, amino acid substitutions, or the disruption of splice sites in the ROD1 mRNA, by direct sequencing by standard sequencing techniques and analyzing the sequences for the presence of the point mutations using the NovoSNP software.

Mutant rod1 alleles have been identified of the GmROD1-1 gene and of the GmROD1-2 gene.

Example 3

Activity of GmROD1 Alleles in Yeast

The activity of the soybean ROD1-1 and ROD1-2 alleles, as well as mutant alleles thereof, are tested in yeast.

Cloning of the ROD1 Alleles in Yeast Expression Vectors

GmROD1-1 and GmROD1-2 and their mutant alleles are amplified by KOD DNA polymerase (Toyobo Life Science Department, http://www.toyobo-global.com), using primers that created 5' BamHI and 3'EcoRI restriction sites.

Following BamHI and EcoRI double digestion, each product is ligated into the p424GPD vector (ATCC, http://www.atcc.org/), in which the CDNA is expressed under control of the constitutive Glyceraldehyde-3-P dehydrogenase promoter, and then transformed into E. coli competent cells (TOP10, Invitrogen). Plasmids with correct inserts confirmed by sequencing are transformed into yeast HJ091 cells (cpt1::LEU2 ept1-), and transformants are selected by synthetic minimal media (SD base) with dropout leucine and tryptophan (DO-Leu/-Trp) (Clontech, http://www.clontech.com).

Activity Testing of the ROD1 Alleles in Yeast

ROD1 activity assay is modified based on Supplementary Information in Lu et al., 2009 (PNAS, 2009, 106 (44): 18837-18842., S1 Materials and Methods). Yeast cells are inoculated from overnight cultures and grown to mid-log phase (0D600=0.5-1.5) at 30° C. in liquid media SD/-Leu/-Trp. To prepare a total membrane fraction, 100 ml yeast cells are harvested by centrifugation at 1500 g for 5 min. Each cell pellet is washed once with sterile water and then resuspended in ice-cold glucose-Tris-EDTA (GTE) buffer [20% glycerol, 50 mM glucose, 25 mM Tris-HCl, pH 7.4, 10 mM EDTA]. Cells are then vortexed for 30 seconds×8 times with 30 seconds gaps on ice. The resulting homogenate is centrifuged at 2,500 g at 4° C. for 10 min. to pellet cell debris. The supernatant is centrifuged at 100,000 g at 4° C. for 1 h and the membrane pellet is resuspended in 200 µL GTE buffer. The protein concentration is determined by Bradford assay.

The PDCT activities in membrane preparations of HJ091 cells transformed with p424GPD (control) or p424ROD1 and mutant alleles are determined as the amount of [14C] dioleoyl-PC produced from 1,2-dioleoyl-rac-glycerol[14C (U)] ([14C-glycerol]diolein). The substrates of 1.8 nmol (200,000 cpm) [14C-glycerol]diolein (American Radiolabeled Chemicals, Inc. (http://www.arcinc.com) and 0.1 µmol dioleoyl-PC are dried under nitrogen gas and resuspended in 50 µL of 4× reaction buffer [final concentrations: 50 mM 3-(N-morpholino)propanesulfonic acid (MOPS)/NaOH (pH 7.5), 20 mM MgCl2, 0.45% Triton X-100] by 2 minutes sonication in a bath sonicator. Reactions (200 µL) are started by adding 50 ng of microsomal proteins suspended in the GTE buffer. Assays are incubated at 15° C. for 15 min and are terminated by the addition of 3 mL of chloroform/ethanol (2:1, vol./vol.), followed by 1.5 mL of 0.9% KCl. Tubes are mixed by vortexing, and phase separation was facilitated by centrifugation at 2,000 g for 2 min. The aqueous phase is aspirated, and the organic phase is washed twice with 1.5 mL of 40% (vol./vol.) ethanol. Samples are analyzed by TLC on Whatman Partisil® K6 silica gel 60Å20×20 cm glass plates (Whatman, http://www.whatman.com) in a solvent system of chloroform/methanol/water (65:25:4, by volume), followed by phosphorimaging analysis (phosphorimager 445 SI, Lab Extreme, Inc, http://www.labextreme.com). Corresponding bands are scraped, and radioactivity is determined by scintillation counting on a TRI-CARBO liquid scintillation analyzer (Packard Instrument Company).

It is found that GmROD1-1 and GmROD1-2 have activity, whereas no activity of the mutant GmROD1-1 and mutant GmROD1-2 alleles can be detected.

Example 4

Downregulation of GmROD1 in Soybean

The ROD1 genes are downregulated in soybean using hairpin constructs of ROD1.

Construction of the ROD1 Hairpin Constructs

Host Escherichia coli strains are TOP10 (with Gateway entry and expression clones) or DB3.1 (with pHELLSGATE12 destination vector; Invitrogen). Bacterial cultures are grown at 37° C. in Luria broth medium with appropriate antibiotics.

Generation of ROD1 hpRNA Suppression Constructs:

To specifically knock down the expression of GmROD1-1 and GmROD1-2, a hairpin construct is generated which contains at least 20 bp identical to both GmROD1-1 and GmROD1-2. Therefore, a fragment of GmROD1-1 is amplified by PCR on GmROD1-1 DNA as template: The PCR reaction (50 µL) contained 0.3 µM of each primer, 2 ng/µL template DNA, 0.2 mM of dNTP mix, 0.02 unit/µL of KOD DNA polymerase (Toyobo), 5 µl of 10×PCR buffer, and 1.5 mM MgOS4. Programmed cycles are as follows: 2 min initial denaturing step at 95° C.; 40 cycles of 20 s denaturation at 95° C., 15 s annealing at 55° C., 20 s extension at 70° C. PCR products are purified with QIAquick Gel Extraction Kit (QIAGEN) and ligated into the pENTR™/D-TOPO® cloning vector (Invitrogen) to generate entry clones according to the manual's instruction. To generate hairpin constructs, 100 ng GmROD1 entry clone and 150 ng pHELLSGATE12 destination vector are mixed, and LR recombination reaction is conducted using Gateway® LR Clonase™ Enzyme following the manual's instruction (Invitrogen). After transformation into TOP10 competent cells, clones are screened by restriction analysis to identify plasmids with the expected insert in the correct orientation, and are validated by sequencing.

The transformation vectors are obtained by extracting the hairpin region from the above hairpin constructs and placing this cassette into a transformation vector under control of the Cauliflower Mosaic Virus 35S promoter containing bar as selectable marker.

Transformation of Soybean with the ROD1 Hairpin Constructs

A DNA fragment comprising the hairpin construct and the bar selectable marker is HPLC purified and used to obtain transformed soybean plants by means of direct gene transfer into cells of soybean, followed by regeneration of transformed plant cells into transgenic fertile soybean plants.

Single-copy regenerated transformation events are backcrossed with a soybean (elite) line. Following 2 rounds of selfing seeds from both homozygous transformation events and wild type segregants are harvested for subsequent seed oil analysis.

Oil Composition in Seeds from Soybean Transformed with the ROD1 Hairpin Constructs The fatty acid composition of the seed oil of individual progeny soybean plants for homozygous transformation events and the corresponding wild type segregants as well as a non-transformed reference line is determined by extracting the fatty acyls from the seeds and analyzing their relative levels in the seed oil by capillary gas-liquid chromatography as described in WO09/007091.

It is found that the levels of C18:1 is significantly increased in seed lipids of the plants comprising the hairpin construct as compared to wild-type controls or wild-type segregants. These results show that downregulation of the GmROD1-1 and/or GmROD1-2 alleles contributes significantly to the increase of C18:1 levels in the seed lipid fraction.

Further, it is found that the levels of C18:2 and of saturated fatty acids (SATS; C12:0, C14:0, C16:0, C18:0, C20:0, C22:0 and C24:0) are decreased in seeds of plants comprising the ROD1 hairpin construct as compared to wild-type controls or wild-type segregants.

Example 5

Oil Composition in Soybeans Comprising GmROD1-1 and GmROD1-2 Knock-out Alleles

Soybean plants comprising mutant ROD1-1 and ROD1-2 alleles are crossed. Following 2 rounds of selfing seeds from plants homozygous for ROD1-1 and ROD1-2 mutations, for the ROD1-1 mutation, for the ROD1-2 mutation or wild type segregants (i.e. not comprising any mutant ROD1 allele that would impact the normal function of a ROD1 protein) are obtained.

Fatty acid composition is determined as described above in F1S2 seeds of the soybean lines with mutant GmROD1-1, GmROD1-2, and combinations thereof. For each combination of mutants, oil composition is determined in wild-type segregants not comprising the respective mutations in GmROD1-1 and GmROD1-2, in lines homozygous for either the mutant GmROD1-1 or for the mutant GmROD1-2 allele, and in lines homozygous for both mutants GmROD1-1 and GmROD1-2.

It is found that the levels of C18:1 are increased in lines comprising either the mutant GmROD1-1, or for the mutant GmROD1-2 allele, or both mutants GmROD1-1 and GmROD1-2 as compared to the wild-type segregant. Further, the levels of C18:2 and of SATS (SATS; C12:0, C14:0, C16:0, C18:0, C20:0, C22:0 and C24:0) are decreased in lines comprising either the mutant GmROD1-1, or the mutant GmROD1-2 allele, or both mutants GmROD1-1 and GmROD1-2 as compared to the wild-type segregant.

Example 6

Detection and/or Transfer of Mutant ROD1 Alleles into (Elite) Soybean Lines

The mutant ROD1 genes are transferred into (elite) soybean breeding lines by the following method: A plant containing a mutant ROD1 gene (donor plant), is crossed with an (elite) soybean line (elite parent/recurrent parent) or variety lacking the mutant ROD1 gene. The following introgression scheme is used (the mutant ROD1 allele is abbreviated to rod1 while the wild type is depicted as ROD1):

BC1 cross: rod1/rod1 (donor plant)×ROD1/ROD1 (elite parent)

F1 plant: ROD1/rod1

BC2 cross: ROD1/rod1×ROD1/ROD1 (recurrent parent)

BC2 plants: 50% ROD1/rod1 and 50% ROD1/ROD1

The 50% ROD1/rod1 are selected using molecular markers (e.g. AFLP, PCR, Invader™, TaqMan®, KASP assay, and the like; see also below) for the mutant ROD1 allele (rod1).

BC3 cross: ROD1/rod1 (BC1 plant)×ROD1/ROD1 (recurrent parent)

BC3 plants: 50% ROD1/rod1 and 50% ROD1/ROD1

The 50% ROD1/rod1 are selected using molecular markers for the mutant ROD1 allele (rod1).

Backcrossing is repeated until BC4 to BC7.

BC4-7 plants: 50% ROD1/rod1 and 50% ROD1/ROD1

The 50% ROD1/rod1 are selected using molecular markers for the mutant ROD1 allele (rod1). To reduce the number of backcrossings (e.g. until BC4 instead of BC7), molecular markers can be used specific for the genetic background of the elite parent.

BC4-7 S1 cross: ROD1/rod1×ROD1/rod1

BC4-7 S1 plants: 25% ROD1/ROD1 and 50% ROD1/rod1 and 25% rod1/rod1

Plants containing rod1 are selected using molecular markers for the mutant ROD1 allele (rod1). Individual BC4-7 S1 or BC4-7 S2 plants that are homozygous for the mutant ROD1 allele (rod1/rod1) are selected using molecular markers for the mutant and the wild-type ROD1 alleles. These plants are then used for seed production.

To select for plants comprising a point mutation in a ROD1 allele, direct sequencing by standard sequencing techniques known in the art can be used.

Alternatively, Invader™ technology (Third Wave Agbio) can be used to discriminate plants comprising a specific point mutation in an ROD1 allele from plants not comprising that specific point mutation. Discriminating Invader™ probes are thus developed to detect the presence or absence and the zygosity status of mutant alleles identified in Example 3, based on the single nucleotide difference between the mutant and wildtype allele. Briefly, probes specific for the mutant or corresponding wild-type target ROD1 gene and "invading" probes which can be used in combination with them are developed. Generally, each probe set consists of one probe specific for the mutant or the wild type target gene of which the first nucleotide after the "5' flap" sequence matches with the nucleotide difference (the so-called "primary probe") and one probe specific for the nucleotides upstream of the nucleotide difference (the so-called "invader® oligo"). The last nucleotide of the latter primer may match with the nucleotide difference in the mutant, but other nucleotides may be used as well for this last nucleotide as long as the primary probe and the invader® oligo are still able to form a single base overlap when hybridized to the target DNA to generate the specific invasive structure recognized by the Cleavase® enzymes (Third Wave Agbio). The Invader™ assay procedure and interpretation of the data are performed as prescribed by the manufacturer (Third Wave Agbio). Briefly, 5' "flap" nucleotide sequences (flap1 for the mutant allele and flap2 for the wild-type allele) are cleaved from the primary probes in the primary phase of the Invader™ assay and are complementary to sequences in FRET™ cassette 1 and 2, respectively, and not complementary to the target mutant or wild type sequences. If the primary probes are cleaved in the primary phase and the flap1-probe and/or flap2-probe hybridise to FRET™ cassette 1 and 2, respectively, in the secondary phase, a signal is generated indicative of the presence in the sample of the mutant or corresponding wild-type target ROD1 gene, respectively.

Alternatively, KASP assays (KBioscience) can be used to discriminate plants comprising a specific point mutation in an ROD1 allele from plants not comprising that specific point mutation. Discriminating primers are developed to detect the presence or absence and the zygosity status of mutant alleles identified in Example 2.

Briefly, forward primers specific for the mutant or corresponding wild-type target ROD1 gene and a reverse primer that can be used in combination with them are developed. The nucleotide at the 3' end of the forward primers corresponds to the nucleotide which differs between the mutant and the corresponding wild-type allele. The primers can be used in combination with fluorescent dyes, such as FAM and VIC according to the protocol as described by the manufacturer (KBioscience).

The invention claimed is:

1. A soybean plant, or a cell, part, seed or progeny thereof, comprising two ROD1 genes, characterized in that at least one ROD1 gene is a knock-out rod1 gene, wherein said knock-out rod1 gene is a knock-out allele of the ROD1 gene encoding a protein having at least 90% sequence identity to SEQ ID No. 3 or SEQ ID No. 6.

2. The plant, or a cell, part, seed or progeny thereof, of claim 1, comprising two knock-out rod1 genes.

3. The plant of claim 1 which is homozygous for the knock-out ROD1 gene.

4. A transgenic soybean plant, or a cell, part, seed or progeny thereof, comprising two ROD1 genes, comprising a chimeric gene, said chimeric gene comprising the following operably linked DNA fragments:
   a) a plant-expressible promoter;
   b) a DNA region, which when transcribed yields an RNA molecule inhibitory to at least one ROD1 gene; and optionally
   c) a transcription termination and polyadenylation region functional in plant cells
wherein said RNA molecule is inhibitory to a ROD1 gene encoding a protein having at least 90% sequence identity to SEQ ID No. 3 or SEQ ID No. 6.

5. Seeds from the plant of claim 1, said seeds comprising two ROD1 genes, wherein said seeds comprise the knock-out ROD1 alleles as defined in claim 1, or the plant of claim 4, comprising the chimeric gene as defined in claim 4.

6. A method for increasing the levels of C18:1 and/or decreasing the levels of saturated fatty acids in soybean seed oil, comprising the steps of:
   a) introducing or providing a chimeric gene to a soybean plant cell, to create transgenic cells, said chimeric gene comprising the following operably linked DNA fragments:
      a plant-expressible promoter;
      a DNA region, which when transcribed yields an RNA molecule inhibitory to at least one ROD1 gene; and optionally
      a transcription termination and polyadenylation region functional in plant cells; and
   b) regenerating transgenic plants from said transgenic cells
wherein said RNA molecule is inhibitory to a ROD1 gene encoding a protein having at least 90% sequence identity to SEQ ID No. 3 or SEQ ID No. 6.

7. A method for increasing the levels of C18:1 and/or decreasing the levels of saturated fatty acids in soybean seed oil, comprising the steps of:
   a) treating seeds or plant material with a mutagenic chemical substance or with ionizing radiation;
   b) identifying plants with a mutated ROD1 gene, wherein the ROD1 gene, prior to being mutated, encodes a polypeptide having at least 90% sequence identity to SEQ ID No. 3, or to SEQ ID No. 6; and
   c) selecting a plant with an increased level of C18:1 in the seeds compared to a plant in which the ROD1 gene is not mutated.

8. A method for obtaining a soybean plant with increased levels of C18:1 and/or decreased levels of saturated fatty acids in the seeds comprising the step of introducing a knock-out allele of a ROD1 gene as defined in claim 1 in said soybean plant, and selecting said soybean plant with increased levels of C18:1 in the seeds for the presence of said knock-out allele of a ROD1 gene by analyzing genomic DNA from said plant for the presence of at least one molecular marker, wherein said at least one molecular marker is linked to said knock-out allele of a ROD1 gene.

9. A method for transferring at least one knock-out ROD1 allele as defined in claim 1 from one soybean plant to another soybean plant comprising the steps of:
   (a) identifying a first soybean plant comprising at least one knock-out ROD1 allele as defined in claim 1,
   (b) crossing the first soybean plant with a second soybean plant not comprising the at least one knock-out ROD1 allele and collecting F1 seeds from the cross,
   (c) optionally, identifying F1 soybean plants comprising the at least one knock-out ROD1 allele,
   (d) backcrossing F1 soybean plants comprising the at least one knock-out ROD1 allele with the second soybean plant not comprising the at least one knock-out ROD1 allele for at least one generation (x) and collecting BCx seeds from the crosses,
   (e) identifying in every generation BCx soybean plants comprising the at least one knock-out ROD1 allele by analyzing genomic DNA of said BCx plants for the presence of at least one molecular marker, wherein the at least one molecular marker is linked to said knock-out ROD1 allele.

* * * * *